(12) United States Patent
Marinkovich

(10) Patent No.: US 7,323,551 B2
(45) Date of Patent: Jan. 29, 2008

(54) COMPOSITIONS AND METHODS FOR INHIBITING SQUAMOUS CELL CARCINOMA

(75) Inventor: M. Peter Marinkovich, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 229 days.

(21) Appl. No.: 10/766,317

(22) Filed: Jan. 27, 2004

(65) Prior Publication Data

US 2006/0009630 A1    Jan. 12, 2006

(51) Int. Cl.
*C07K 16/00*    (2006.01)
(52) U.S. Cl. .................................... 530/388.1
(58) Field of Classification Search ............... None
See application file for complete search history.

(56) References Cited

U.S. PATENT DOCUMENTS

| | | | |
|---|---|---|---|
| 4,816,567 A | 3/1989 | Cabilly et al. | |
| 6,120,991 A * | 9/2000 | Carter et al. .............. | 435/6 |
| 6,294,356 B1 | 9/2001 | Jones et al. | |
| 2002/0076736 A1 | 6/2002 | Findell et al. | |

FOREIGN PATENT DOCUMENTS

WO    WO0026342 A    5/2000

OTHER PUBLICATIONS

Ahmed et al. "Chapter 39, Immunity to Viruses" *Fundamental Immunology*, 4th edition, W. E. Paul, ed., Lippincott-Raven Publishers, 1999, Chapter 39, pp. 1295-1334.
Alama et al., "Antisense Oligonucleotides as Therapeutic Agents" (1997) *Pharmacol Res.* 36(3):171-178.
Amano et al., "Bone morphogenetic protein 1 is an extracellular processing enzyme of the Laminin 5Y2 chain" 2000, J. Biol. Chem., 275: 22728-35.
Boado et al., "Drug delivery of antisense molecules to the brain for treatment of Alzheimer's disease and cerebral AIDS" 1998, *J. Pharm. Sci.* 87 (11): 1308-1315.
Cassidy et al., "Malanocytes adhere to and synthesize laminin-5 n vitro" *Ep. Derm.* 1999, 8, 212-221.
Chan et al. "Laminin-6 and Laminin-5 are recognized by Autoantibodies in a subset of cicatricial pemphigoid" *Society for Invs. Derm.*, 1997, 848-853.
Chen et al. "NC1 Domain of Type VII Collagen Binds to the β3 chain of laminin 5 via a Unique Subdomain Within the Fibronectin-like repeats" (1999) *J. for Invest Derm.*, 177-183.
Crooke, S. T., "Advances in understanding the pharmacological properties of antisense oligonucleotides" 1997, *Adv. Pharmacol.* 40:1-49.
Dajee et al., "NF-κB blockade and oncogenic Ras trigger invasive human epidermal neoplasia" *Nature* vol. 421, 2003, 639-643.
Diederichsen, U., "Alanyl-PNA homoduplex: A-T Pairing with the N7-Regioisomer of Adenine" 1998, *Bioorganic & Med. Chem. Lett.*, 8:165-168.
Fukushima et al., "Integrin α3β1-mediated interaction with lamin-5 stimulates adhesion, migration and invasion of malignant glioma cells" 1998, *Int. J. Cancer*, 76: 63-72.
Huse et al., "Generation of a large combinatorial library of the immunoglobulin repertoire in phage lambda" 1989, *Science*, 254: 1275-1281.
Jordan et al., "New Hetero-oligomeric peptide nucleic acids with improved binding properties to complementary DNA" (1997) *Bioorg. Med. Chem. Lett.* 7: 687-690.
Jordan et al. "Synthesis of new building blocks for peptide nucleic acids containing monomers with variations in the backbone" (1997) *Bioorg. Med. Chem. Lett.* 7: 637-627.
Kirtsching et al. "Anti-basement membrane autoantibodies in patients with anti-peiligrin cicatricial pemphigoid bind the α subunit of laminin 5", *J. Invest. Derm.* (1995) 105, 543-548.
Kumar et al., "Pyrrolidine Nucleic Acids: DNA/PNA Oligomers with 2-hydroxylaminoethyl-4(thymin-1-yl) pyrrolidine-N-acetic acid" 2001, *Organic Letters* 3(9): 1269-1272.
Lavrosky et al., "Therapeutic potential and mechanism of action of oligonucleotides and ribozymes" 1997, *Biochem. Mol. Med.*, 62(1):11-22.
Lee et al., "Polyamide Nucleic Acid Targeted to the Primer Binding Site of the HIV-1 RNA Genome Blocks in vitro HIV-1 Reverse Transcription" 1998, *Biochemistry* 37 (3): 900-1010.
Li et al. "Laminin-10 is crucial for hair morphogenesis" *the EMBO Journal*, vol. 22, No. 10, pp. 2400-2410.
Maddox et al., "Elavated serum levels in human pregnancy of a molecule immunochemically similar to eosinophil granule major basic protein" 1983, *J Exp Med*, 158: 1211.
Marcus-Sakura "Techniques for using antisense oligodeoxyribonucleotides to study gene expression" (1988) *Anal. Biochem.* 172:289.
Marinkovch et al. Basement Membrane Proteins Kalinin and Nicein are Structurally and Immunologically Identical: *Lab. Invest.*, 1993, vol. 69, No. 3, pp. 295-299.
Marinkovich et al., "The dermal-epidermal junction of human skin contains a novel laminin variant" *J. Cell. Biol.* vol. 119, No. 3, 1992, 695-703.
Marinkovich M. P. et al, "The Anchoring Filament Protein Kalinin is Synthesized and Secreted as a High Molecular Weight Precursor", *Journal of Biological Chemistry*, vol. 267, No. 25, 1992, pp. 17900-17906.
McGowan et al. "Laminins and human disease" *Microscopy Res. and Tech.* 51::262-279 (2000).
Meneguzzi et al. "Kalinin is abnormally expressed in epithelial basement membranes of Herliz's junctional epidermolysis bullosa patients" *Exp. Derm.* 1992, pp. 221-229.
Meneguzzi et al., "Kalinin is abdnormally expressed in epithelial basement membranes of Herlizts junctional epidermolysis bullosa patients", 1992, *Exp. Derm*, 1, 221-229.

(Continued)

Primary Examiner—Misook Yu
Assistant Examiner—Mark Halvorson
(74) Attorney, Agent, or Firm—Bozicevic, Field & Francis LLP; Pamela J. Sherwood

(57) ABSTRACT

The present invention relates to compositions and methods for detecting and inhibiting squamous cell carcinoma using agents that target the laminin 5 alpha 3 G4-G5 domain.

4 Claims, 28 Drawing Sheets

OTHER PUBLICATIONS

Miller, "Progress Toward Human Gene Therapy" 1990, *Blood,* 76: 271.

Miquel et al., Establishment and Characterization of cell line LSV5 that retains the altered adhesive properties of human junctional epidermolysis bullosa keratinocytes, *Exp. Cell. Res.,* 224, 279-290 (1996).

Mizushima H. et al., Identification of Integrin-dependent and independent cell adhesion domains in cooh-terminal globular region of alminin-5 alpha3 chain *Cell Growth and Differentiation,* The Association, Phil. Pa, US, vol. 8, No. 9, Sep. 1997, pp. 979-987.

Morris et al., "A new peptide vector for efficient delivery of oligonucleotides into mammalian cells" 1997, *Nucl. Acids Res.*25 (14): 2730-2736.

Nielsen, P. E. and G. Haaima, "Peptide nucleic acid (PNA). a DNA mimic with a pseudopeptide backbone" 1997, *Chem. Soc. Rev.* 96:73-78.

O'Toole et al. "Laminin-5 inhibits human keratinocyte migration" *Exp. Cell. Res.* 233, 330-339 (1997).

Orlandi et al., "Cloning immunoglobulin variable domains for expression by the polymerase chain reaction" 1989, *Proc. Natl. Acad. Sci.* 86: 3833-3837.

Ortiz-Urda et al. "Injection of genetically engineered fibroblasts corrects regenerated human epidermolysis bullosa skin tissue" *J. Clin. Invest.* 2003, vol. 111, No. 2, pp. 251-255.

Pardridge et al., "Vector-mediated delivery of a polyamide ("peptide") nucleic acid analogue through the blood-brain barrier in vivo" 1995, *Proc. Nat. Acad. Sci.* 92 (12):5592-5596.

Pyke et al., "Laminin-5 is a marker of invading cancer cells in some human carcinomas and is coexpressed with the receptor for urokinase plasminogen activator in budding cancer cells in colon adenocarcinomas" 1995, *Canc. Res.* 55: 4132-4139; Berndt et al., 1997, *Invasion and Metastasis,* 17: 251-258.

Pyke, et al., "The γ2 chain of kalinin/Laminin 5 is preferentially expressed in invading malignant cells in human cancers" 1994, *Am. J. Pathol.* 145(4): 782-791.

Rammensee; H., et al. "SYFPEITHI: database for MHC ligands and peptide motifs": (1999) *Immunogenetics,* 50:213-219.

Rossi et al., "Exploring the use of antisense, enzymatic RNA molecules (Ribozymes) as therapeutic agents" 1991, *Antisense Res. Dev.* 1(3):285-288.

Rossi, "Therapeutic antisense and ribozymes" 1995, *Br. Med. Bull.* 51 (1): 217-225.

Russell et al., "α6β4 integrin regulates keratinocyte chemotaxis through differential GTPase activation and antagonism of α3β1 integrin" 2003, *J. Cell Sci.* 116 (17)3543-3556.

Ryan et al. "Cloning of the LamA3 Gene encoding the alpha3 chain of the adhesive ligand epiligrin" *J. Bio. Chem.* vol. 269, No. 36, pp. 22779-22787 (1984).

Slater et al., "The latex allergen Hev b 5 transcript is widely distributed after subcutaneous injection in BALB/c mice of its DNA vaccine" 1998, *J. Allergy Cli. Immunol.* 102 (3): 469-475.

Stoltzfus P. et al., Lamin-5 Gamma2 Chain Expression Facilitates Detection of Invasive Squamous Cell Carcinoma of the Uterine Cervix, *Inernational Journal of Gynecological Pathology,* vol. 23, No. 3, Jul. 2004, pp. 215-222.

Uckert and Walther, "Retrovirus-mediated gene transfer in cancer therapy" 1994, *Pharacol. Ther.,* 63(3): 323-347.

van Hest et al., "Efficient introduction of alkene functionality into proteins in vivo" *FEBS Lett* 428:(1-2) 68-70 May 22, 1998.

Veitch et al., "Mammalian Tolloid Metalloproteinase, and not matrix metalloprotease 2 or membrane type 1 metalloprotease, processes laminin-5 in keratinocytes and skin" 2003, *J. Biol. Chem.,* 278: 15661-15668.

Verhoeyen et al., "Reshaping human antibodies: grafting an antilysozyme activity" 1988, *Science,* 239: 1534-1536.

Weinberg et al. "How cancer arises: an explosion of research in uncovering the long-hidden molecular underpinnings of cancer and suggesting new therapies" *Scientific American* (1996) (Sep.) pp. 62-70.

Winter, G. and C. Milstein, "man-made intibodies" 1991, *Nature,* 349: 293-299.

Yi-shan et al. "Self-assembly of Laminin Isoforms" *J. Bio. Chem.* vol. 272, No. 50, pp. 31525-31532 (1997).

Cheng et al. "Self-assembly of laminin isoforms*", *J.Biol.Sci.,* vol. 272, No. 50., pp. 31525-31532 (1997).

Marinkovich et al. "LAD-1 is absent in a subset of junctional epidermolysis bullosa patients" *The Society for Investing Derm.* (1995) vol. 15, pp. 1027-1034.

Marinkovich et al. "Prenatal diagnosis of herlitz junctional epidermolysis bullosa by amniocentesis" *Prenatal Diagnosis* (1995) vol. 15, 1027-1034.

Marinkovich et al. "Basement membrane proteins kalinin and nicein are structurally and immunologically identical" *Lab. Invest.* (1993), vol. 69, No. 3, 295-.

Marinkovich et al. "The molecular genetics of basement membrane diseases" *Arch.Derm.* (1993) vol. 129, 1557.

Marinkovich et al. "The anchoring filament protein kalinin is synthesized and secreted as a high molecular weight precursor" *J. Biol. Chem.* (1992) vol. 267, No. 25, pp. 17900-17906.

Marinkovich et al. "the dermal-epidermal junction of human skin contains a novel laminin variant" (1992) *J. Cell Biol.,* vol. 119, No. 3, 695-703.

* cited by examiner

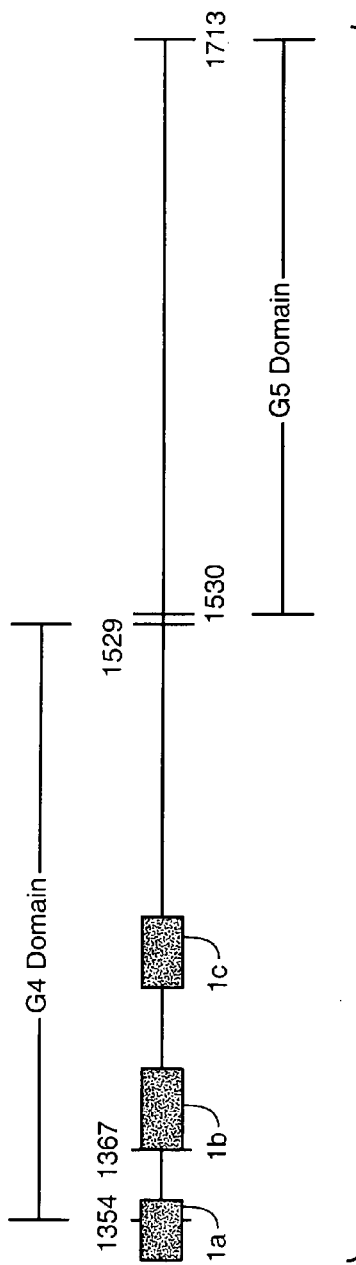
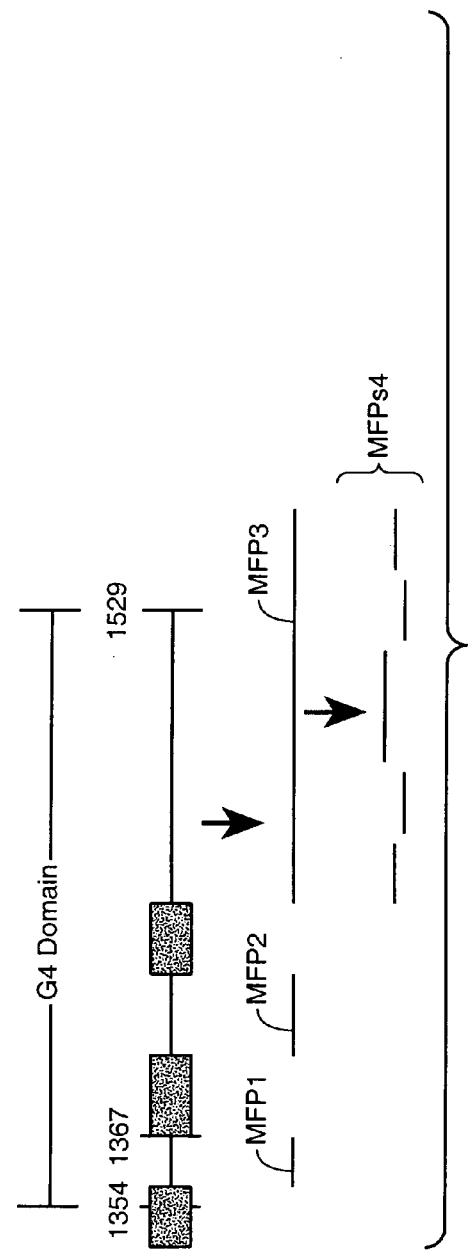

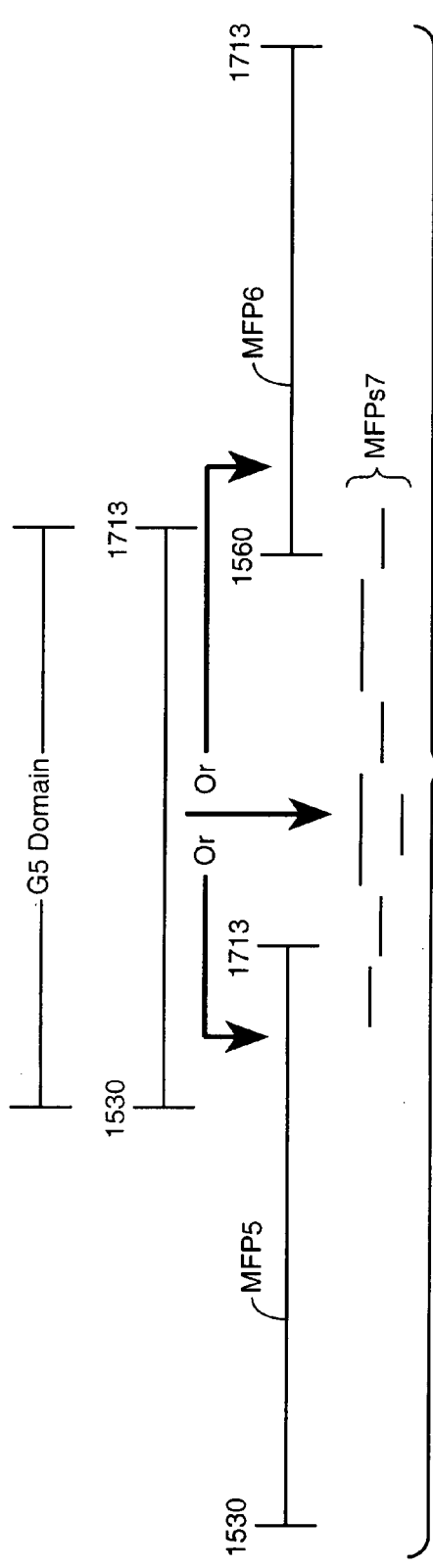
FIG._1C
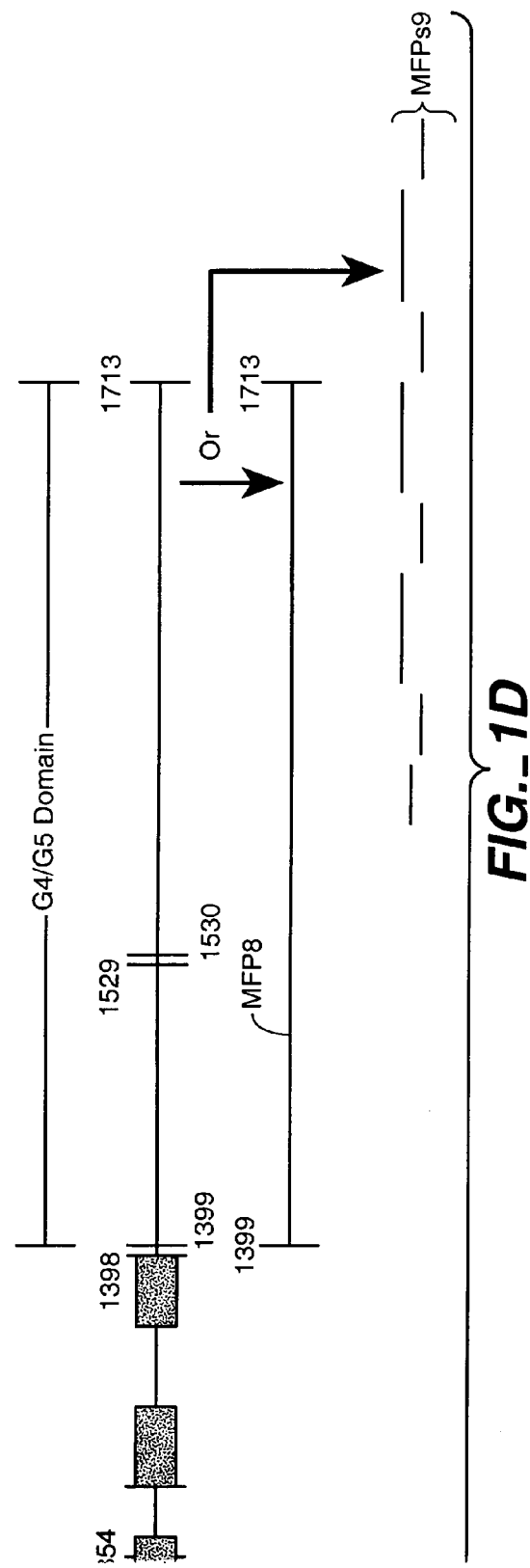
FIG._1D

FIG._2A-1

```
   1 atgggatggc tgtggatctt tggggcagcc ctggggcagt gtctgggcta cagttcacag
  61 cagcaaaggg tgccatttct tcagcctccc ggtcaaagtc aactgcaagc gagttatgtg
 121 gagtttagac ccagccaggg ttgtagccct ggatactatc gggatcataa aggcttgtat
 181 accggacggt gtgttccctg caattgcaac ggacattcaa atcaatgcca ggatggctca
 241 ggcatatgtg ttaactgtca gcacaacacc gcgggagagc actgtgaacg ctgccaggag
 301 ggctactatg caacgccgt ccacggatcc tgcagggcct gccatgtcc tcacactaac
 361 agctttgcca ctggctgtgt ggtgaatggg ggagacgtgc ggtgctcctg caaagctggg
 421 tacacaggaa cacagtgtga aggtgtgca ccgggatatt cgggaatcc cagaaattc
 481 ggaggtagct gccaaccatg cagttgtaac agcaatggcc agctgggcag ctgtcatccc
 541 ctgactggag actgcataaa ccaagaaccc aaagatagca gccctgcaga agaatgtgat
 601 gattgcgaca gctgtgtgat gaccctcctg aacgacctgg ccaccatggg cgagcagctc
 661 cgcctggtca gtctcagct gcagggcctg agtgccagcg cagggcttct ggagcagatg
 721 aggcacatgg agacccaggc caaggacctg aggaatcagt tgctcaacta ccgttctgcc
 781 atttcaaatc atggatcaaa aatagaaggc ctggaaagag aactgactga tttgaatcaa
 841 gaatttgaga ctttgcaaga aaaggctcaa gtaaattcca gaaaagcaca acattaaac
 901 aacaatgtta tcgggcaac acaaagcgca aagaactgg atgtgaagat taaaaatgtc
 961 atccggaatg tgcacattct tttaagcag atctctggga cagatggaga gggaaacaac
1021 gtgccttcag gtgactttc cagagagtgg gctgaagccc agcgcatgat gagggaactg
1081 cggaacagga actttggaaa gcacctcaga gaagcagaag ctgataaaag ggagtcgcag
1141 ctcttgctga accggataag gacctggcag aaaacccacc agggggagaa caatgggctt
1201 gctaacagta tccgggattc tttaaatgaa tacgaagcca aactcagtga ccttcgtgct
1261 cggctgcagg aggcagctgc ccaagccaag caggcaaatg gcttgaacca agaaaacgag
1321 agagctttgg gagccattca gagacaagtg aaagaaataa attccctgca gagtgatttc
1381 accaagtatc taaccactgc agactcatct ttgttgcaaa ccaacattgc gctgcagctg
1441 atggagaaaa gccagaagga atatgaaaaa ttagctgcca gtttaaatga agcaagacaa
1501 gaactaagtg acaaagtaag gaactttcc agatctgctg gcaaaacatc ccttgtggag
1561 gaggcagaaa agcacgcgcg gtccttacaa gagctggcaa agcagctgga agagatcaag
1621 agaaacgcca gcgggatga gctggtgcgc tgtgctgtgg atgccgccac cgcctacgag
1681 aacatcctca tgccatcaa agcggccgag gacgcagcca cagggctgc cagtgcatct
1741 gaatctgccc tccagacagt gataaaggaa gatctgccaa gaaaagctaa accctgagt
1801 tccaacagtg ataaactgtt aaatgaagcc aagatgacac aaaagaagct aaagcaagaa
1861 gtcagtccag ctctcaacaa cctacagcaa accctgaata ttgtgacagt tcagaaagaa
1921 gtgatagaca ccaatctcac aactctccga gatggtcttc atgggataca gagaggtgat
1981 attgatgcta tgatcagtag tgcaaagagc atggtcagaa aggccaacga catcacagat
2041 gaggttctgg atgggctcaa ccccatccag acagatgtgg aaagaattaa ggacacctat
2101 ggaggacac agaacgaaga cttcaaaaag gctctgactg atgcagataa ctcggtgaat
2161 aagttaacca caaaactacc tgatctttgg cgcaagattg aaagtatcaa ccaacagctg
2221 ttgcccttgg gaaacatctc tgacaacatg gacagaatac gagaactaat tcagcaggcc
2281 agatgctg ccagtaaggt tgctgtcccc atgaggttca atggtaaatc tggagtcgaa
2341 gtccgactgc caaatgacct ggaagatttg aaaggatata catctctgtc cttgtttctc
2401 caaaggccca actcaagaga aatgggggt actgagaata tgtttgtgat gtaccttgga
2461 aataaagatg cctcccggga ctacatcggc atggcagttg tggatggcca gctcacctgt
2521 gtctacaacc tggggaccg tgaggctgaa ctccaagtgg accagatctt gaccaagagt
2581 gagactaagg aggcagttat ggatcgggtg aaatttcaga gaatttatca gtttgcaagg
2641 cttaattaca ccaaaggagc cacatccagt aaaccagaaa cacccggagt ctatgacatg
2701 gatggtagaa atagcaatac actccttaat ttggatcctg aaaatgttgt attttatgtt
2761 ggaggttacc cacctgattt taaacttccc agtcgactaa gtttccctcc atacaaaggt
2821 tgtattgaat tagatgacct caatgaaaat gttctgagct tgtacaactt caaaaaaaca
2881 ttcaatctca acacaactga agtggagcct tgtagaagga ggaaggaaga gtcagacaaa
```

```
2941  aattattttg aaggtacggg ctatgctcga gttccaactc aaccacatgc tcccatccca
3001  acctttggac agacaattca gaccaccgtg gatagaggct tgctgttctt tgcagaaaac
3061  ggggatcgct tcatatctct aaatatagaa gatggcaagc tcatggtgag atacaaactg
3121  aattcagagc taccaaaaga gagaggagtt ggagacgcca taaacaacgg cagagaccat
3181  tcgattcaga tcaaaattgg aaaactccaa aagcgtatgt ggataaatgt ggacgttcaa
3241  aacactataa ttgatggtga agtatttgat tcagcacat  attatctggg aggaattcca
3301  attgcaatca gggaaagatt taacatttct acgcctgctt tccgaggctg catgaaaaat
3361  ttgaagaaaa ccagtggtgt cgttagattg aatgatactg tgggagtaac caaaaagtgc
3421  tcggaagact ggaagcttgt gcgatctgcc tcattctcca gaggaggaca attgagtttc
3481  actgatttgg gcttaccacc tactgaccac ctccaggcct catttggatt tcagaccttt
3541  caacccagtg gcatattatt agatcatcag acatggacaa ggaacctgca ggtcactctg
3601  gaagatggtt acattgaatt gagcaccagc gatagcggcg gcccaatttt taaatctcca
3661  cagacgtata tggatggttt actgcattat gtatctgtaa taagcgacaa ctctggacta
3721  cggcttctca tcgatgacca gcttctgaga aatagcaaaa ggctaaaaca catttcaagt
3781  tcccggcagt ctctgcgtct gggcgggagc aattttgagg gttgtattag caatgttttt
3841  gtccagaggt tatcactgag tcctgaagtc ctagatttga ccagtaactc tctcaagaga
3901  gatgtgtccc tgggaggctg cagtttaaac aaaccacctt ttctaatgtt gcttaaaggt
3961  tctaccaggt ttaacaagac caagactttt cgtatcaacc agctgttgca ggacacacca
4021  gtggcctccc caaggagcgt gaaggtgtgg caagatgctt gctcaccact tcccaagacc
4081  caggccaatc atggagccct ccagtttggg gacattccca ccagccactt gctattcaag
4141  cttcctcagg agctgctgaa acccaggtca cagtttgctg tggacatgca gacaacatcc
4201  tccagaggac tggtgtttca cacgggcact aagaactcct ttatggctct ttatctttca
4261  aaaggacgtc tggtctttgc actggggaca gatggggaaa aattgaggat caaaagcaag
4321  gagaaatgca atgatgggaa atggcacacg gtggtgtttg gccatgatgg ggaaaagggg
4381  cgcttggttg tggatggact gagggccggg gagggaagtt tgcctggaaa gtccaccatc
4441  agcatcagag cgccagttta cctgggatca cctccatcag ggaaaccaaa gagcctcccc
4501  acaaacagct tgtgggatg  cctgaagaac tttcagctgg attcaaaacc cttgtatacc
4561  ccttcttcaa gcttcggggt gtcttcctgc ttgggtggtc ctttggagaa aggcatttat
4621  ttctctgaag aaggaggtca tgtcgtcttg gctcactctg tattgttggg gccagaattt
4681  aagcttgttt tcagcatccg cccaagaagt ctcactggga tcctaataca catcggaagt
4741  cagcccggga agcacttatg tgtttacctg gaggcaggaa aggtcacggc ctctatggac
4801  agtggggcag gtgggacctc aacgtcggtc acaccaaagc agtctctgtg tgatggacag
4861  tggcactcgg tggcagtcac cataaacaa  cacatcctgc acctggaact ggacacagac
4921  agtagctaca cagctggaca gatcccctt  ccacctgcca gcactcaaga gccactacac
4981  cttggaggtg ctccagccaa tttgacgaca ctgaggatcc ctgtgtggaa atcattcttt
5041  ggctgtctga ggaatattca tgtcaatcac atccctgtcc ctgtcactga agccttggaa
5101  gtccagggc  ctgtcagtct gaatggttgt cctgaccagt aacccaagcc tatttcacag
5161  caaggaaatt caccttcaaa agcactgatt acccaatgca cctccctccc cagctcgaga
5221  tcattcttca attaggacac aaaccagaca ggtttaatag cgaatctaat tttgaattct
5281  gaccatggat acccatcact ttggcattca gtgctacatg tgtatttat  ataaaaatcc
5341  catttcttga agataaaaaa attgttattc aaattgttat gcacagaatg tttttggtaa
5401  tattaatttc cactaaaaaa ttaaatgtct ttt
```

FIG._2A-2

```
MGWLWIFGAALGQCLGYSSQQQRVPFLQPPGQSQLQASYVEFRP
SQGCSPGYYRDHKGLYTGRCVPCNCNGHSNQCQDGSGICVNCQHNTAGEHCERCQEGY
YGNAVHGSCRACPCPHTNSFATGCVVNGGDVRCSCKAGYTGTQCERCAPGYFGNPQKF
GGSCQPCSCNSNGQLGSCHPLTGDCINQEPKDSSPAEECDDCDSCVMTLLNDLATMGE
QLRLVKSQLQGLSASAGLLEQMRHMETQAKDLRNQLLNYRSAISNHGSKIEGLERELT
DLNQEFETLQEKAQVNSRKAQTLNNNVNRATQSAKELDVKIKNVIRNVHILLKQISGT
DGEGNNVPSGDFSREWAEAQRMMRELRNRNFGKHLREAEADKRESQLLLNRIRTWQKT
HQGENNGLANSIRDSLNEYEAKLSDLRARLQEAAAQAKQANGLNQENERALGAIQRQV
KEINSLQSDFTKYLTTADSSLLQTNIALQLMEKSQKEYEKLAASLNEARQELSDKVRE
LSRSAGKTSLVEEAEKHARSLQELAKQLEEIKRNASGDELVRCAVDAATAYENILNAI
KAAEDAANRAASASESALQTVIKEDLPRKAKTLSSNSDKLLNEAKMTQKKLKQEVSPA
LNNLQQTLNIVTVQKEVIDTNLTTLRDGLHGIQRGDIDAMISSAKSMVRKANDITDEV
LDGLNPIQTDVERIKDTYGRTQNEDFKKALTDADNSVNKLTNKLPDLWRKIESINQQL
LPLGNISDNMDRIRELIQQARDAASKVAVPMRFNGKSGVEVRLPNDLEDLKGYTSLSL
FLQRPNSRENGGTENMFVMYLGNKDASRDYIGMAVVDGQLTCVYNLGDREAELQVDQI
LTKSETKEAVMDRVKFQRIYQFARLNYTKGATSSKPETPGVYDMDGRNSNTLLNLDPE
NVVFYVGGYPPDFKLPSRLSFPPYKGCIELDDLNENVLSLYNFKKTFNLNTTEVEPCR
RRKEESDKNYFEGTGYARVPTQPHAPIPTFGQTIQTTVDRGLLFFAENGDRFISLNIE
DGKLMVRYKLNSELPKERGVGDAINNGRDHSIQIKIGKLQKRMWINVDVQNTIIDGEV
FDFSTYYLGGIPIAIRERFNISTPAFRGCMKNLKKTSGVVRLNDTVGVTKKCSEDWKL
VRSASFSRGGQLSFTDLGLPPTDHLQASFGFQTFQPSGILLDHQTWTRNLQVTLEDGY
IELSTSDSGGPIFKSPQTYMDGLLHYVSVISDNSGLRLLIDDQLLRNSKRLKHISSSR
QSLRLGGSNFEGCISNVFVQRLSLSPEVLDLTSNSLKRDVSLGGCSLNKPPFLMLLKG
STRFNKTKTFRINQLLQDTPVASPRSVKVWQDACSPLPKTQANHGALQFGDIPTSHLL
FKLPQELLKPRSQFAVDMQTTSSRGLVFHTGTKNSFMALYLSKGRLVFALGTDGKKLR
IKSKEKCNDGKWHTVVFGHDGEKGRLVVDGLRAREGSLPGNSTISIRAPVYLGSPPSG
KPKSLPTNSFVGCLKNFQLDSKPLYTPSSSFGVSSCLGGPLEKGIYFSEEGGHVVLAH
SVLLGPEFKLVFSIRPRSLTGILIHIGSQPGKHLCVYLEAGKVTASMDSGAGGTSTSV
TPKQSLCDGQWHSVAVTIKQHILHLELDTSSYTAGQIPFPPASTQEPLHLGGAPANL
TTLRIPVWKSFFGCLRNIHVNHIPVPVTEALEVQGPVSLNGCPDQ
```

```
   1  gcaggtccgg gaggcgcagg cggagagcgg cggtgccccc gagcccctct gcggacggct
  61  caggcgggag gaccccgcgc ggctggatgg cggcggccgc gcggcctcgg ggtcgggcac
 121  tggggccagt actgccgccg acgccgctgc tcctgctggt actgcgggtg ctgccagcct
 181  gcggggcgac cgctcgggat cccggggccg cggccgggct cagccttcac ccgacttact
 241  tcaacctggc cgaggcggcg aggatttggg ccaccgccac ctgcggggag aggggacccg
 301  gcgaggggag gccccagccc gagctctact gcaagttggt cgggggcccc accgcccag
 361  gcagcggcca caccatccag ggccagttct gtgactattg caattctgaa gaccccagga
 421  aagcacatcc tgtcaccaat gccatcgatg gatctgaacg ttggtggcaa agccctcccc
 481  tgtcctcagg cacacagtac aacagagtca acctcacctt ggatctgggg cagctcttcc
 541  atgtggccta tattttaatc aaatttgcaa attctcctcg ccctgatctt tgggtcttgg
 601  aaagatctgt agactttgga agcacctact caccatggca atattttgct cattctaaag
 661  tagactgttt aaaagaattt gggcgggagg caaatatggc tgtcacccgg gatgatgatg
 721  tactttgtgt tactgaatat tcccgtattg tacctttgga aaatggtgag gttgtggtgt
 781  ccttgataaa cggtcgtcca ggtgcaaaaa attttacttt ctctcacacc ctgagggagt
 841  ttaccaaggc aacaaacatc cgcttgcgtt ttcttagaac caatacgctt cttggacacc
 901  tcatctccaa agcccagcga gatccaactg tcactcggcg gtattattac agcataaagg
 961  acatcagcat tggtgggcag tgtgtttgca atggccatgc tgaagtgtgc aatataaaca
1021  atcctgaaaa actgtttcgg tgtgaatgcc agcaccacac ctgtggggag acgtgtgatc
1081  gctgctgcac agggtacaat cagaggcgct ggcggcccgc cgcttgggag cagagccacg
1141  agtgtgaagc atgcaactgc cacggccatg ccagcaactg ttactatgat ccagatgttg
1201  agcggcagca ggcaagcttg aatacccagg gcatctatgc tggtggaggg gtctgcatta
1261  actgtcagca caacacagct ggagtaaact gtgaacagtg tgctaagggc tattaccgcc
1321  cttatggggt tccagtggat gcccctgatg gctgcatccc ctgcagctgt gaccctgagc
1381  atgcggatgg ctgtgaacag ggttcaggcc gctgtcactg caagccaaat ttccacggag
1441  acaactgtga gaagtgtgca attggatact acaatttccc attttgcttg agaattccca
1501  ttttttcctgt ttctacacca agttcagaag atccagtagc tggagatata aaagggtgtg
1561  actgtaatct ggaaggtgtt ctccctgaaa tatgtgatgc ccacggacgg tgcctgtgcc
1621  gccctggggt tgagggccct cgatgtgata cctgccgctc tggtttctac tcattcccta
1681  tttgccaagc ctgctggtgt tcagcccttg gatcctacca gatgccctgc agctcagtga
1741  ctggacagtg tgaatgtcgg ccaggagtta caggacagcg gtgtgacagg tgtctctcag
1801  gagcttatga tttcccccac tgccaaggtt ccagcagtgc ttgtgaccca gctggtacca
1861  tcaactccaa tttggggtat tgccaatgca gcttcatgt tgaaggtcct acttgtagcc
1921  gctgcaaact gttatattgg aatctggaca agaaaaaccc cagtggatgt tcagaatgca
1981  agtgccataa ggcgggaaca gtgagtggaa ctggagagtg taggcaggga gatggtgact
2041  gtcactgcaa gtcccatgtg ggtggcgatt cctgcgacac ctgtgaagat ggatattttg
2101  ctttggaaaa gagcaattac tttgggtgtc aagggtgtca gtgtgacatt ggtgggggcat
2161  tgtcctccat gtgcagtggg ccctcgggag tgtgccagtg ccgagagcat gtcgtgggaa
2221  aggtgtgcca gcggcctgaa acaactact atttcccaga tttgcatcat atgaagtatg
2281  agattgaaga cggcagcaca cctaatggga gagaccttcg atttggattt gatccgctgg
2341  catttcctga gtttagctgg agaggatatg cccaaatgac ctcagtacag aatgatgtaa
2401  gaataacatt gaatgtaggg aagtcaagtg gctccttgtt tcgtgttatt ctgagatacg
2461  ttaaccctgg aactgaagca gtatctggcc atataactat ttatccatcc tggggtgctg
2521  ctcaaagcaa agagatcatc ttcctgccga gtaaggagcc agcctttgtc actgtccctg
2581  gaaatggttt tgcagaccca ttttcaatca caccaggaat atgggttgct tgtattaagg
2641  cagaaggagt ccttctggat tacctggtgc tgctccccag ggactactat gaagcctctg
2701  tactgcagct gccagtcaca gaaccatgtg cctacgcagg acctccccaa gaaaattgct
2761  tactctacca gcatttgcca gtgaccagat tcccctgtac cctggcttgt gaggccagac
2821  acttcctgct tgatggggag ccaagacccg tggcagtgag gcagcccaca cctgcacacc
2881  ctgtcatggt ggacctcagc gggagagagg tggaattgca tctgcggctg cgcatcccac
```

FIG. 2C-2

```
2941 aggttggcca ctacgtggtt gtggtcgagt attccacgga ggcagctcag ctgtttgtgg
3001 ttgatgtgaa tgtgaagagc tccgggtctg ttctggcagg ccaggtgaac atttacagct
3061 gcaactacag tgttctctgc cggagtgctg tgattgatca catgagccgc atcgccatgt
3121 atgagctatt ggcagatgca gacattcagc tcaagggaca catggcccga ttccttctgc
3181 atcaagtttg tatcatacct attgaagaat tctcagctga gtatgtgaga ccacaagtcc
3241 actgcattgc cagttatggg cgatttgtca atcaaagtgc cacctgtgtc tccttggccc
3301 atgaaactcc tccaacagca ttaattttgg atgttctaag tggcaggcct ttccctcacc
3361 tgccccagca gtcgtcacct tctgttgatg ttcttcctgg ggtcaccttg aaggcaccgc
3421 agaatcaagt gaccctgaga ggacgtgtac cacacctggg ccgatacgtc tttgtcatcc
3481 attttacca agcagcgcac ccgacgtttc ccgcgcaggt gtcggtggat ggcgggtggc
3541 cacgggcagg ctccttccat gcctcttttt gccccatgt gcttggctgc cgggatcaag
3601 tgattgccga aggccagatt gagtttgaca tctcagagcc tgaagtggcc gcaactgtga
3661 aggttccaga aggaaagtcc ttggttttgg tccgtgttct agtggtgcct gcagaaaact
3721 atgactacca aatacttcac aaaaaatcca tggacaagtc actcgagttt atcaccaatt
3781 gtggaaaaaa cagcttttac cttgaccccc agacagcctc cagattctgt aagaattccg
3841 ccaggtccct ggtggccttt taccacaagg gcgccctgcc ttgtgagtgc caccccactg
3901 gggccaccgg ccctcactgc agccctgagg gtgggcagtg cccatgccag cccaacgtca
3961 tcgggcggca gtgcacccgc tgtgcaacag gccactacgg attcccacgc tgcaagccgt
4021 gcagctgtgg tcggcgcctt tgtgaagaga tgacggggca gtgccgctgc cctccccgca
4081 cggtcaggcc ccagtgtgag gtgtgtgaga cacactcatt cagcttccac cccatggccg
4141 gctgcgaagg ctgcaactgt tccaggaggg gcaccatcga ggctgccatg ccggagtgtg
4201 accgggacag cgggcagtgc agatgcaagc ccagaatcac agggcggcag tgtgaccgat
4261 gtgcttccgg gttttaccgc tttcctgagt gtgttccctg caattgcaac agagatggga
4321 ctgagccagg agtgtgtgac ccagggaccg ggcttgcct ctgcaaggaa atgtagaag
4381 gcacagagtg taatgtgtgt cgagaaggct cattccattt ggacccagcc aatctcaagg
4441 gttgtaccag ctgtttctgt tttggagtaa ataatcaatg tcacagctca cataagcgaa
4501 ggactaagtt tgtggatatg ctgggctggc acctggagac agcagacaga gtggacatcc
4561 ctgtctcttt caacccaggc agcaacagta tggtggcgga tctccaggag ctgccgcaa
4621 ccatccacag cgcgtcctgg gtcgcaccca cctcctacct ggggacaag gtttcttcat
4681 atggtggtta cctcacttac aagccaagt cctttggctt gcctggcgac atggttcttc
4741 tggaaaagaa gccggatgta cagctcactg gtcagcacat gtccatcatc tatgaggaga
4801 caaacacccc acggccagac cggctgcatc atggacgagt gcacgtggtc gagggaaact
4861 tcagacatgc cagcagccgt gcccagtgt ctaggagga gctgatgaca gtgctgtcta
4921 gactggcaga tgtgcgcatc caaggcctct acttcacaga gactcaaagg ctcaccctga
4981 gcgaggtggg gctagaggaa gcctctgaca caggaagtgg gcgcatagca cttgctgtgg
5041 aaatctgtgc ctgccccct gcctacgctg tgactcttg tcagggttgt agccctggat
5101 actatcggga tcataaaggc ttgtataccg gacggtgtgt tccctgcaat tgcaacggac
5161 attcaaatca atgccaggat ggctcaggca tatgtgttaa ctgtcagcac aacaccgcgg
5221 gagagcactg tgaacgctgc caggagggct actatggcaa cgccgtccac ggatcctgca
5281 gggcctgccc atgtcctcac actaacagct ttgccactgg ctgtgtggtg aatggggag
5341 acgtgcggtg ctcctgcaaa gctgggtaca caggaacaca gtgtgaaagg tgtgcaccgg
5401 gatatttcgg gaatcccag aaattcggag gtagctgcca accatgcagt gtaacagca
5461 atggccagct gggcagctgt atcccctga ctggagactg cataaaccaa gaacccaaag
5521 atagcagccc tgcagaagaa tgtgatgatt gcgacagctg tgtgatgacc ctcctgaacg
5581 acctggccac catgggcgag cagctccgcc tggtcaagtc tcagctgcag ggcctgagtg
5641 ccagcgcagg gcttctggag cagatgaggc acatggagac ccaggccaag gacctgagga
5701 atcagttgct caactaccgt tctgccattt caaatcatgg atcaaaaata gaaggcctgg
5761 aaagagaact gactgatttg aatcaagaat ttgagacttt gcaagaaaag gctcaagtaa
5821 attccagaaa agcacaaaca ttaaacaaca atgttaatcg ggcaacacaa agcgcaaaag
```

FIG. 2C-3

```
5881  aactggatgt gaagattaaa aatgtcatcc ggaatgtgca cattcttta aagcagatct
5941  ctgggacaga tggagaggga acaacgtgc cttcaggtga cttttccaga gagtgggctg
6001  aagcccagcg catgatgagg gaactgcgga acaggaactt tggaaagcac ctcagagaag
6061  cagaagctga taaaagggag tcgcagctct tgctgaaccg gataaggacc tggcagaaaa
6121  cccaccaggg ggagaacaat gggcttgcta acagtatccg ggattcttta aatgaatacg
6181  aagccaaact cagtgacctt cgtgctcggc tgcaggaggc agctgcccaa gccaagcagg
6241  caaatggctt gaaccaagaa acgagagag ctttgggagc cattcagaga caagtgaaag
6301  aaataaattc cctgcagagt gatttcacca agtatctaac cactgcagac tcatctttgt
6361  tgcaaaccaa cattgcgctg cagctgatgg agaaaagcca gaaggaatat gaaaaattag
6421  ctgccagttt aaatgaagca agacaagaac taagtgacaa agtaagagaa ctttccagat
6481  ctgctggcaa aacatccctt gtggaggagg cagaaaagca cgcgcggtcc ttacaagagc
6541  tggcaaagca gctggaagag atcaagagaa acgccagcgg ggatgagctg gtgcgctgtg
6601  ctgtggatgc cgccaccgcc tacgagaaca tcctcaatgc catcaaagcg gccgaggacg
6661  cagccaacag ggctgccagt gcatctgaat ctgccctcca gacagtgata aggaagatc
6721  tgccaagaaa agctaaaacc ctgagttcca acagtgataa actgttaaat gaagccaaga
6781  tgacacaaaa gaagctaaag caagaagtca gtccagctct caacaaccta cagcaaaccc
6841  tgaatattgt gacagttcag aaagaagtga tagacaccaa tctcacaact ctccgagatg
6901  gtcttcatgg gatacagaga ggtgatattg atgctatgat cagtagtgca aagagcatgg
6961  tcagaaaggc caacgacatc acagatgagg ttctggatgg gctcaacccc atccagacag
7021  atgtggaaag aattaaggac acctatggga ggacacagaa cgaagacttc aaaaaggctc
7081  tgactgatgc agataactcg gtgaataagt taaccaacaa actacctgat ctttggcgca
7141  agattgaaag tatcaaccaa cagctgttgc ccttgggaaa catctctgac aacatggaca
7201  gaatacgaga actaattcag caggccagag atgctgccag taaggttgct gtccccatga
7261  ggttcaatgg taaatctgga gtcgaagtcc gactgccaaa tgacctggaa gatttgaaag
7321  gatatacatc tctgtccttg tttctccaaa ggcccaactc aagagaaaat gggggtactg
7381  agaatatgtt tgtgatgtac cttggaaata aagatgcctc ccgggactac atcggcatgg
7441  cagttgtgga tggccagctc acctgtgtct acaacctggg ggaccgtgag gctgaactcc
7501  aagtggacca gatcttgacc aagagtgaga ctaaggaggc agttatggat cgggtgaaat
7561  ttcagagaat ttatcagttt gcaaggctta attacaccaa aggagccaca tccagtaaac
7621  cagaaacacc cggagtctat gacatggatg gtagaaatag caatacactc cttaatttgg
7681  atcctgaaaa tgttgtattt tatgttggag gttacccacc tgattttaaa cttcccagtc
7741  gactaagttt ccctccatac aaaggttgta ttgaattaga tgacctcaat gaaaatgttc
7801  tgagcttgta caacttcaaa aaaacattca atctcaacac aactgaagtg gagccttgta
7861  gaaggaggaa ggaagagtca gacaaaaatt atttttgaagg tacgggctat gctcgagttc
7921  caactcaacc acatgctccc atcccaacct tggacagac aattcagacc accgtggata
7981  gaggcttgct gttctttgca gaaaacgggg atcgcttcat atctctaaat atagaagatg
8041  gcaagctcat ggtgagatac aaactgaatt cagagctacc aaaagagaga ggagttggag
8101  acgccataaa caacggcaga gaccattcga ttcagatcaa aattggaaaa ctccaaaagc
8161  gtatgtggat aaatgtggac gttcaaaaca ctataattga tggtgaagta tttgatttca
8221  gcacatatta tctggaggga attccaattg caatcaggga aagatttaac atttctacgc
8281  ctgctttccg aggctgcatg aaaaatttga agaaaccag tggtgtcgtt agattgaatg
8341  atactgtggg agtaaccaaa aagtgctcgg aagactggaa gcttgtgcga tctgcctcat
8401  tctccagagg aggacaattg agtttcactg atttgggctt accacctact gaccacctcc
8461  aggcctcatt tggattcag acctcaac ccagtggcat attattgat catcagacat
8521  ggacaaggaa cctgcaggtc actctggaag atggttacat tgaattgagc accagcgata
8581  gcggcagccc aattttaaa tctccacaga cgtatatgga tggttactg cattatgtat
8641  ctgtaataag cgacaactct ggactacggc ttctcatcga tgaccagctt ctgagaaata
8701  gcaaaaggct aaaacacatt tcaagttccc ggcagtctct gcgtctgggc gggagcaatt
8761  ttgagggttg tattagcaat gttttgtcc agaggttatc actgagtcct gaagtcctag
```

```
8821  atttgaccag taactctctc aagagagatg tgtccctggg aggctgcagt ttaaacaaac
8881  cacctttct  aatgttgctt aaaggttcta ccaggtttaa caagaccaag acttttcgta
8941  tcaaccagct gttgcaggac acaccagtgg cctcccaag  gagcgtgaag gtgtggcaag
9001  atgcttgctc accacttccc aagacccagg ccaatcatgg agccctccag tttggggaca
9061  ttcccaccag ccacttgcta ttcaagcttc ctcaggagct gctgaaaccc aggtcacagt
9121  ttgctgtgga catgcagaca acatcctcca gaggactggt gtttcacacg ggcactaaga
9181  actcctttat ggctctttat ctttcaaaag gacgtctggt ctttgcactg gggacagatg
9241  ggaaaaaatt gaggatcaaa agcaaggaga aatgcaatga tgggaaatgg cacacggtgg
9301  tgtttggcca tgatggggaa aagggcgct  tggttgtgga tggactgagg gcccgggagg
9361  gaagtttgcc tggaaactcc accatcagca tcagagcgcc agtttacctg ggatcacctc
9421  catcagggaa accaaagagc ctccccacaa acagctttgt gggatgcctg aagaactttc
9481  agctggattc aaaacccttg tatacccctt cttcaagctt cggggtgtct tcctgcttgg
9541  gtggtccttt ggagaaaggc atttatttct ctgaagaagg aggtcatgtc gtcttggctc
9601  actctgtatt gttggggcca gaatttaagc ttgttttcag catccgccca agaagtctca
9661  ctgggatcct aatacacatc ggaagtcagc ccgggaagca cttatgtgtt tacctggagg
9721  caggaaaggt cacggcctct atggacagtg gggcaggtgg gacctcaacg tcggtcacac
9781  caaagcagtc tctgtgtgat ggacagtggc actcggtggc agtcaccata aaacaacaca
9841  tcctgcacct ggaactggac acagacagta gctacacagc tggacagatc cccttcccac
9901  ctgccagcac tcaagagcca ctacaccttg gaggtgctcc agccaatttg acgacactga
9961  ggatccctgt gtggaaatca ttctttggct gtctgaggaa tattcatgtc aatcacatcc
10021 ctgtccctgt cactgaagcc ttggaagtcc aggggcctgt cagtctgaat ggttgtcctg
10081 accagtaacc caagcctatt tcacagcaag gaaattcacc ttcaaaagca ctgattaccc
10141 aatgcacctc cctccccagc tcgagatcat tcttcactca ggacacaaac cagacaggtt
10201 taatagcgaa tctaattttg aattctgacc atggataccc atcactttgg cattcagtgc
10261 tacatgtgta ttttatataa aaatcccatt tcttgaagat aaaaaaattg ttattcaaat
10321 tgttatgcac agaatgtttt tggtaatatt aatttccact aaaaaattaa atgtctttta
10381 agaaacattc ttttccactt gttaaaaaaa ttaaatatat tttaaagcac tttaagaata
10441 tgaaactttc atatatgtta aaggattata atttatggaa ttaaaaaatg cagtgtagtc
10501 cttaaaaaaa a
```

MAAAARPRGRALGPVLPPTPLLLLVLRVLPACGATARDPGAAAG
LSLHPTYFNLAEAARIWATATCGERGPGEGRPQPELYCKLVGGPTAPGSGHTIQGQFC
DYCNSEDPRKAHPVTNAIDGSERWWQSPPLSSGTQYNRVNLTLDLGQLFHVAYILIKF
ANSPRPDLWVLERSVDFGSTYSPWQYFAHSKVDCLKEFGREANMAVTRDDDVLCVTEY
SRIVPLENGEVVVSLINGRPGAKNFTFSHTLREFTKATNIRLRFLRTNTLLGHLISKA
QRDPTVTRRYYYSIKDISIGGQCVCNGHAEVCNINNPEKLFRCECQHHTCGETCDRCC
TGYNQRRWRPAAWEQSHECEACNCHGHASNCYYDPDVERQQASLNTQGIYAGGGVCIN
CQHNTAGVNCEQCAKGYYRPYGVPVDAPDGCIPCSCDPEHADGCEQGSGRCHCKPNFH
GDNCEKCAIGYYNFPFCLRIPIFPVSTPSSEDPVAGDIKGCDCNLEGVLPEICDAHGR
CLCRPGVEGPRCDTCRSGFYSFPICQACWCSALGSYQMPCSSVTGQCECRPVTGQRC
DRCLSGAYDFPHCQGSSSACDPAGTINSNLGYCQCKLHVEGPTCSRCKLLYWNLDKEN
PSGCSECKCHKAGTVSGTGECRQGDGDCHCKSHVGGDSCDTCEDGYFALEKSNYFGCQ
GCQCDIGGALSSMCSGPSGVCQCREHVVGKVCQRPENNYYFPDLHHMKYEIEDGSTPN
GRDLRFGFDPLAFPEFSWRGYAQMTSVQNDVRITLNVGKSSGSLFRVILRYVNPGTEA
VSGHITIYPSWGAAQSKEIIFLPSKEPAFVTVPGNGFADPFSITPGIWVACIKAEGVL
LDYLVLLPRDYYEASVLQLPVTEPCAYAGPPQENCLLYQHLPVTRFPCTLACEARHFL
LDGEPRPVAVRQPTPAHPVMVDLSGREVELHLRLRIPQVGHYVVVVEYSTEAAQLFVV
DVNVKSSGSVLAGQVNIYSCNYSVLCRSAVIDHMSRIAMYELLADADIQLKGHMARFL
LHQVCIIPIEEFSAEYVRPQVHCIASYGRFVNQSATCVSLAHETPPTALILDVLSGRP
FPHLPQQSSPSVDVLPGVTLKAPQNQVTLRGRVPHLGRYVFVIHFYQAAHPTFPAQVS
VDGGWPRAGSFHASFCPHVLGCRDQVIAEGQIEFDISEPEVAATVKVPEGKSLVLVRV
LVVPAENYDYQILHKKSMDKSLEFITNCGKNSFYLDPQTASRFCKNSARSLVAFYHKG
ALPCECHPTGATGPHCSPEGGQCPCQPNVIGRQCTRCATGHYGFPRCKPCSCGRRLCE
EMTGQCRCPPRTVRPQCEVCETHSFSFHPMAGCEGCNCSRRGTIEAAMPECDRDSGQC
RCKPRITGRQCDRCASGFYRFPECVPCNCNRDGTEPGVCDPGTGACLCKENVEGTECN
VCREGSFHLDPANLKGCTSCFCFGVNNQCHSSHKRRTKFVDMLGWHLETADRVDIPVS
FNPGSNSMVADLQELPATIHSASWVAPTSYLGDKVSSYGGYLTYQAKSFGLPGDMVLL
EKKPDVQLTGQHMSIIYEETNTPRPDRLHHGRVHVVEGNFRHASSRAPVSREELMTVL
SRLADVRIQGLYFTETQRLTLSEVGLEEASDTGSGRIALAVEICACPPAYAGDSCQGC
SPGYYRDHKGLYTGRCVPCNCNGHSNQCQDGSGICVNCQHNTAGEHCERCQEGYYGNA
VHGSCRACPCPHTNSFATGCVVNGGDVRCSCKAGYTGTQCERCAPGYFGNPQKFGGSC
QPCSCNSNGQLGSCHPLTGDCINQEPKDSSPAEECDDCDSCVMTLLNDLATMGEQLRL
VKSQLQGLSASAGLLEQMRHMETQAKDLRNQLLNYRSAISNHGSKIEGLERELTDLNQ
EFETLQEKAQVNSRKAQTLNNNVNRATQSAKELDVKIKNVIRNVHILLKQISGTDGEG
NNVPSGDFSREWAEAQRMMRELRNRNFGKHLREAEADKRESQLLLNRIRTWQKTHQGE
NNGLANSIRDSLNEYEAKLSDLRARLQEAAAQAKQANGLNQENERALGAIQRQVKEIN
SLQSDFTKYLTTADSSLLQTNIALQLMEKSQKEYEKLAASLNEARQELSDKVRELSRS
AGKTSLVEEAEKHARSLQELAKQLEEIKRNASGDELVRCAVDAATAYENILNAIKAAE
DAANRAASASESALQTVIKEDLPRKAKTLSSNSDKLLNEAKMTQKKLKQEVSPALNNL
QQTLNIVTVQKEVIDTNLTTLRDGLHGIQRGDIDAMISSAKSMVRKANDITDEVLDGL
NPIQTDVERIKDTYGRTQNEDFKKALTDADNSVNKLTNKLPDLWRKIESINQQLLPLG
NISDNMDRIRELIQQARDAASKVAVPMRFNGKSGVEVRLPNDLEDLKGYTSLSLFLQR
PNSRENGGTENMFVMYLGNKDASRDYIGMAVVDGQLTCVYNLGDREAELQVDQILTKS
ETKEAVMDRVKFQRIYQFARLNYTKGATSSKPETPGVYDMDGRNSNTLLNLDPENVVF

```
YVGGYPPDFKLPSRLSFPPYKGCIELDDLNENVLSLYNFKKTFNLNTTEVEPCRRRKE
ESDKNYFEGTGYARVPTQPHAPIPTFGQTIQTTVDRGLLFFAENGDRFISLNIEDGKL
MVRYKLNSELPKERGVGDAINNGRDHSIQIKIGKLQKRMWINVDVQNTIIDGEVFDFS
TYYLGGIPIAIRERFNISTPAFRGCMKNLKKTSGVVRLNDTVGVTKKCSEDWKLVRSA
SFSRGGQLSFTDLGLPPTDHLQASFGFQTFQPSGILLDHQTWTRNLQVTLEDGYIELS
TSDSGSPIFKSPQTYMDGLLHYVSVISDNSGLRLLIDDQLLRNSKRLKHISSSRQSLR
LGGSNFEGCISNVFVQRLSLSPEVLDLTSNSLKRDVSLGGCSLNKPPFLMLLKGSTRF
NKTKTFRINQLLQDTPVASPRSVKVWQDACSPLPKTQANHGALQFGDIPTSHLLFKLP
QELLKPRSQFAVDMQTTSSRGLVFHTGTKNSFMALYLSKGRLVFALGTDGKKLRIKSK
EKCNDGKWHTVVFGHDGEKGRLVVDGLRAREGSLPGNSTISIRAPVYLGSPPSGKPKS
LPTNSFVGCLKNFQLDSKPLYTPSSSFGVSSCLGGPLEKGIYFSEEGGHVVLAHSVLL
GPEFKLVFSIRPRSLTGILIHIGSQPGKHLCVYLEAGKVTASMDSGAGGTSTSVTPKQ
SLCDGQWHSVAVTIKQHILHLELDTDSSYTAGQIPFPPASTQEPLHLGGAPANLTTLR
IPVWKSFFGCLRNIHVNHIPVPVTEALEVQGPVSLNGCPDQ"
```

FIG._2D-2

```
   1 gggatgcctc cagcagtgag gcggtcagcc tgcagcatgg gatggctgtg gatctttggg
  61 gcagccctgg ggcagtgtct gggctacagt tcacagcagc aaagggtgcc atttcttcag
 121 cctcccggtc aaagtcaact gcaagcgagt tatgtggagt ttagacccag ccagggttgt
 181 agccctggat actatcggga tcataaaggc ttgtataccg gacggtgtgt tccctgcaat
 241 tgcaacggac attcaaatca atgccaggat ggctcaggca tatgtgttaa ctgtcagcac
 301 aacaccgcgg gagagcactg tgaacgctgc caggagggct actatggcaa cgccgtccac
 361 ggatcctgca gggcctgccc atgtcctcac actaacagct tgccactgg ctgtgtggtg
 421 aatgggggag acgtgcggtg ctcctgcaaa gctgggtaca caggaacaca gtgtgaaagg
 481 tgtgcaccgg gatatttcgg gaatcccag aaattcggag gtagctgcca accatgcagt
 541 tgtaacagca atggccagct gggcagctgt catccctga ctggagactg cataaaccaa
 601 gaacccaaag atagcagccc tgcagaagaa tgtgatgatt gcgacagctg tgtgatgacc
 661 ctcctgaacg acctggccac catgggcgag cagctccgcc tggtcaagtc tcagctgcag
 721 ggcctgagtg ccagcgcagg gcttctggag cagatgaggc acatggagac ccaggccaag
 781 gacctgagga atcagttgct caactaccgt tctgccattt caaatcatgg atcaaaaata
 841 gaaggcctgg aaagagaact gactgatttg aatcaagaat ttgagacttt gcaagaaaag
 901 gctcaagtaa attccagaaa agcacaaaca ttaaacaaca atgttaatcg ggcaacacaa
 961 agcgcaaaag aactggatgt gaagattaaa aatgtcatcc ggaatgtgca cattcttta
1021 aagcagatct ctgggacaga tggagaggga acaacgtgc cttcaggtga cttttccaga
1081 gagtgggctg aagcccagcg catgatgagg gaactgcgga acaggaactt tggaaagcac
1141 ctcagagaag cagaagctga taaaggggag tcgcagctct tgctgaaccg gataaggacc
1201 tggcagaaaa cccaccaggg ggagaacaat gggcttgcta acagtatccg ggattcttta
1261 aatgaatacg aagccaaact cagtgacctt cgtgctcggc tgcaggaggc agctgcccaa
1321 gccaagcagg caaatggctt gaaccaagaa aacgagagag ctttgggagc cattcagaga
1381 caagtgaaag aaataaattc cctgcagagt gatttcacca agtatctaac cactgcagac
1441 tcatctttgt tgcaaaccaa cattgcgctg cagctgatgg agaaaagcca gaggaatat
1501 gaaaaattag ctgccagttt aaatgaagca agacaagaac taagtgacaa agtaagagaa
1561 ctttccagat ctgctggcaa aacatccctt gtggaggagg cagaaaagca cgcgcggtcc
1621 ttacaagagc tggcaaagca gctggaagag atcaagagaa acgccagcgg ggatgagctg
1681 gtgcgctgtg ctgtggatgc cgccaccgcc tacgagaaca tcctcaatgc catcaaagcg
1741 gccgaggacg cagccaacag ggctgccagt gcatctgaat ctgccctcca gacagtgata
1801 aaggaagatc tgccaagaaa agctaaaacc ctgagttcca acagtgataa actgttaaat
1861 gaagccaaga tgacacaaaa gaagctaaag caagaagtca gtccagctct caacaaccta
1921 cagcaaaccc tgaatattgt gacagttcag aaagaagtga tagacaccaa tctcacaact
1981 ctccagatgt gtcttcatgg gatacagaga ggtgatattg atgctatgat cagtagtgca
2041 aagagcatgg tcagaaaggc caacgacatc acagatgagg ttctggatgg gctcaacccc
2101 atccagacag atgtggaaag aattaaggac acctatggga ggacacagaa cgaagacttc
2161 aaaaaggctc tgactgatgc agataactcg gtgaataagt taaccaacaa actacctgat
2221 ctttggcgca agattgaaag tatcaaccaa cagctgttgc ccttgggaaa catctctgac
2281 aacatggaca gaatacgaga actaattcag caggccagag atgctgccag taaggttgct
2341 gtccccatga ggttcaatgg taaatctgga gtcgaagtcc gactgccaaa tgacctggaa
2401 gatttgaaag gatatacatc tctgtccttg tttctccaaa ggcccaactc aagagaaaat
2461 gggggtactg agaatatgtt tgtgatgtac cttggaaata agatgcctc ccgggactac
2521 atcggcatgg cagttgtgga tggccagctc acctgtgtct acaacctggg ggaccgtgag
2581 gctgaactcc aagtggacca gatcttgacc aagagtgaga ctaaggaggc agttatggat
2641 cgggtgaaat tcagagaat ttatcagttt gcaaggctta attacaccaa aggagccaca
2701 tccagtaaac cagaaacacc cggagtctat gacatggatg gtagaaatag caatacactc
2761 cttaatttgg atcctgaaaa tgttgtattt tatgttggag gttacccacc tgatttaaa
2821 cttcccagtc gactaagttt ccctccatac aaaggttgta ttgaattaga tgacctcaat
```

FIG. 2E-1

```
2881  gaaaatgttc tgagcttgta caacttcaaa aaaacattca atctcaacac aactgaagtg
2941  gagccttgta gaaggaggaa ggaagagtca gacaaaaatt attttgaagg tacgggctat
3001  gctcgagttc caactcaacc acatgctccc atcccaacct tggacagac aattcagacc
3061  accgtggata gaggcttgct gttctttgca gaaaacgggg atcgcttcat atctctaaat
3121  atagaagatg gcaagctcat ggtgagatac aaactgaatt cagagctacc aaaagagaga
3181  ggagttggag acgccataaa caacggcaga gaccattcga ttcagatcaa aattggaaaa
3241  ctccaaaagc gtatgtggat aaatgtggac gttcaaaaca ctataattga tggtgaagta
3301  tttgatttca gcacatatta tctggagga attccaattg caatcaggga agatttaac
3361  atttctacgc ctgctttccg aggctgcatg aaaaatttga agaaaaccag tggtgtcgtt
3421  agattgaatg atactgtggg agtaaccaaa aagtgctcgg aagactggaa gcttgtgcga
3481  tctgcctcat tctccagagg aggacaattg agtttcactg atttgggctt accacctact
3541  gaccacctcc aggcctcatt tggatttcag acctttcaac ccagtggcat attattagat
3601  catcagacat ggacaaggaa cctgcaggtc actctggaag atggttacat tgaattgagc
3661  accagcgata gcggcagccc aattttttaaa tctccacaga cgtatatgga tggtttactg
3721  cattatgtat ctgtaataag cgacaactct ggactacggc ttctcatcga tgaccagctt
3781  ctgagaaata gcaaaaggct aaaacacatt tcaagttccc ggcagtctct gcgtctgggc
3841  gggagcaatt tgagggttg tattagcaat gtttttgtcc agaggttatc actgagtcct
3901  gaagtcctag atttgaccag taactctctc aagagagatg tgtccctggg aggctgcagt
3961  ttaaacaaac cacctttcct aatgttgctt aaaggttcta ccaggtttaa caagaccaag
4021  acttttcgta tcaaccagct gttgcaggac acaccagtgg cctccccaag gagcgtgaag
4081  gtgtggcaag atgcttgctc accacttccc aagacccagg ccaatcatgg agccctccag
4141  tttggggaca ttcccaccag ccacttgcta ttcaagcttc ctcaggagct gctgaaaccc
4201  aggtcacagt tgctgtgga catgcagaca acatcctcca gaggactggt gtttcacacg
4261  ggcactaaga actccttat ggctctttat cttcaaaag gacgtctggt cttttgcactg
4321  gggacagatg ggaaaaaatt gaggatcaaa agcaaggaga atgcaatga tgggaaatgg
4381  cacacggtgg tgtttggcca tgatggggaa aaggggcgct tggttgtgga tggactgagg
4441  gcccggagg gaagtttgcc tggaaactcc accatcagca tcagagcgcc agtttacctg
4501  ggatcacctc catcagggaa accaaagagc ctccccacaa acagctttgt gggatgcctg
4561  aagaactttc agctggattc aaaacccttg tatacccctt cttcaagctt cggggtgtct
4621  tcctgcttgg gtggtccttt ggagaaaggc atttatttct ctgaagaagg aggtcatgtc
4681  gtcttggctc actctgtatt gttggggcca gaatttaagc ttgttttcag catccgccca
4741  agaagtctca ctgggatcct aatacacatc ggaagtcagc ccgggaagca cttatgtgtt
4801  tacctggagg caggaaaggt cacggcctct atggacagtg gggcaggtgg gacctcaacg
4861  tcggtcacac caaagcagtc tctgtgtgat ggacagtggc actcggtggc agtcaccata
4921  aaacaacaca tcctgcacct ggaactggac acagacagta gctacacagc tggacagatc
4981  cccttcccac ctgccagcac tcaagagcca ctacaccttg gaggtgctcc agccaatttg
5041  acgacactga ggatccctgt gtggaaatca ttctttggct gtctgaggaa tattcatgtc
5101  aatcacatcc ctgtccctgt cactgaagcc ttggaagtcc aggggcctgt cagtctgaat
5161  ggttgtcctg accagtaacc caagccatt tcacagcaag gaaattcacc ttcaaaagca
5221  ctgattaccc aatgcacctc cctccccagc tcgagatcat tcttcactca ggacacaaac
5281  cagacaggtt aatagcgaa tctaattttg aattctgacc atggataccc atcactttgg
5341  cattcagtgc tacatgtgta ttttatataa aaatcccatt tcttgaagat aaaaaaattg
5401  ttattcaaat tgttatgcac agaatgtttt tggtaatatt aatttccact aaaaaattaa
5461  atgtctttta agaaacattc ttttccactt gttaaaaaaa ttaaatatat tttaaagcac
5521  ttaagaata tgaaactttc atatatgtta aaggattata atttatggaa ttaaaaaatg
5581  cagtgtagtc cttaaaaaaa a
```

FIG._2E-2

```
MPPAVRRSACSMGWLWIFGAALGQCLGYSSQQQRVPFLQPPGQS
QLQASYVEFRPSQGCSPGYYRDHKGLYTGRCVPCNCNGHSNQCQDGSGICVNCQHNTA
GEHCERCQEGYYGNAVHGSCRACPCPHTNSFATGCVVNGGDVRCSCKAGYTGTQCERC
APGYFGNPQKFGGSCQPCSCNSNGQLGSCHPLTGDCINQEPKDSSPAEECDDCDSCVM
TLLNDLATMGEQLRLVKSQLQGLSASAGLLEQMRHMETQAKDLRNQLLNYRSAISNHG
SKIEGLERELTDLNQEFETLQEKAQVNSRKAQTLNNNVNRATQSAKELDVKIKNVIRN
VHILLKQISGTDGEGNNVPSGDFSREWAEAQRMMRELRNRNFGKHLREAEADKRESQL
LLNRIRTWQKTHQGENNGLANSIRDSLNEYEAKLSDLRARLQEAAAQAKQANGLNQEN
ERALGAIQRQVKEINSLQSDFTKYLTTADSSLLQTNIALQLMEKSQKEYEKLAASLNE
ARQELSDKVRELSRSAGKTSLVEEAEKHARSLQELAKQLEEIKRNASGDELVRCAVDA
ATAYENILNAIKAAEDAANRAASASESALQTVIKEDLPRKAKTLSSNSDKLLNEAKMT
QKKLKQEVSPALNNLQQTLNIVTVQKEVIDTNLTTLRDGLHGIQRGDIDAMISSAKSM
VRKANDITDEVLDGLNPIQTDVERIKDTYGRTQNEDFKKALTDADNSVNKLTNKLPDL
WRKIESINQQLLPLGNISDNMDRIRELIQQARDAASKVAVPMRFNGKSGVEVRLPNDL
EDLKGYTSLSLFLQRPNSRENGGTENMFVMYLGNKDASRDYIGMAVVDGQLTCVYNLG
DREAELQVDQILTKSETKEAVMDRVKFQRIYQFARLNYTKGATSSKPETPGVYDMDGR
NSNTLLNLDPENVVFYVGGYPPDFKLPSRLSFPPYKGCIELDDLNENVLSLYNFKKTF
NLNTTEVEPCRRRKEESDKNYFEGTGYARVPTQPHAPIPTFGQTIQTTVDRGLLFFAE
NGDRFISLNIEDGKLMVRYKLNSELPKERGVGDAINNGRDHSIQIKIGKLQKRMWINV
DVQNTIIDGEVFDFSTYYLGGIPIAIRERFNISTPAFRGCMKNLKKTSGVVRLNDTVG
VTKKCSEDWKLVRSASFSRGGQLSFTDLGLPPTDHLQASFGFQTFQPSGILLDHQTWT
RNLQVTLEDGYIELSTSDSGSPIFKSPQTYMDGLLHYVSVISDNSGLRLLIDDQLLRN
SKRLKHISSSRQSLRLGGSNFEGCISNVFVQRLSLSPEVLDLTSNSLKRDVSLGGCSL
NKPPFLMLLKGSTRFNKTKTFRINQLLQDTPVASPRSVKVWQDACSPLPKTQANHGAL
QFGDIPTSHLLFKLPQELLKPRSQFAVDMQTTSSRGLVFHTGTKNSFMALYLSKGRLV
FALGTDGKKLRIKSKEKCNDGKWHTVVFGHDGEKGRLVVDGLRAREGSLPGNSTISIR
APVYLGSPPSGKPKSLPTNSFVGCLKNFQLDSKPLYTPSSSFGVSSCLGGPLEKGIYF
SEEGGHVVLAHSVLLGPEFKLVFSIRPRSLTGILIHIGSQPGKHLCVYLEAGKVTASM
DSGAGGTSTSVTPKQSLCDGQWHSVAVTIKQHILHLELDTDSSYTAGQIPFPPASTQE
PLHLGGAPANLTTLRIPVWKSFFGCLRNIHVNHIPVPVTEALEVQGPVSLNGCPDQ
```

```
   1  gtataagagg aagaacacaa aggtttgcag cagccaggca gaacaccaag ggatcaagat
  61  gccgcctaca gtgaggtggt cagcctggtg cacaggatgg ctgtggatct ttggggcagc
 121  tctgggccag tgcctggggt atggctcaga gcagcaaagg gtagcatttc ttcagcatcc
 181  agggcaaaac catctgcaag caagttatat ggagcttaga cccagccagg gctgtcgccc
 241  aggatactat cgagacatca aaagcttccc tgcgggaagg tctgttccct gcaattgcaa
 301  cggacattca aatagatgcc aagacggctc gggagtgtgc attaactgtc agcacaacac
 361  agctggggag cactgtgagc gttgcaagag gggttactat ggaagcgcca tccatggatc
 421  ctgcagggtt tgcccctgtc ctcacaccaa cagctttgcc actggctgtg ctgtggatgg
 481  aggagctgtg aggtgtgcct gcaaacccgg atacacagga gcacagtgtg agaggtgtgc
 541  accaggatat tttgggaacc cccagaaatt tggaggtagc tgccaaccat gcaattgcaa
 601  cagtaatggc cagtttggca cttgtgatcc cctaactgga gactgtgtaa gccaagaacc
 661  caaagatggc agccctgcag aagaatgtga tgactgtgac agctgtgtga tgactctcct
 721  aaatgacttg gtccccatgg gtgaggaact cgccctggtg aaatcaaaac ttcaggggct
 781  gagtgtgaac actggttctc tggaacagat ccggcatgtg gagatgcagg ccaaggacct
 841  gaggaaccag ctgcttggct tccgttccgc catctccagt cacgggtccc aaatggacgg
 901  cctggaaaaa gaactcagtc atttgtacca ggaattcgaa actttgcaag aaaaggcgca
 961  ggtcaattcc agaaaagcac aaacattata taacaacatc gatacgacaa tccaaaacgc
1021  caaagagttg gacatgaaga ttaaaaacat acttacgaat gtgcacattc tcctgaagca
1081  gatcgctcgg ccaggtggag aaggaatgga cttgccggtg ggcgactggt ccagggagtc
1141  ggcggaagct cagcgcatgt tgcgggagct gcgaggccga gactttaaaa agcacctcca
1201  agaagcagag gcccagaaaa tggaagccca gctcttactg aaccgaatca ggacctggct
1261  ggaatcccac caggtggaga caatggact gctaaagaat attcgggatt cattaaatga
1321  ttatgaagcc aaacttcagg acctgcgttc cgtgcttcag gaggcggcag cccagggaaa
1381  gcaggctaca ggcctcaacc acgaaaatga gggggtccta ggagccatcc agagacaaat
1441  gaaggaaatg gattccctga agaagtacct caccgagcac ctggccacag cagacgcttc
1501  cctgctgcaa accaacagtc tactgcagcg gatggacacg agccagaagg agtatgaaag
1561  cttagctgct gctttaaacg gagcaagaca ggaactgaat gaccaagtgc gggaactctc
1621  cagatccgga ggcaaagcac ccctggtggc tgaggccgag aagcacgctc agtctttaca
1681  ggagctggca aagcagctgg aagagataaa gagaaacacc agtggggatg agtcggtgcg
1741  ctgtgtcgtg gacgctgcca ctgcctatga gagcatcctc aacgccatcc gagcagcaga
1801  ggatgcagcc ggcaaggcca acagtgcctc agagtccgcc ttccagacag tgataaagga
1861  agatcttccg agaagagcca aaaccctgag ttctgacagc gaggaactgt taaacgaggc
1921  caagatgaca cggaaaaggc tacagcaaga aatcaatcca gctctcaaca gcctacagca
1981  aaccctgaag actgtatcag ttcagaagga cctgctagat gccaatgtca ctgctgtccg
2041  taatgacctt cgtgggatcc agagaggtga tattgacagt gtggtgagtg agcgaagag
2101  catggtcagg aaagccaatg ggataacgag cgaggtcctg gacgggctca gccccatcca
2161  gacggatttg ggaaggatta aggacagcta cggagcaca cggcatgagg acttcaacaa
2221  agctctgatt gacgccaata actcagtaaa gaaattaacc aagaagttgc ctgatctttt
2281  tgtcaagatt gaaagcatca atcaacagtt gctgcccctg gaaacatct ctgacaatgt
2341  agaccgaatc cgagagctca ttacgcaggc cagagatgct gcgaacaagg ttgcaattcc
2401  catgaggttc aatggtaaat ctggtgttga agtccgtctg ccaaatgacc tagaagactt
2461  gaagggatac acgtctctgt ctttgttcct ccaaagacca gacttaagag agaatggagg
2521  cactgaggac atgtttgtaa tgtaccttgg aaacaaggat gcctccaagg actacatcgg
2581  catggcggtt gtagatggcc agctgacgtg tgtctacaac ctgggggacc gagaagctga
2641  agttcagatc gatcaggtcc tgacggagag tgagtctcag gaggcagtta tggaccgggt
2701  gaagttccag agaatatatc aatttgccaa gcttaattac accaaagaag ccacgtccaa
2761  taaacccaaa gctcccgcgg tctacgacct ggagggtggc agtagcaaca cgctccttaa
2821  tttggatccc gaggacgctg tgttttatgt cggaggttac ccaccggatt tgaacttcc
2881  tagcagactg cggttccctc catacaaagg ctgtatcgaa ctagatgacc tcaatgaaaa
```

```
2941  cgttctaagc ttgtacaatt tcaagacaac tttcaatctc aacaccacgg aggtggagcc
3001  ttgtaggagg agaaaggaag agtcagacaa aaattacttt gaaggtacag gctatgctcg
3061  catccctact caaccaaatg ctcccttccc aaacttcata cagaccatcc agactactgt
3121  ggacagaggt ttactgttct tcgcagaaaa ccaggataac ttcatatctc tgaacataga
3181  agatggcaat ctcatggtga gatacaaact aaattcagag ccacccaaag agaagggaat
3241  tcgagacacc atcaacgatg ggaaagatca ttcgatctta atcacaattg gaaaactaca
3301  aaaacgcatg tggataaatg tgaacgaacg cagtgtacga atcgaagggg aaatatttga
3361  tttcagcaca tattatttgg gcggaattcc aattgcaatc agagaaaggt ttaacatctc
3421  aacgcctgct ttccaaggct gcatgaagaa tctgaagaaa accagtgggg ttgtcaggtt
3481  gaatgatact gtgggtgtaa ccaagaagtg ctcagaagac tggaagcttg tgcgaaccgc
3541  ctcgttctcc agaggagggc agatgagctt tacaaacttg gacgtgccct cgactgaccg
3601  cttccagctc tcctttgggt ttcagacctt tcaacccagt ggcacactgc tcaatcatca
3661  gacgcggaca agcagcctgc tggtcaccct ggaagatggg cacattgagt tgagcactag
3721  ggacagcaac atcccaattt tcaagtctcc agggacctac atggacggtt tactgcatca
3781  tgtatctgta ataagtgaca cctcaggtct ccgccttctc atcgatgacc aggtcctgag
3841  aaggaaccag aggcttccta gcttctctaa cgcccagcag tcgctccgcc ttggaggagg
3901  tcatttcgag ggttgtatca gcaatgtttt agtccaaagg ttttcacaga gtccagaagt
3961  cctggatctg gccagtaaat ctaccaagaa ggatgcatcc ctaggaggct gcagtttaaa
4021  caagccacct tttcttatgt tgtttaaaag tcccaagaga tttaacaagg gccggatttt
4081  caatgttaat cagctgatgc aagatgcacc tcaggccaca aggagcacag aggcttggca
4141  agatgggagg tcctgcctac cacctctgaa caccaaggcc tctcacagag ccctgcagtt
4201  tggagacagc cccaccagcc acttgctact caagcttccc caggaactgc tgaaacctag
4261  gtcacagttt tctttagaca tacagacaac ttcccccaaa ggactggtgt tttacgcagg
4321  caccaaggac tccttcctgg ctctttatgt cgcagatggc cgtgttgtct ttgctttggg
4381  ggcaggaggg aagaaactga gactcaggag caaggagaga taccatgacg ggaagtggca
4441  cacggtggtg ttcggactaa atggaggaaa ggcacgcctg gttgtggatg ggctaagggc
4501  ccaggaaggc agtttgcctg gaaattctac catcagcccc agagaacagg tttacctagg
4561  gttgccgcta tcaagaaagc caaagagcct accccagcac agttttgtgg ggtgcctgag
4621  agatttccag ttgaactcga aaccctggga ttctccttct gcgaggtttg gggtatctcc
4681  ctgcttgggt ggctctttag agaaaggcat ttatttctcc caaggaggag gccatgtgat
4741  cctagccaat tctgtgtcct tggggccaga gcttaagctc actttcagca ttcgcccacg
4801  gagtctcact ggggtcttaa tacacgtcgg aagtcaatct ggacagcgct taagtgtgta
4861  catggaggca ggaaaggtca caacctctgt gagcagtgat gcaggaggaa gtgtgacatc
4921  aattacaccg aagcagtctc tgtgtgatgg acagtggcac tcggtggcag tctccattaa
4981  acagcgcatc ctgcatctag aactggatac agacagtagc tacacagtcg caccactttc
5041  cttctcacca aacagcaccc gagggtcact gcacgtcgga ggtgtcccag acaaattgaa
5101  aatgcttaca ctccctgtgt ggaactcatt ttttggctgt ctgaagaata ttcaagtcaa
5161  ccatgtccct gtccccatca cagaagccac agaagtccaa ggttctgtca gcctgaatgg
5221  ctgccctgac cactaaccct acacagcaag attcaccttt ggag
```

FIG._2G-2

```
MPPTVRWSAWCTGWLWIFGAALGQCLGYGSEQQRVAFLQHPGQN
HLQASYMELRPSQGCRPGYYRDIKSFPAGRSVPCNCNGHSNRCQDGSGVCINCQHNTA
GEHCERCKRGYYGSAIHGSCRVCPCPHTNSFATGCAVDGGAVRCACKPGYTGAQCERC
APGYFGNPQKFGGSCQPCNCNSNGQFGTCDPLTGDCVSQEPKDGSPAEECDDCDSCVM
TLLNDLVPMGEELALVKSKLQGLSVNTGSLEQIRHVEMQAKDLRNQLLGFRSAISSHG
SQMDGLEKELSHLYQEFETLQEKAQVNSRKAQTLYNNIDTTIQNAKELDMKIKNILTN
VHILLKQIARPGGEGMDLPVGDWSRESAEAQRMLRELRGRDFKKHLQEAEAQKMEAQL
LLNRIRTWLESHQVENNGLLKNIRDSLNDYEAKLQDLRSVLQEAAAQGKQATGLNHEN
EGVLGAIQRQMKEMDSLKKYLTEHLATADASLLQTNSLLQRMDTSQKEYESLAAALNG
ARQELNDQVRELSRSGGKAPLVAEAEKHAQSLQELAKQLEEIKRNTSGDESVRCVVDA
ATAYESILNAIRAAEDAAGKADSASESAFQTVIKEDLPRRAKTLSSDSEELLNEAKMT
RKRLQQEINPALNSLQQTLKTVSVQKDLLDANVTAVRNDLRGIQRGDIDSVVSGAKSM
VRKANGITSEVLDGLSPIQTDLGRIKDSYGSTRHEDFNKALIDANNSVKKLTKKLPDL
FVKIESINQQLLPLGNISDNVDRIRELITQARDAANKVAIPMRFNGKSGVEVRLPNDL
EDLKGYTSLSLFLQRPDLRENGGTEDMFVMYLGNKDASKDYIGMAVVDGQLTCVYNLG
DREAEVQIDQVLTESESQEAVMDRVKFQRIYQFAKLNYTKEATSNKPKAPAVYDLEGG
SSNTLLNLDPEDAVFYVGGYPPDFELPSRLRFPPYKGCIELDDLNENVLSLYNFKTTF
NLNTTEVEPCRRRKEESDKNYFEGTGYARIPTQPNAPFPNFIQTIQTTVDRGLLFFAE
NQDNFISLNIEDGNLMVRYKLNSEPPKEKGIRDTINDGKDHSILITIGKLQKRMWINV
NERSVRIEGEIFDFSTYYLGGIPIAIRERFNISTPAFQGCMKNLKKTSGVVRLNDTVG
VTKKCSEDWKLVRTASFSRGGQMSFTNLDVPSTDRFQLSFGFQTFQPSGTLLNHQTRT
SSLLVTLEDGHIELSTRDSNIPIFKSPGTYMDGLLHHVSVISDTSGLRLLIDDQVLRR
NQRLPSFSNAQQSLRLGGGHFEGCISNVLVQRFSQSPEVLDLASKSTKKDASLGGCSL
NKPPFLMLFKSPKRFNKGRIFNVNQLMQDAPQATRSTEAWQDGRSCLPPLNTKASHRA
LQFGDSPTSHLLLKLPQELLKPRSQFSLDIQTTSPKGLVFYAGTKDSFLALYVADGRV
VFALGAGGKKLRLRSKERYHDGKWHTVVFGLNGGKARLVVDGLRAQEGSLPGNSTISP
REQVYLGLPLSRKPKSLPQHSFVGCLRDFQLNSKPLDSPSARFGVSPCLGGSLEKGIY
FSQGGGHVILANSVSLGPELKLTFSIRPRSLTGVLIHVGSQSGQRLSVYMEAGKVTTS
VSSDAGGSVTSITPKQSLCDGQWHSVAVSIKQRILHLELDTDSSYTVAPLSFSPNSTR
GSLHVGGVPDKLKMLTLPVWNSFFGCLKNIQVNHVPVPITEATEVQGSVSLNGCPDH
```

```
   1  atgtcagagg gcatttgctg ccgagctggc gcactgtgca agagtggaca gcaagtttcc
  61  actgtggtgg tggtagatcc accaaaccat gccagtggaa tgagaactga atgcagccca
 121  ccagagcacg tgcacacgtg cattaaggaa cctcagaatc agctcttcca tgtggcttat
 181  atcttaatca aatttgcaaa ctctccccgc cctgatcttt ggatcctgga aagatctgta
 241  gactttggaa gcacctactc accatggcag tattttgctc attctagaag agattgtgta
 301  gaacagtttg ggcaagaagc aaacatggca attacccagg acgaccagat gctctgtgtc
 361  acggagtatt cccgtatcgt gcctctggaa aatggcgaga ttgttgtatc cttgataaat
 421  ggtcgtccag gtgcaaaaaa gtttgctttc tctgacactc tgagggagtt tactaaggca
 481  acaaacatcc gcttgcggtt tctgcgaacc aacaccctcc tcgggcatct tatttccaag
 541  gcagagcgag accccactgt cacgcgccgg tattattgca tggaagctga tgatgctctg
 601  ttctctgtcc tgcagtatta ttacagcata aaggatatca gtgttggtgg gcggtgtgtt
 661  tgcaacggcc atgcggaggc gtgcagtgct gacaaccctg aaaagcagtt ccgatgcgaa
 721  tgccagcacc atacctgtgg agacacgtgt aaccgctgct gtgcaggtta caatcagagg
 781  cgctggcagc ctgctggtca ggagcagcac aatgagtgtg aagcctgcaa ctgccatggg
 841  catgctgtgg actgctacta tgacccagac gtggagcacc agcaggcgag cttgaacagc
 901  aaaggcgtct acgcaggtgg aggggtctgc atcaactgtc agcacaacac tgcaggcgtg
 961  aactgtgaaa agtgtgcgaa gggttacttc cggccccatg gagttccggt ggatgcactg
1021  catggatgca tcccttgcag ctgtgaccca gaacgcgcag atgactgtga ccagggctca
1081  ggccactgcc attgtaagcc aaatttctcc ggagactact gtgagacgtg tgcagatggg
1141  tactataatt ttccattttg cttgagaatt ccagtctttc ccaactacac tccaagtcca
1201  gaagatccag tggctggcaa tataaaaggc aaggatccag ggactctaga cccaccagtc
1261  atagcaaatg gggcatatct tggagcttca agactagagc aaggagccac aggccagggc
1321  agccctgctg agagggtcac ccacaccaac tcatggctga ttcctcaat gcctatgctc
1381  caggttaggg ctgccatcca tgaggctaag tgttactctc tgtgtttctg tatgtatgtt
1441  gagcacagtg ggactgtacc acctgctctg gggtcaggtt atacagggga ctctgagcct
1501  aaaacaggaa cccaggcaaa aaggggggtgt gactgtaact tggaaggtgt tctcccagag
1561  atatgtgacg atcgtggcag gtgcctgtgc cgccctgggg ttgagggtcc ccagtgtgac
1621  tcctgccgct cgggctccta ttcatttccc atatgccaag cttgccagtg ttcgacgatt
1681  ggatcctatc cagtgccctg tgacccgggg aatggccagt gtgactgcct gcctggaatt
1741  accgggaggc agtgtgacag gtgtctctcg ggagcctatg actttccata ctgccaaggt
1801  aaggaagccg gcagcatgtt ggaggctcgg tcctcatctg agtgggtgca gctgacctct
1861  tggagaagcc tgggttattg tcagtgcaag cagcatgttg caagtcctac atgtagtgtc
1921  tgcaaaccat tatattggaa tctggccaaa gaaaacccc gtggatgctc agagtgccag
1981  tgccatgaag cagggacatt gagtggaatt ggagagtgtg ggcaggagga cggtgactgt
2041  agctgcaaag cccatgtaac tggtgatgcc tgcgacacct gtgaagatgg gttttctct
2101  ttggagaaga gcaattactt tggctgtcaa gggtgtcagt gtgacattgg tggagcactc
2161  accaccatgt gtagtgggcc ctcgggagta tgccagtgca gagagcacgt ggagggggaaa
2221  cagtgccaga ggcctgaaaa taactactac ttcccggatt gcaccacat gaagtatgag
2281  gtcgaagatg gcactggacc taatgaaaga aacctgcggt ttggattga tcccctggta
2341  ttccctgagt ttagctggag aggatatgct ccaatgacct cagtccaggt atatatgagt
2401  gagtgtgtgt gtcctctaca ctgcatgtta ttttgggggta cttttcagaa tgaagtaagg
2461  gtgagattgt ctgtgaggca gtccagcctc tccttgttcc gcatcgttct gagatacatc
2521  agtcctggaa cggaagccat atccggccga atcactcttt actcatcgca gggagattcg
2581  gatgctttgc aaagcagaaa aatcaccttt ccccgagta aagagccagc ctttgtcaca
2641  gtccctggga atggctttgc aggcccattc tccatcacac tgggacgtg gattgcttgc
2701  atccaggtgg aaggagtcct tctggactac ctggtgctgc ttcccaggga ctactatgaa
2761  gcattcaccc tgcaagtgcc agtcacagag ccatgtgccc acacaggatc tccccaggac
2821  aactgtttgc tttaccagca tttaccactg actgcattct cctgtaccct ggcttgtgag
2881  gccagacact tcctgctgga tggagagctg agacccttgg caatgaggca gcccacacca
```

FIG._21-2

```
2941  acacacccag ccatggtgga cctcagcggg agagaggtag aactgcagct tcgtctgcgg
3001  gtcccacagg ttggccacta cgtggtcctg ctggagtatg ccacggaggt ggagcagctt
3061  tttgtggtgg acgtgaatct gaagagctca gggtctgcct tggcaggcca ggtgaacata
3121  tacagctgca agtacagcat cccgtgcagg agtgtggtga ttgacagcct gagtcgcacg
3181  gctgtacatg agctgttggc agatgcagac attcagctca aggcgcacat ggcccatttc
3241  cttttgtatc acatttgtat tataccagct gaagaattct caactgaata tttgagacct
3301  caagtccact gcattgccag ctacaggcag catgctaatc caagtgcttc ctgtgtctcc
3361  ctggcccatg aaactcctcc aacagcctca attttggatg ctacaagtag gggccttttc
3421  tctgccctac ctcatgagcc ttcctctcct gcagatggag ttactctgaa ggcaccacag
3481  agtcaagtga ccctgaaagg actcatacca cacctgggcc gacacgtctt tgtcatccat
3541  ttttatcaag cagagcaccc agggtttccc actgaggtga ttgtgaatgg aggaagacag
3601  tggtcaggtt ccttccttgc ctccttctgt ccccacttac ttggctgccg ggaccaggtg
3661  atctctgatg gccaagtgga gtttgacatc tctgaagcag aggtagctgt gacagtgaag
3721  attccagatg gaaagtcctt aacattggtc cgggttctag tggtacctgc agagaattac
3781  gactaccaaa ttcttcacaa aacaacagtg gacaagtcct ccgagttcat cagcagttgt
3841  ggaggagaca gcttttatat tgatcatccag gcagcctctg gattctgtaa gaattctgca
3901  aggtccctgg tagccttta ccataacggt gccatacact gtgagtgcga ccctgctggg
3961  actgccggcc accactgtag tcctgagggt gggcagtgcc cttccggcc caatgtcatc
4021  gggaggcagt gcagccgctg tgcgacaggc tactatggat tcccatactg caagccttgt
4081  aattgtggca gacgcctttg tgaagaggtg acagggaagt gtctctgccc accccacaca
4141  gtcaggcctc agtgtgaggt ctgtgagatg aattccttca actttcaccc tgtggctggc
4201  tgtgacgtct gcaactgctc caggaagggc accattgagg cggccgtctc tgagtgtgac
4261  agggacagcg ggcagtgcag gtgcaagcct agagtcacag ggcagcagtg tgacaagtgt
4321  gctcctggct tctaccagtt ccctgagtgt gtcccctgca gctgtaacag agatgggact
4381  gagcccagcg tatgtgaccc agagactggg gcttgcatgt gcaaggaaaa tgtagagggc
4441  ccccaatgtc aactgtgtcg agaaggatca ttctacctgg acccaacaaa cccaagggt
4501  tgtaccaagt gcttctgttt tggagtgaat actgactgtc agagttcgca taagcaacga
4561  gctaagtttg tagacatgat gggctggcgt ctggagacag cagatggagt tgatgtccct
4621  gtgtccttca accctggcag caacagcatg gtggcagatc tgcaggagct gccaccctca
4681  gttcacagtg catcctgggt ggcacctcca tcctacctag gtgataaggt atcatcgtac
4741  ggcggctacc tcacctacca cgccaagtcc tttggcttac ctggagatat ggttcttctg
4801  ggaaagcagc cagatgtgca gctcactggt caacacatgt ccctcatcca taaggaaccc
4861  agcgacccac ggccagacag gctgcatcac ggaagagtgc aagtgattga gggaaacttc
4921  agacacgaag gcagcagtgc cccagtgtcc cgggaggagc tgatgactgt gctgtccaga
4981  ctggaaagac tccacatccg gggcctccat ttcaccgaga cacagcggct cacctggt
5041  gaggtagggc tggaggaggc ctctgacacg ggaagcggac ccagggctca tcttgtggag
5101  atgtgtgcct gcccccctga ctacacaggt gactcatgcc agggttgtcg ccctggatac
5161  tattgggaca acaaaagctt acctgtagga aggtgtgttc cctgcaattg caacggacat
5221  tcaaatagat gccaggatgg ctccgggata tgcattaact gtcagcacaa cacagctggg
5281  gagcactgtg agcgttgcca agcaggtcac tatggaaatg ccatccacgg atcttgtagg
5341  gtctgccct gccctcatac caacagtttt gccaccggct gtgctgtgga tggtggagct
5401  gtgaggtgtg cctgcaaacc cggatacaca ggaacacagt gtgagaggtg tgcaccagga
5461  tattttggga acccccagaa atttggaggt agctgccagc catgcaattg taacagcaat
5521  ggccagttag gtccttgcga cccctaact ggagactgtg taaaccaaga acccaaagat
5581  ggcagccctg cagaagaatg tgatgactgc gacagctgtg tgatgacgct cttaaatgac
5641  ttggcctcca tgggtgagga actccgcctg gtgaagtcaa agctgcaggg gctgagtgtg
5701  agcacgggtg ctctggaaca gatccggcac atggagacgc aggccaagga cctgaggaac
5761  cagctgcttg gcttccgttc tgccacctca agtcatgggt ccaaaatgga tgacctgaa
5821  aaagagctga gtcatttgaa ccgggaattt gaaactctgc aagaaaaggc acaggtcaat
```

```
5881  tccagaaaag cacaaacatt atataacaac attgatcaga caatccaaag tgccaaagaa
5941  ctggacatga agattaaaaa catcgttcag aatgtgcaca ttctcctgaa gcagatggcg
6001  aggccaggtg gagaaggcac ggacttgcca gtgggtgact ggtccaggga gctggccgaa
6061  gctcaacgca tgatgcgaga cctgcgaagc cgagacttta aaaagcacct ccaagaagca
6121  gaggccgaga aaatggaagc ccagctctta ctgcaccgga tcaggacctg gctggaatcc
6181  caccaggtgg agaacaacgg actgctaaag aatattcggg actccttaaa tgattatgaa
6241  gacaaacttc aggacctacg ttccatcctc caggaggcag ctgcccaggc aaagcaggcc
6301  actggcatca accatgaaaa tgaggggggtt ctcggagcca tccagagaca aatgaaagaa
6361  atggattccc tgaagaatga cttcaccaag tacctggcca cagccgactc ttccctgctg
6421  cagaccaaca atctactgca gcagatggac aaaagccaga aggaatatga aagcttagct
6481  gctgctttaa atggagcaag acaggaactg agtgacagag tgcgagaact gtccagatcg
6541  ggtggcaaag caccgctggt ggtggaggca gagaagcatg cacagtcttt acaggagctg
6601  gcaaagcagc tggaagagat aaagagaaac accagcgggg atgagctggt gcgttgtgct
6661  gtggatgctg ccacggccta tgagaacatc ctcaatgcca tcagagcagc agaggatgca
6721  gccagcaagg ccaccagtgc ctccaagtct gccttccaaa cagtgataaa ggaagacctt
6781  ccaaaaagag ctaagaccct gagttctgac agcgaggaac tgttaaatga agccaagatg
6841  acacagaaaa ggctacagca agtcagtcca gctctcaaca gcctacaaca aaccctgaag
6901  actgtatcag ttcagaagga cctgctagat gccaacctca ctgttgcccg tgatgatctt
6961  catgggatac agagaggtga tatcgacagt gtggtgatcg gtgcaaagag catggtcagg
7021  gaagccaacg gaataacaag cgaggtcctg gacgggctca accccatcca gacagatttg
7081  ggaaggatta aggacagcta tgagagcgca cggcgtgaag acttcagcaa ggctctggtc
7141  gatgccaata actcagtaaa gaaattaacc aggaagttgc ctgatctttt tatcaagatt
7201  gaaagtatca accaacagtt gctgccctg gggaacatct ctgacaatgt ggaccgaatc
7261  cgagaactca ttcagcaggc cagagatgct gcaaacaagg tgggtattcc catttggctc
7321  tag
```

FIG._21-3

```
MSEGICCRAGALCKSGQQVSTVVVVDPPNHASGMRTECSPPEHV
HTCIKEPQNQLFHVAYILIKFANSPRPDLWILERSVDFGSTYSPWQYFAHSRRDCVEQ
FGQEANMAITQDDQMLCVTEYSRIVPLENGEIVVSLINGRPGAKKFAFSDTLREFTKA
TNIRLRFLRTNTLLGHLISKAERDPTVTRRYYCMEADDALFSVLQYYYSIKDISVGGR
CVCNGHAEACSADNPEKQFRCECQHHTCGDTCNRCCAGYNQRRWQPAGQEQHNECEAC
NCHGHAVDCYYDPDVEHQQASLNSKGVYAGGGVCINCQHNTAGVNCEKCAKGYFRPHG
VPVDALHGCIPCSCDPERADDCDQGSGHCHCKPNFSGDYCETCADGYYNFPFCLRIPV
FPNYTPSPEDPVAGNIKGKDPGTLDPPVIANGAYLGASRLEQGATGQGSPAERVTHTN
SWLSSSMPMLQVRAAIHEAKCYSLCFCMYVEHSGTVPPALGSGYTGDSEPKTGTQAKR
GCDCNLEGVLPEICDDRGRCLCRPGVEGPQCDSCRSGSYSFPICQACQCSTIGSYPVP
CDPGNGQCDCLPGITGRQCDRCLSGAYDFPYCQGKEAGSMLEARSSSEWVQLTSWRSL
GYCQCKQHVASPTCSVCKPLYWNLAKENPRGCSECQCHEAGTLSGIGECGQEDGDCSC
KAHVTGDACDTCEDGFFSLEKSNYFGCQGCQCDIGGALTTMCSGPSGVCQCREHVEGK
QCQRPENNYYFPDLHHMKYEVEDGTGPNGRNLRFGFDPLVFPEFSWRGYAPMTSVQVY
MSECVCPLHCMLFWGTFQNEVRVRLSVRQSSLSLFRIVLRYISPGTEAISGRITLYSS
QGDSDALQSRKITFPPSKEPAFVTVPGNGFAGPFSITPGTWIACIQVEGVLLDYLVLL
PRDYYEAFTLQVPVTEPCAHTGSPQDNCLLYQHLPLTAFSCTLACEARHFLLDGELRP
LAMRQPTPTHPAMVDLSGREVELQLRLRVPQVGHYVVLLEYATEVEQLFVVDVNLKSS
GSALAGQVNIYSCKYSIPCRSVVIDSLSRTAVHELLADADIQLKAHMAHFLLYHICII
PAEEFSTEYLRPQVHCIASYRQHANPSASCVSLAHETPPTASILDATSRGLFSALPHE
PSSPADGVTLKAPQSQVTLKGLIPHLGRHVFVIHFYQAEHPGFPTEVIVNGGRQWSGS
FLASFCPHLLGCRDQVISDGQVEFDISEAEVAVTVKIPDGKSLTLVRVLVVPAENYDY
QILHKTTVDKSSEFISSCGGDSFYIDPQAASGFCKNSARSLVAFYHNGAIPCECDPAG
TAGHHCSPEGGQCPCRPNVIGRQCSRCATGYYGFPYCKPCNCGRRLCEEVTGKCLCPP
HTVRPQCEVCEMNSFNFHPVAGCDVCNCSRKGTIEAAVSECDRDSGQCRCKPRVTGQQ
CDKCAPGFYQFPECVPCSCNRDGTEPSVCDPETGACMCKENVEGPQCQLCREGSFYLD
PTNPKGCTKCFCFGVNTDCQSSHKQRAKFVDMMGWRLETADGVDVPVSFNPGSNSMVA
DLQELPPSVHSASWVAPPSYLGDKVSSYGGYLTYHAKSFGLPGDMVLLGKQPDVQLTG
QHMSLIHKEPSDPRPDRLHHGRVQVIEGNFRHEGSSAPVSREELMTVLSRLERLHIRG
LHFTETQRLTLGEVGLEEASDTGSGPRAHLVEMCACPPDYTGDSCQGCRPGYYWDNKS
LPVGRCVPCNCNGHSNRCQDGSGICINCQHNTAGEHCERCQAGHYGNAIHGSCRVCPC
PHTNSFATGCAVDGGAVRCACKPGYTGTQCERCAPGYFGNPQKFGGSCQPCNCNSNGQ
LGPCDPLTGDCVNQEPKDGSPAEECDDCDSCVMTLLNDLASMGEELRLVKSKLQGLSV
STGALEQIRHMETQAKDLRNQLLGFRSATSSHGSKMDDLEKELSHLNREFETLQEKAQ
VNSRKAQTLYNNIDQTIQSAKELDMKIKNIVQNVHILLKQMARPGGEGTDLPVGDWSR
ELAEAQRMMRDLRSRDFKKHLQEAEAEKMEAQLLLHRIRTWLESHQVENNGLLKNIRD
SLNDYEDKLQDLRSILQEAAAQAKQATGINHENEGVLGAIQRQMKEMDSLKNDFTKYL
ATADSSLLQTNNLLQQMDKSQKEYESLAAALNGARQELSDRVRELSRSGGKAPLVVEA
EKHAQSLQELAKQLEEIKRNTSGDELVRCAVDAATAYENILNAIRAAEDAASKATSAS
KSAFQTVIKEDLPKRAKTLSSDSEELLNEAKMTQKRLQQVSPALNSLQQTLKTVSVQK
DLLDANLTVARDDLHGIQRGDIDSVVIGAKSMVREANGITSEVLDGLNPIQTDLGRIK
DSYESARREDFSKALVDANNSVKKLTRKLPDLFIKIESINQQLLPLGNISDNVDRIRE
LIQQARDAANKVGIPIWL"
```

FIG. 2J

CSPLPKTQANHGALQFGDIPTSHLLFKLPQELLKPRSQFAVDMQTTSSRGLVFHTGTKNSFMAL
YLSKGRLVFALGTDGKKLRIKSKEKCNDGKWHTVVFGHDGEKGRLVVDGLRAREGSLPGNSTIS
IRAPVYLGSPPSGKPKSLPTNSFVGCLKNFQLDSKPLYTPSSSFGVSSCLGGPLEKGIYFSEEG
GHVVLAHSVLLGPEFKLVFSIRPRSLTGILIHIGSQPGKHLCVYLEAGKVTASMDSGAGGTSTS
VTPKQSLCDGQWHSVAVTIKQHILHLELDTDSSYTAGQIPFPPASTQEPLHLGGAPANLTTLRI
PVWKSFFGCLRNIHVNHIPVPVTEALEVQGPVSLNGCPDQ

FIG._3A

```
t gctcaccact tcccaagacc caggccaatc atggagccct ccagtttggg
gacattccca ccagccactt gctattcaag cttcctcagg agctgctgaa
acccaggtca cagtttgctg tggacatgca gacaacatcc tccagaggac
tggtgtttca cacgggcact aagaactcct ttatgctct ttatctttca
aaaggacgtc tggtctttgc actggggaca gatgggaaaa aattgaggat
caaaagcaag gagaaatgca atgatgggaa atggcacacg gtggtgtttg
gccatgatgg ggaaaagggg cgcttggttg tggatggact gagggcccgg
gagggaagtt tgcctggaaa ctccaccatc agcatcagag cgccagttta
cctgggatca cctccatcag ggaaacaaa gagcctcccc acaaacagct
ttgtgggatg cctgaagaac tttcagctgg attcaaaacc cttgtatacc
ccttcttcaa gcttcggggt gtcttcctgc ttgggtggtc ctttggagaa
aggcatttat ttctctgaag aaggaggtca tgtcgtcttg gctcactctg
tattgttggg gccagaattt aagcttgttt tcagcatccg cccaagaagt
ctcactggga tcctaataca catcggaagt cagcccggga agcacttatg
tgtttacctg gaggcaggaa aggtcacggc ctctatggac agtggggcag
gtgggacctc aacgtcggtc acaccaaagc agtctctgtg tgatggacag
tggcactcgg tggcagtcac cataaaacaa cacatcctgc acctggaact
ggacacagac agtagctaca cagctggaca gatccccttc ccacctgcca
gcactcaaga gccactacac cttggaggtg ctccagccaa tttgacgaca
ctgaggatcc ctgtgtggaa atcattcttt ggctgtctga ggaatattca
tgtcaatcac atccctgtcc ctgtcactga agccttggaa gtccaggggc
ctgtcagtct gaatggttgt cctgaccagt aacccaagcc tatttcacag
caaggaaatt caccttcaaa agcactgatt acccaatgca cctccctccc
cagctcgaga tcattcttca attaggacac aaaccagaca ggtttaatag
cgaatctaat tttgaattct gaccatggat acccatcact ttggcattca
gtgctacatg tgtattttat ataaaatcc catttcttga agataaaaaa
attgttattc aaattgttat gcacagaatg ttttttggtaa tattaatttc
cactaaaaaa ttaaatgtct
```

FIG._3B

CLGGPLEKGIYFSEEGGHVVLAHSVLLGPEFKLVFSIRPRSLTGILIHIGSQPGKHLCVYLEAG
KVTASMDSGAGGTSTSVTPKQSLCDGQWHSVAVTIKQHILHLELDTDSSYTAGQIPFPPASTQE
PLHLGGAPANLTTLRIPVWKSFFGCLRNIHVNHIPVPVTEALEVQGPVSLNGCPDQ

FIG._3C

```
tgc ttgggtggtc ctttggagaa aggcatttat ttctctgaag aaggaggtca
tgtcgtcttg gctcactctg tattgttggg gccagaattt aagcttgttt
tcagcatccg cccaagaagt ctcactggga tcctaataca catcggaagt
cagcccggga agcacttatg tgtttacctg gaggcaggaa aggtcacggc
ctctatggac agtggggcag gtgggacctc aacgtcggtc acaccaaagc
agtctctgtg tgatggacag tggcactcgg tggcagtcac cataaaacaa
cacatcctgc acctggaact ggacacagac agtagctaca cagctggaca
gatccccttc ccacctgcca gcactcaaga gccactacac cttggaggtg
ctccagccaa tttgacgaca ctgaggatcc ctgtgtggaa atcattcttt
ggctgtctga ggaatattca tgtcaatcac atccctgtcc ctgtcactga
agccttggaa gtccaggggc ctgtcagtct gaatggttgt cctgaccagt
aacccaagcc tatttcacag caaggaaatt caccttcaaa agcactgatt
acccaatgca cctccctccc cagctcgaga tcattcttca attaggacac
aaaccagaca ggtttaatag cgaatctaat tttgaattct gaccatggat
acccatcact ttggcattca gtgctacatg tgtattttat ataaaaatcc
catttcttga agataaaaaa attgttattc aaattgttat gcacagaatg
tttttggtaa tattaatttc cactaaaaaa ttaaatgtct
```

FIG._3D

PLPKTQANHGA

FIG._3E cact tcccaagacc caggccaatc atggagc

FIG._3F

------ KLPQELLKPRS

FIG._3G gccactt gctattcaag cttcctcagg agctgctgaa acccaggtca

FIG._3H

TSSRGLVFHTGTKNSFMALYLSKGRLVFALGTDGKKLRIKSKEKCNDGKWHTVVFGHDGEKGRL
VVDGLRAREGSLPGNSTISIRAPVYLGSPPSGKPKSLPTNSFVGCLKNFQLDSKPLYTPSSSFG
VSS

FIG._3I

```
gacaacatcc tccagaggac tggtgtttca cacgggcact aagaactcct
ttatggctct ttatctttca aaaggacgtc tggtctttgc actggggaca
gatgggaaaa aattgaggat caaaagcaag gagaaatgca atgatgggaa
atggcacacg gtggtgtttg gccatgatgg ggaaaagggg cgcttggttg
tggatggact gagggcccgg gagggaagtt tgcctggaaa ctccaccatc
agcatcagag cgccagttta cctgggatca cctccatcag ggaaaccaaa
gagcctcccc acaaacagct tgtgggatg cctgaagaac tttcagctgg
attcaaaacc cttgtatacc ccttcttcaa gcttcggggt gtcttcct
```

FIG._3J

TSSRGLVFHTGTKNSFMALYLSKGRLVFALGTDGKKLRIKSKEKCNDGKWHTVVFGHDGEKGRL
VVDGLRAREGSLPGNSTISIRAPVYLGSPPSGKPKSLPTNSFVGCLKNFQLDSKPLYTPSSSFG
VSSCLGGPLEKGIYFSEEGGHVVLAHSVLLGPEFKLVFSIRPRSLTGILIHIGSQPGKHLCVYL
EAGKVTASMDSGAGGTSTSVTPKQSLCDGQWHSVAVTIKQHILHLELDTDSSYTAGQIPFPPAS
TQEPLHLGGAPANLTTLRIPVWKSFFGCLRNIHVNHIPVPVTEALEVQGPVSLNGCPDQ

FIG._3K

```
catcc tccagaggac tggtgtttca cacgggcact aagaactcct ttatggctct
ttatctttca aaaggacgtc tggtctttgc actggggaca gatgggaaaa
aattgaggat caaaagcaag gagaaatgca atgatgggaa atggcacacg
gtggtgtttg gccatgatgg ggaaaagggg cgcttggttg tggatggact
gagggcccgg gagggaagtt tgcctggaaa ctccaccatc agcatcagag
cgccagttta cctgggatca cctccatcag ggaaaccaaa gagcctcccc
acaaacagct tgtgggatg cctgaagaac tttcagctgg attcaaaacc
cttgtatacc ccttcttcaa gcttcggggt gtcttcctgc ttgggtggtc
ctttggagaa aggcatttat ttctctgaag aaggaggtca tgtcgtcttg
gctcactctg tattgttggg gccagaattt aagcttgttt tcagcatccg
cccaagaagt ctcactggga tcctaataca catcggaagt cagcccggga
agcacttatg tgtttacctg gaggcaggaa aggtcacggc ctctatggac
agtggggcag gtgggacctc aacgtcggtc acaccaaagc agtctctgtg
tgatggacag tggcactcgg tggcagtcac cataaaacaa cacatcctgc
acctggaact ggacacagac agtagctaca cagctggaca gatccccttc
ccacctgcca gcactcaaga gccactacac cttggaggtg ctccagccaa
tttgacgaca ctgaggatcc ctgtgtggaa atcattcttt ggctgtctga
ggaatattca tgtcaatcac atccctgtcc ctgtcactga agccttggaa
gtccaggggc ctgtcagtct gaatggttgt
```

FIG._3L

FKLVFSIRPRSLTGILIHIGSQPGKHLCVYLEAGKVTASMDSGAGGTSTSVTPKQSLCDGQWHS
VAVTIKQHILHLELDTDSSYTAGQIPFPPASTQEPLHLGGAPANLTTLRIPVWKSFFGCLRNIH
VNHIPVPVTEALEVQGPVSLNGCPDQ

FIG._3M

```
tt  aagcttgttt  tcagcatccg  cccaagaagt  ctcactggga  tcctaataca
catcggaagt  cagcccggga  agcacttatg   tgtttacctg  gaggcaggaa
aggtcacggc  ctctatggac  agtggggcag   gtgggacctc  aacgtcggtc
acaccaaagc  agtctctgtg  tgatggacag   tggcactcgg  tggcagtcac
cataaaacaa  cacatcctgc  acctggaact   ggacacagac  agtagctaca
cagctggaca  gatccccttc  ccacctgcca   gcactcaaga  gccactacac
cttggaggtg  ctccagccaa  tttgacgaca   ctgaggatcc  ctgtgtggaa
atcattcttt  ggctgtctga  ggaatattca   tgtcaatcac  atccctgtcc
ctgtcactga  agccttggaa  gtccaggggc   ctgtcagtct  gaatggttgt
cctgaccagt
```

FIG._3N

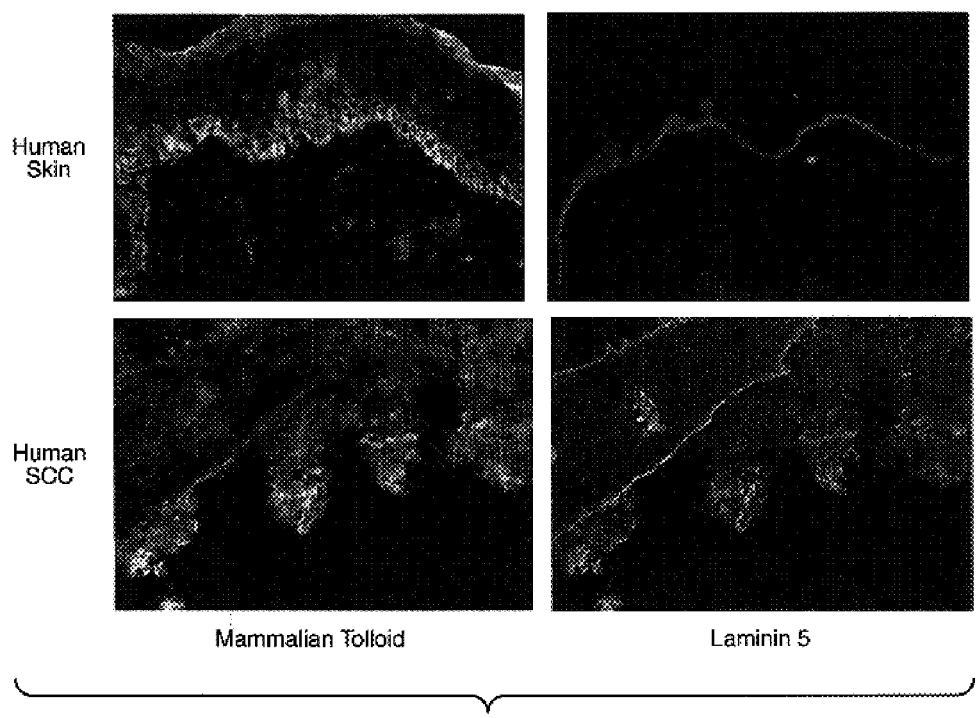
FIG._4

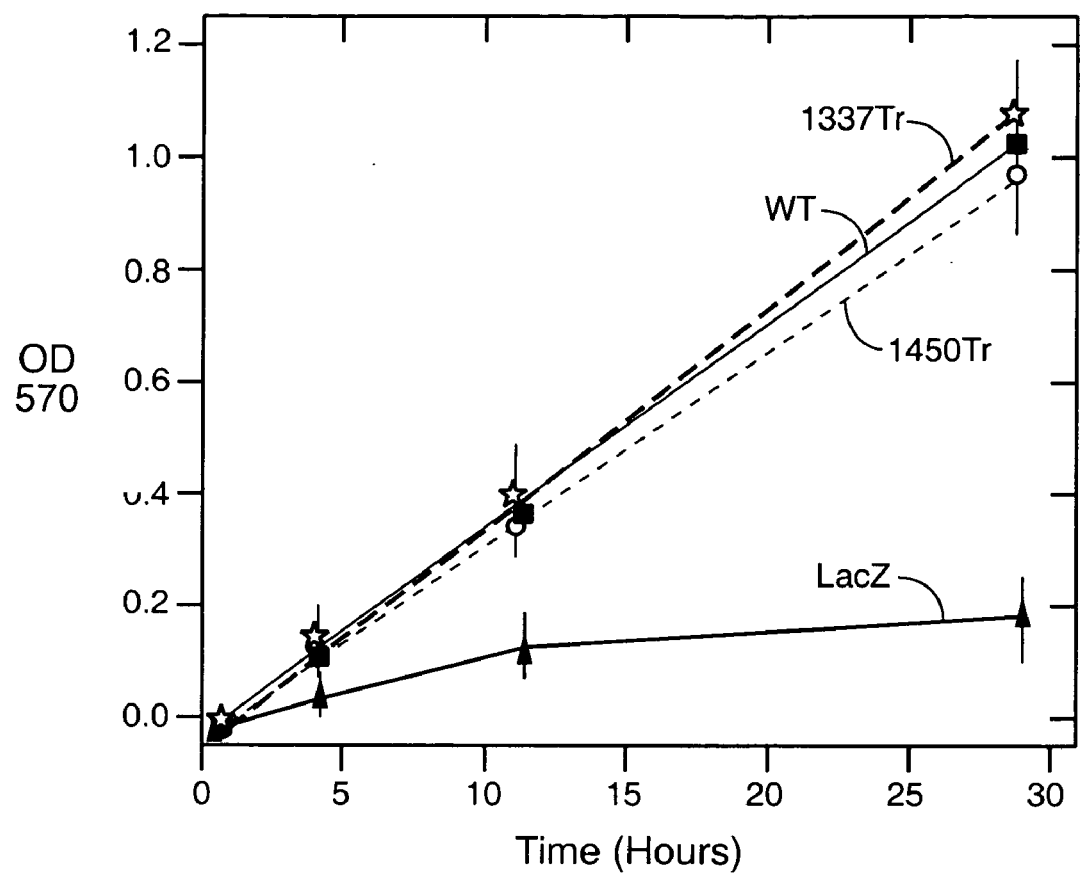
FIG._5

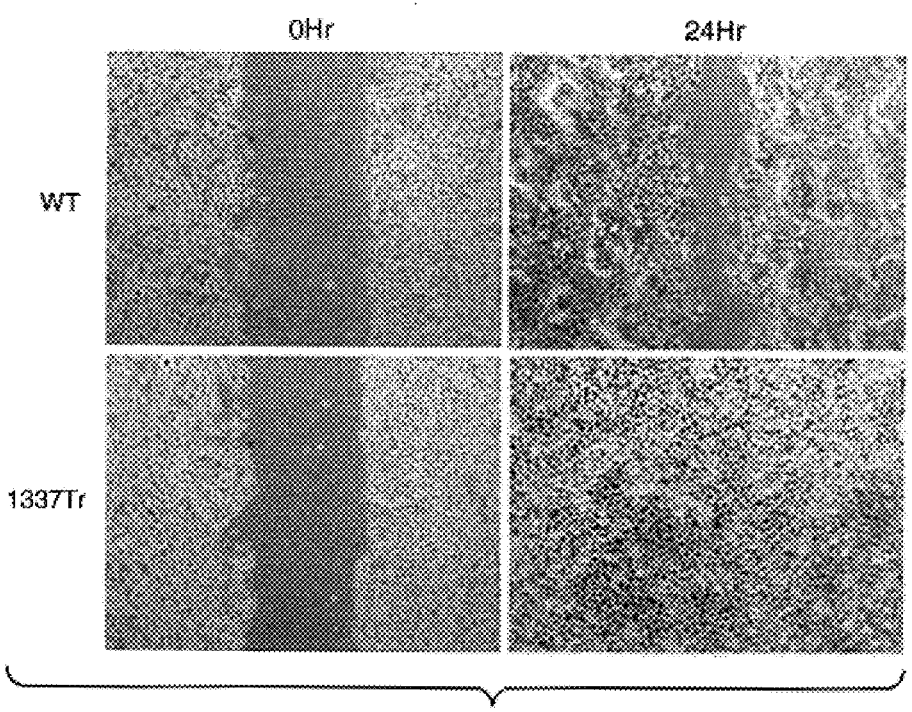
FIG._6
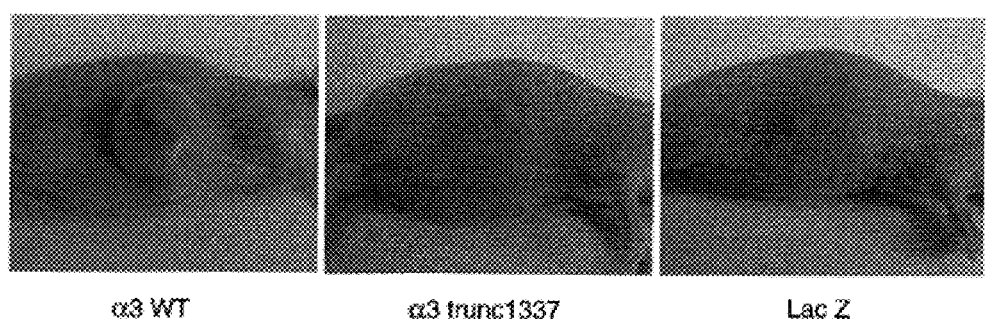
FIG._7

COMPOSITIONS AND METHODS FOR INHIBITING SQUAMOUS CELL CARCINOMA

STATEMENT AS TO FEDERALLY SPONSORED RESEARCH

This invention was made with Government support under contract AR47223 awarded by the National Institutes of Health. The Government has certain rights in this invention.

FIELD

The present invention relates to compositions and methods for detecting and inhibiting squamous cell carcinoma using agents that target the laminin 5 alpha 3 G4-G5 domain.

INTRODUCTION

Squamous cell carcinoma (SCC) is common form of cancer and is the second most common form of skin cancer in the United States. SCCs are highly invasive and metastatic. SCCs are associated with a comparatively high risk of recurrence, resulting in significant mortality. SCC can be diagnosed by biopsy. However, SCCs are typically not as distinct as basal cell carcinomas or melanomas, making detection and diagnosis difficult. Current methods of treatment, i.e. surgery, radiotherapy, and chemotherapy, require continued monitoring due to the metastatic nature of the disease. The development of alternative methods of detection and treatment is therefore desirable.

The compositions and methods described herein are directed towards identifying agents that can detect and inhibit proteins associated with SCC tumorigenesis. Of particular interest, are agents that interact with the laminin-5 alpha 3 chain G4 and/or G5 domains.

SUMMARY

Provided herein are compositions and methods useful for detecting and treating squamous cell carcinoma (SCC). The compositions generally comprise antibodies capable of binding a migration facilitating protein (MFP) of a laminin 5 alpha 3 chain G4 and/or G5 domain or subdomain. MFPs typically comprise 8, 9, 10 or more amino acids present in the laminin 5 alpha 3 G4 and/or 5 domains that do not comprise a recognized cleavage site for bone morphogenetic protein-1 (BMP-1) and BMP-1 related proteins. For example, MFPs can be generated comprising: (1) the G5 subdomain; (2) the G4 subdomain lying between amino acid 1358 and amino acid 1366; (3) the G4 subdomain lying between amino acid 1375 and amino acid 1390; (4) the G4 subdomain lying between amino acid 1399 and 1530; and, (5) the G4-5 subdomain lying between amino acid 1399 and amino acid 1713. As will be appreciated by a person of skill in the art, MFPs encoding other subdomains within the laminin 5 alpha 3 G4 and/or 5 domains can also be generated and used in the methods of the present invention. The compositions can include additional components, such as, detectable labels and a pharmaceutically acceptable carrier.

The methods generally involve administering a therapeutically effective amount of a composition comprising one or more antibodies capable of inhibiting SCC tumorigenesis to a patient diagnosed with SCC. Treatment of a patient diagnosed with SCC with the compositions described herein can be combined with other medical means for treating SCC, such as surgery, radiotherapy, and chemotherapy. The SCC can be selected from the group consisting of skin cancer, lung cancer, head cancer, gastric cancer, colorectal cancer, throat cancer, cancer of the urinary tract, cancer of the reproductive tract, esophageal cancer, and bronchiogenic carcinoma.

Also provided are methods that utilize the MFPs described above. In some embodiments, a method is provided for detecting the binding activity of a candidate agent in a sample that comprises the steps of:

(a) contacting the sample with an MFP under conditions effective to permit binding between the MFP and the candidate agent (if present); and, (b) detecting the binding of the candidate agent.

A number of different assays can be used to detect binding of the candidate agent. For example, in some embodiments, the candidate agent is labeled and binding determined directly. In other embodiments, the binding of the candidate agent is determined through the use of competitive binding assays in which the competitor is a binding moiety known to bind the MFP, i.e., an antibody. Displacement of the competitor by the candidate agent is an indication that the candidate agent is capable of binding the MFP.

Also provided herein are methods for screening for candidate agents that inhibit SCC tumorigenesis. In some embodiments, a method is provided for screening for candidate agents that inhibit SCC tumor development comprising the steps of:

a) subcutaneously injecting nude mice with a suspension comprising:
  i) Ras/IKB transformed epithelial cells;
  ii) a migration facilitating protein (MFP) of a laminin G4 and/or G5 domain or subdomain;
  iii) one or more candidate agents; and
b) determining the presence or absence of a tumor.

In some embodiments, a method is provided to evaluate the effect of a candidate SCC drug comprising administering the drug to a patient diagnosed with SCC and removing a cell sample from the patient. A number of different assays can be used to evaluate the effect of the candidate drug. For example, the expression profile of the cell sample can be determined and compared with an expression profile of a healthy individual. In some embodiments, the cell sample can be analyzed for the presence or absence of an MFP associated with SCC development before and after treatment with a candidate drug. In yet other embodiments, the size of the tumor before and after treatment with a candidate drug can be analyzed to determine if the drug is effective in inhibiting the invasion of nearby normal cells.

Also provided herein is a method for diagnosing SCC comprising removing a cell sample from an individual and analyzing the cell with one or more MFPs determined to be involved in SCC proliferation and/or metastasis.

These and other features of the compositions and methods described herein will become more apparent from the detailed description below.

BRIEF DESCRIPTION OF THE DRAWINGS

Aspects of the invention can be more fully understood with respect to the following drawings. In the drawings, similar elements are referenced with like numbers.

FIG. 1A provides a cartoon illustrating the G4 (1) and G5 (2) domains of the alpha 3 chain of laminin 5, including the cleavage recognition sites (1a, 1b, 1c) for bone morphogenetic protein-1 (BMP-1);

FIG. 1B illustrates exemplary embodiments of migration facilitating proteins (MFPs) that can be generated from the G4 domain;

FIG. 1C illustrates exemplary embodiments of migration facilitating proteins (MFPs) that can be generated from the G5 domain;

FIG. 1D illustrates exemplary embodiments of migration facilitating proteins (MFPs) that can be generated comprising amino acids present in both the G4 and G5 domains;

FIG. 2A illustrates the polynucleotide sequence for *Homo sapiens* laminin-related protein (LAMA3; GenBank accession number L34156; SEQ ID NO:1);

FIG. 2B illustrates the amino acid sequence for *Homo sapiens* laminin-related protein (LAMA3; GenBank accession number L34156; SEQ ID NO:2);

FIG. 2C illustrates the polynucleotide sequence for *Homo sapiens* laminin, alpha 3 transcript variant 1 (LAMA3; GenBank NM_198129; SEQ ID NO:3);

FIG. 2D illustrates the amino acid sequence for *Homo sapiens* laminin, alpha 3 transcript variant 1 (LAMA3; GenBank NM_198129; SEQ ID NO:4);

FIG. 2E illustrates the polynucleotide sequence for *Homo sapiens* laminin, alpha 3 transcript variant 2 (LAMA3; GenBank NM_000227 SEQ ID NO:5);

FIG. 2F illustrates the amino acid sequence for *Homo sapiens* laminin, alpha 3 transcript variant 2 (LAMA3; GenBank NM_000227 SEQ ID NO:6);

FIG. 2G illustrates the polynucleotide sequence for *Rattus norvegicus* laminin 5 alpha 3 (LAMA3; GenBank NM_173306; SEQ ID NO:7);

FIG. 2H illustrates the amino acid sequence for *Rattus norvegicus* laminin 5 alpha 3 (LAMA3; GenBank NM_173306; SEQ ID NO:8);

FIG. 2I illustrates the polynucleotide sequence for *Mus musculus* laminin, alpha 3 (LAMA3; GenBank XM 140451; SEQ ID NO:9);

FIG. 2J illustrates the amino acid sequence for *Mus musculus* laminin, alpha 3 (LAMA3; GenBank XM 140451; SEQ ID NO:10);

FIG. 3A illustrates an exemplary *Homo sapiens* amino acid sequence for the combined G4 and G5 domains (SEQ ID NO:11);

FIG. 3B illustrates an exemplary *Homo sapiens* polynucleotide sequence for the combined G4 and G5 domains (SEQ ID NO:12);

FIG. 3C illustrates an exemplary *Homo sapiens* amino acid sequence for the G5 domain (SEQ ID NO:13);

FIG. 3D illustrates an exemplary *Homo sapiens* polynucleotide sequence for the G5 domain (SEQ ID NO:14);

FIG. 3E illustrates an exemplary *Homo sapiens* amino acid sequence for the G4 subdomain delimited by amino acid 1356 through amino acid 1366 (SEQ ID NO:15);

FIG. 3F illustrates an exemplary *Homo sapiens* polynucleotide sequence for the G4 subdomain delimited by nucleotide 4067 through nucleotide 4099 (SEQ ID NO:16);

FIG. 3G illustrates an exemplary *Homo sapiens* amino acid sequence for the G4 subdomain delimited by amino acid 1375 through amino acid 1390 (SEQ ID NO:17);

FIG. 3H illustrates an exemplary *Homo sapiens* polynucleotide sequence for the G4 subdomain delimited by nucleotide 4124 through nucleotide 4171 (SEQ ID NO:18);

FIG. 3I illustrates an exemplary *Homo sapiens* amino acid sequence for the G4 subdomain delimited by amino acid 1399 through amino acid 1529 (SEQ ID NO:19);

FIG. 3J illustrates an exemplary *Homo sapiens* polynucleotide sequence for the G4 subdomain delimited by nucleotide 4196 through nucleotide 4588 (SEQ ID NO:20);

FIG. 3K illustrates an exemplary *Homo sapiens* amino acid sequence for a polypeptide spanning the G4 and G5 domain delimited by amino acid 1399 through amino acid 1713 (SEQ ID NO:21);

FIG. 3L illustrates an exemplary *Homo sapiens* polynucleotide sequence for a polynucleotide spanning the G4 and G5 domain delimited by nucleotide 4196 through nucleotide 5140 (SEQ ID NO:22);

FIG. 3M illustrates an exemplary *Homo sapiens* amino acid sequence for a polypeptide spanning the G5 domain delimited by amino acid 1560 through amino acid 1713 (SEQ ID NO:23);

FIG. 3N illustrates an exemplary *Homo sapiens* polynucleotide sequence for a polynucleotide spanning the G5 domain delimited by nucleotide 4679 through nucleotide 5140 (SEQ ID NO:24);

FIG. 4 depicts normal human skin epithelia cells and SCC epithelial derived tumor cells;

FIG. 5 illustrates the results from a migration assay comparing wild-type cells, and keratinocytes transformed with truncated versions of the laminin-5 alpha 3 chain;

FIG. 6 illustrates a scratch assay in which cells lacking the G4 and G5 domain (i.e. 1337TR) migrate more efficiently than cells expressing wild-type laminin-5 alpha 3 chain;

FIG. 7 illustrates a mouse model of human SCC. The left panel depicts tumor formation in nude mice transformed with RAS/IKB keratinocytes transformed with wild-type laminin-5 alpha 3 chain. The middle and right panels illustrate that SCC tumors are not formed in nude mice transformed with RAS/IKB laminin-5 negative keratinocytes (right panel) or with a laminin-5 construct lacking the G4 and G5 domains (middle panel).

DETAILED DESCRIPTION

It is to be understood that both the foregoing general description and the following detailed description are exemplary and explanatory only and are not restrictive of the inventions described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting. Unless defined otherwise, all technical and scientific terms used herein have the same meanings as commonly understood by one of ordinary skill in the art to which the invention belongs.

1. Definitions

As used herein, the following terms and phrases are intended to have the following meanings:

"Antibody" has its standard meaning and is intended to refer to intact molecules as to fragments thereof, such as Fab, F(ab')2, and Fv fragments, that are capable of binding an epitope.

"Cancer" has its standard meaning and is intended to refer to any malignant tumor of potentially unlimited growth that expands locally by proliferation and systemically by metastasis.

"Neoplasm" has its standard meaning and is intended to refer to the abnormal growth of a tissue, such as a tumor.

"Nucleobase" means those naturally occurring and those synthetic nitrogenous, aromatic moieties commonly found in the nucleic acid arts. Examples of nucleobases include purines and pyrimidines, genetically encoding nucleobases, analogs of genetically encoding nucleobases, and purely synthetic nucleobases. Specific examples of genetically encoding nucleobases include adenine, cytosine, guanine, thymine, and uracil. Specific examples of analogs of genetically encoding nucleobases and synthetic nucleobases include 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). 5-propynyl-uracil, 2-thio-5-propynyl-uracil. Other non-limiting examples of suitable nucleobases include those nucleobases illustrated in FIGS. 2(A) and 2(B) of U.S. Pat. No. 6,357,163, incorporated herein by reference in its entirety.

"Nucleoside" refers to a nucleobase linked to a pentose sugar. Pentose sugars include ribose, 2'-deoxyribose, 3'-deoxyribose, and 2', 3'-dideoxyribose.

"Nucleoside analog" refers to a nucleobase linked to a sugar, other than a pentose sugar. For example, a nucleobase linked to hexose.

"Nucleotide" refers to compound comprising a nucleobase, a pentose sugar and a phosphate. Thus, as used herein a nucleotide refers to a phosphate ester of a nucleoside, e.g., a triphosphate.

"Nucleobase Polymer or Oligomer" refers to two or more nucleobases that are connected by linkages that permit the resultant nucleobase polymer or oligomer to hybridize to a polynucleotide having at least a partially complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide nucleic acids or peptide nucleic acids. Polyamide nucleic acids and peptide nucleic acids are two different phrases used in the literature to describe the same molecule, abbreviated herein as PNA. Nucleobase polymers or oligomers can vary in size from a few nucleobases, for example, from 2 to 40 nucleobases, to several hundred nucleobases, to several thousand nucleobases, or more.

"Polynucleotides or Oligonucleotides" refer to nucleobase polymers or oligomers in which the nucleobases are linked by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

"Polynucleotide or Oligonucleotide Analog" refers to nucleobase polymers or oligomers in which the nucleobases are linked by a phosphate backbone comprising one or more sugar analogs or phosphate analogs. Typical oligonucleotide or polynucleotide analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani 1995, Chem. & Eng. News 4-5:1153; Dempey et al., 1995, J. Am. Chem. Soc. 117: 6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g. Elayadi et al., 2002, Biochemistry 41:9973-9981; Koshkin et al., 1998, J. Am. Chem. Soc. 120:13252-3; Koshkin et al., 1998, Tetrahedron Letters, 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190; all of which are incorporated herein by reference in their entireties).

"Polynucleotide or oligonucleotide mimic" refers to nucleobase polymers or oligomers in which the nucleobases are connected by a linkage other than a sugar-phosphate linkage or a sugar-phosphate analog linkage. Mimics with a specific linkage include peptide nucleic acids (PNAs) as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. Other types of mimics are described in the following publications: Lagriffoul et al., 1994, *Bioorganic & Medicinal Chemistry Letters*, 4: 1081-1082; Petersen et al., 1996, *Bioorganic & Medicinal Chemistry Letters*, 6: 793-796; Diderichsen et al, 1996, *Tett. Lett.* 37: 475-478; Fujii et al., 1997, *Bioorg. Med. Chem. Lett.* 7: 637-627; Jordan et al., 1997, *Bioorg. Med. Chem. Lett.* 7: 687-690; Krotz et al., 1995, *Tett. Lett.* 36: 6941-6944; Lagriffoul et al, 1994, *Bioorg. Med. Chem. Lett.* 4: 1081-1082; Diederichsen, U., 1997, *Bioorganic & Medicinal Chemistry 25 Letters*, 7: 1743-1746; Lowe et al., 1997, *J. Chem. Soc. Perkin Trans.* 1, 1: 539-546; Lowe et al., 1997, *J. Chem. Soc. Perkin Trans.* 11: 547-554; Lowe et al., 1997, *I. Chem. Soc. Perkin Trans.* 1 1:5 55-560; Howarth et al., 1997, *I. Org. Chem.* 62: 5441-5450; Altmann, K-H et al., 1997, *Bioorganic & Medicinal Chemistry Letters*, 7: 1119-1122; Diederichsen, U., 1998, *Bioorganic & Med. Chem. Lett.*, 8:165-168; Diederichsen et al., 1998, *Angew. Chem. mt. Ed.*, 37: 302-305; Cantin et al., 1997, *Tett. Lett.*, 38: 4211-4214; Ciapetti et al., 1997, *Tetrahedron*, 53: 1167-1176; Lagriffoule et al., 1997, *Chem. Eur. 1.'* 3: 912-919; Kumar et al., 2001, *Organic Letters* 3(9): 1269-1272; and the Peptide-Based Nucleic Acid Mimics (PENAMs) of Shah et al. as disclosed in WO 96/04000. All of which are incorporated herein by reference.

The oligonucleotides may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence.

"Protein" has its standard meaning and is intended to refer to at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acad. Sci. U.S.A. 89(20:9367-71 (1992)], generally depending on the method of synthesis. Thus "amino acid", or "peptide residue", as used herein means both naturally occurring and synthetic amino acids. For example, homophenylalanine, citrulline, and norleucine are considered amino acids for the purposes of the invention. "Amino acid" also includes imino acid residues such as proline and hydroxyproline. In addition, any amino acid representing a component of the variant proteins of the present invention can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R— or the S—, depending upon its composition and chemical configuration. Such derivatives generally have the property of greatly increased stability, and therefore are advantageous in the formulation of compounds which may have longer in vivo half lives, when administered by oral, intravenous, intramuscular, intraperitoneal, topical, rectal, intraocular, or other routes.

In some embodiments, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

"Squamous cell carcinoma" has its standard meaning and is intended to refer to any neoplasm or tumor of epithelial cells.

"Tumorigenesis" has its standard meaning and is intended to refer to the basic developmental processes that produce tumors. These basic properties include the ability to proliferate or invade nearby normal cells and the ability to migrate from the site where the tumor initiated, i.e. metastasis.

2. EXEMPLARY EMBODIMENTS

Provided herein are: (1) migration facilitating proteins (MFPs) derived from the laminin-5 α3 chain G4 and/or G5 domains; (2) antibodies which bind to MFPs, thereby inhibiting tumorigenesis of neoplastic epithelial cells; (3) methods for screening for agents, such as antibodies, small molecules, etc., that specifically bind one or more of the MFPs described herein; (4) methods for screening for agents that inhibit squamous cell carcinoma (SCC) tumor development using MFPs, (5) methods for diagnosing SCC; and, (6) methods for determining the efficacy of candidate agents used to treat SCC. All of these inventions rely upon MFPs, nucleic acids that encode MFPs and other molecules, such as antibodies, that bind MFPs.

Laminin-5 (formerly called kalinin, nicein, or BM6000) is a heterotrimeric extracellular matrix protein that is initially synthesized and secreted in an unprocessed form with an α3 chain of 200 kDa, a β3 chain of 140 kDA, and a γ2 chain of 155 kDA. (Marinkovich et al., 1992, *J. Biol. Chem.*, 267: 17900-17906). Laminin-5 is a component of the basal lamina, the structure that provides tissue integrity, as well as the foundation for migration, growth and differentiation of cells. It is therefore not surprising that processes that interfere with wild type functions of laminin-5 produce diseases in humans and other mammals.

Large deposits of laminin-5 are found at the leading edges of squamous cell carcinomas (SCCs). This deposition of laminin-5 is believed to serve as a substrate for tumor invasion (see, e.g., Pyke et al., 1995, *Canc. Res.* 55: 4132-4139; Berndt et al., 1997, *Invasion and Metastasis*, 17: 251-258). Increased laminin-5 immunoreactivity is indicative of a poor prognosis in patients with squamous cell carcinoma (SCC). Laminin-5 is also preferentially expressed by invading malignant cells of many human carcinomas in additions to SCCs, colon and mammary carcinomas (Pyke, et al., 1994, *Am. J. Pathol.* 145(4):782-791) and malignant gliomas (Fukushima et al., 1998, *Int. J. Cancer*, 76: 63-72).

Processing of extracellular matrix proteins by proteases is emerging as a key mechanisms in processes such as wound healing and tumor metastasis. Several proteases have been implicated in laminin-5-processing (see, e.g., Veitch et al., 2003, *J. Biol. Chem.*, 278: 15661-15668; and U.S. patent Pub. No. 2002/0076736). In fully formed tissues, laminin-5 is completely processed and is devoid of the G4 and G5 domains (Marinkovich et al., 1992, *J. Biol. Chem.*, 267: 17900-17906). Without being bound by theory, it appears that specific proteolytic processing can convert laminin-5 from a pro-migratory signal required for cell migration during tumor invasion and tissue remodeling to an adhesive substrate devoid of the G4 and G5 domains.

2.1 Migration Facilitating Sequences

Accordingly, provided herein are polynucleotide and amino acid sequences associated with SCC, herein termed "migration facilitating sequences" or "MFSs". The proteins having the various amino acid sequences are referred to herein as "migration facilitating proteins" or "MFPs". Association in this context means that the amino aicd and polynucleotide sequences are either differentially expressed or altered in SCCs or neoplastic epithelial cells as compared to normal epithelial tissue. "SCC" refers herein to any malignant neoplasm or tumor of epithelial cells. Specific examples of epithelial cells include squamous cells, squamous carcinoma cells, keratinocytes, mucosal epithelial cells, such as oral mucosal cells, gastrointestinal epithelial cells, corneal epithelium of the eye, and epithelial cells of the urinary and reproductive tract. Specific examples of SCC carcinomas arising from neoplastic epithelial cells include skin, lung, head, neck, oral, gastric, colorectal, throat, urinary tract, reproductive tract, esophageal, etc.

SCC is commonly sun-induced, i.e., actinically derived SCC. SCC can also result from transplant or invasive surgery, or follow other immunosuppressive situations. Chronic inflammation can lead to development of SCC at the site of inflammation, e.g., a burn or scar, Majolin's ulcer, etc. SCC can be virally induced, for example, SCC can result from human papillomavirus-induced (HPV) infection. SCC can include adenoid (acantholytic) SCC, spindle cell SCC, verrucous carcinoma (VC), keratoacanthoma (KA), nodular SCC periungual SCC, and other epithelial carcinomas.

MFSs can include both polynucleotide and amino acid sequences. In some embodiments, the MFSs are recombinant polynucleotides. By the term "recombinant polynucleotide" herein is meant polynucleotides, originally formed in vitro, in general, by the manipulation of the polynucleotide by polymerases and endonucleases, in a form not normally found in nature. Thus, an isolated polynucleotide, in a linear form, or an expression vector formed in vitro by ligating polynucleotide molecules that are not normally joined, are both considered recombinant for the purposes of this invention. It is understood that once a recombinant polynucleotide is made and reintroduced into a host cell or organism, it will replicate non-recombinantly, i.e. using the in vivo cellular machinery of the host cell rather than in vitro manipulations; however, such polynucleotides, once produced recombinantly, although subsequently replicated non-recombinantly, are still considered recombinant for the purposes of the invention.

As will be appreciated by those in the art, and more fully outlined below, MFSs comprising polynucleotides are useful in a variety of applications, including diagnostic applications, where they can be used as hybridization probes to detect MFSs in SCCs, as well as in therapeutic applications, such as the development of antisense sequences that can be used to affect the expression and activity of MFPs in SCCs.

MFSs include those that are up-regulated, (e.g., expressed at a higher level), as well as those that are down-regulated, (e.g., expressed at a lower level) in SCCs. MFSs also include sequences that have been altered (i.e. truncated sequences or sequences with a one or more mutations, such as point mutations, deletions, insertions, etc.) and show either the same expression profile or an altered profile. In some embodiments, the MFSs are from humans. However, as will be appreciated by a person of skill in the art, MFSs from other organism may be useful in animal models of disease and drug evaluation. Thus, other MFSs are provided. For example, MFSs can be obtained from vertebrates, including mammals, such as rodents (rats, mice, hamsters, guinea pigs, etc.), primates, farm animals (including sheep, goats, pigs, cows, horses, etc), as well invertebrates, such as *Drosophila*. MFSs from other organisms may be obtained using the techniques outlined below.

In some embodiments, MFSs are those that are altered but show either the same expression profile or an altered profile as compared to normal epithelial tissue of the same differentiation stage. "Altered MFSs" as used herein refers to sequences which are truncated, contain insertions or contain point mutations.

An MFS can be initially identified by substantial nucleic acid and/or amino acid sequence homology to the MFS's outlined herein. Such homology can be based upon the overall oligonucleotide or amino acid sequence, and is generally determined, using either homology programs or hybridization conditions. As is known in the art, a number of different programs are available for determining polynucleotide or amino acid sequence homology including sequence based alignment programs, sequence homology based alignment programs, structural alignment programs etc. Non-limiting examples of sequence-based alignment programs include Smith-Waterman searches (Smith & Waterman, *Adv. Appl. Math.* 2:482 (1981)), Needleman-Wunsch (Needleman & Wunsch, *J. Mol. Biol.* 48:443 (1970)), Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and Gene-Wise. Sequence homology based alignment methods are described in Altschul et al. (Altschul et al., *J. Mol. Biol.* 215(3):403 (1990)). Examples of structural alignment programs include VAST from the NCBI; SSAP (Orengo and Taylor, *Methods Enzymol* 266(617-635 (1996)) SARF2 (Alexandrov, *Protein Eng* 9(9):727-732. (1996)) CE (Shindyalov and Boume, *Protein Eng* 11(9):739-747. (1998)); (Orengo et al., *Structure* 5(8):1093-108 (1997); Dali (Holm et al., *Nucleic Acid Res.* 26(1):316-9 (1998), Computerized implementations of some of the above described algorithms are also available (e.g., BLASTx, BLAST, GAP, BESTFIT, FASTA, and TFASTA in the Wisconsin Genetics Software Package, Genetics Computer Group, 575 Science Drive, Madison, Wis.); the Best Fit sequence program described by Devereux et al., *Nucl. Acid Res.* 12:387-395 (1984).

Polynucleotide homology can also be determined through hybridization studies; see for example Maniatis et al., Molecular Cloning: A Laboratory Manual, 2d Edition, 1989, and Short Protocols in Molecular Biology, ed. Ausubel, et al., both of which are hereby incorporated by reference. Generally, stringent hybridization conditions are selected, although less stringent hybridization conditions can be used. Typically, stringent conditions are selected to be about 5-10/C lower than the thermal melting point (Tm) for the specific sequence at a defined ionic strength pH. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993).

In some embodiments, MFSs are polynucleotides. Polynucleotides comprising MFSs can be generated from either a full length genomic and/or cDNA polynucleotide encoding a laminin-5 α3 chain. In some embodiments, MFSs are generated from the human α3 chain of laminin-5 (Ryan et al., 1994, J. Biol. Chem., 269: 22779-22787; Gen Bank Accession No. NM_000227). MFSs of various lengths spanning the G4 and/or G5 domains can be generated. For example, an polynucleotide spanning a subdomain of the G4 domain of the human α3 chain of laminin-5 can be generated by starting at nucleotide position 4196 and ending at nucleotide 4588. An oligonucleotide spanning the G5 domain of the human α3 chain of laminin-5 can be generated by starting at nucleotide position 4590 and ending at nucleotide 5140. An oligonucleotide spanning a subdomain of the G4 domain and the entire G5 domain of the human α3 chain of laminin-5 can be generated by starting at nucleotide position 4196 and ending at nucleotide 5140.

The exact number of nucleotides or nucleotide analogs chosen will vary depending on the sequence of the nucleotides selected and the presence of nucleotides encoding amino acids that comprise antigenic determinants. By "epitope" or "determinant" "or antigenic determinant" herein is meant a portion of a protein that can generate and/or bind an antibody or T-cell receptor in the context of MHC. For example, the presence of antigenic determinants within the G4 and G5 domains can be identified by searching databases for MHC ligands and peptide motifs (Rammensee, H., et al. (1999) Immunogenetics, 50:213-219). This information can be used to generate MFSs comprising MHC epitopes. Typically, epitopes recognized by MHC class I molecules comprise between 8 and 11 amino acids, thus, an MFS encoding an MHC class I epitope can range between 24 to 33 nucleotides. Viral peptides recognized by MHC class II molecules comprise between 10 to 20 amino acids, thus, an MFS encoding an MHC class II epitope can range between 30 to 60 nucleotides (Fundamental Immunology, 4th edition, W. E. Paul, ed., Lippincott-Raven Publishers, 1999, Chapter 39, pp 1295-1334). In other embodiments, MFSs range between 24 to 1050, or from 60 to 300 nucleotides, or from 60 to 405 nucleotides, or from 60 to 555 nucleotides, or from 60 to 600 nucleotides, or from 60 to 750 nucleotides, or from 60 to 900 nucleotides or from 60 to 1050 nucleotides. In yet other embodiments, MFSs range from 150 to 300 nucleotides, or from 150 to 405 nucleotides, or from 150 to 450 nucleotides, or from 150 to 525 nucleotides, or from 150 to 600 nucleotides, or from 150 to 750 nucleotides, or from 150 to 1050 nucleotides, or from 300 to 600 nucleotides, or from 300 to 900 nucleotides, or from 300 to 1050 nucleotides.

2.2 Migration Facilitating Proteins

In some embodiments, "migration facilitating proteins" or "MFPs" are generated from the amino acid sequence encoding the laminin-5 α3 G4 and/or G5 domains or subdomains thereof. "MFPs" are proteins that are capable of supporting migration of nearby tissue or tissue located at distal points in the body by neoplastic epithelial cells. MFPs also can be recombinant. A "recombinant MFP protein" is a protein made using recombinant techniques, i.e. through the expression of a recombinant oligonucleotide as described above. A recombinant protein is distinguished from a naturally occurring protein by at least one or more characteristics. For example, the protein may be isolated or purified away from some or all of the proteins and compounds with which it is normally associated in its wild type host, and thus may be substantially pure. Generally, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an MFP from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In some embodiments, MFPs are generated from the G4 and G5 domains of the human α3 chain of laminin-5 (see FIG. 1A). MFPs of various lengths spanning the G4 and/or G5 domains can be generated. FIG. 1B illustrates an exemplary embodiment of the generation of MFPs from the G4 domain. As illustrated in FIGS. 1B-D, a number of MFPs can be generated from the G4 and/or G5 domains comprising varying numbers of amino acids or amino acid analogs. The exact number of amino acids or amino acid analogs chosen will vary depending on the sequence of the amino acids selected, the presence of bone morphogenetic-1 cleavage sites, and the presence of amino acids comprising antigenic determinants.

As discussed above, the presence of antigenic determinants within the G4 and G5 domains can be identified by searching databases for MHC ligands and peptide motifs (Rammensee, H., et al. (1999) Immunogenetics, 50:213-219). This information can be used to identify MHC epitopes. Typically, epitopes recognized by MHC class I molecules comprise between 8 and 11 amino acids while epitopes recognized by MHC class II molecules comprise between 10 to 20 amino acids (*Fundamental Immunology*, 4th edition, W. E. Paul, ed., Lippincott-Raven Publishers, 1999, Chapter 39, pp 1295-1334). Thus, in some embodiments, MFPs range between 8 to 11. In other embodiments, MFPs range between 10 to 20 amino acids. In other embodiments, MFPs range from 8 to 350 amino acids. In still other embodiments, MFPs range between 20 to 100 amino acids, or from 20 to 135 amino acids, or from 20 to 185 amino acids, or from 20 to 200 amino acids, or from 20 to 250 amino acids, or from 20 to 300 amino acids or from 20 to 350 amino acids. In yet other embodiments, MFPs range from 50 to 100 amino acids, or from 50 to 135 amino acids, or from 50 to 150 amino acids, or from 50 to 175 amino acids, or from 50 to 200 amino acids, or from 50 to 250 amino acids, or from 50 to 350 amino acids, or from 100 to 200 amino acids, or from 100 to 300 amino acids, or from 100 to 350 amino acids.

The MFPs may be unprocessed or processed. As used herein "unprocessed" refers to an MFP that is still associated with the laminin-5 α3 chain. By "processed" herein is meant that the MFP is dissociated from the laminin-5 α3 chain.

FIG. 1B illustrates an exemplary embodiment of MFPs that can be generated from the G4 domain. FIG. 1B depicts 3 MFPs: MFP 1, MFP 2, And MFP 3. Known cleavage sites for bone morphogenetic protein-1 (BMP-1) are indicated by the solid boxes labeled 1a, 1b, and 1c (see U.S. patent Pub. No. 2002/0076736). As illustrated in FIG. 1B, the MFPs described herein do not comprise cleavage sites for bone morphogenetic protein-1 (BMP-1) or related BMP-1 proteins. As will be appreciated by a skilled artisan, other MFPs (MFPs 4) can be generated from the G4 domain, comprising from 8 up to 130 amino acids.

FIG. 1C illustrates an exemplary embodiment of MFPs that can be generated from the G5 domain. As illustrated in FIG. 1C, one MFP can be made, i.e. MFP 5 spanning the entire G5 domain. In other embodiments one MFP can be made, i.e. MFP 6, that spans a subdomain of the G5 domain. Alternatively, a number of MFPs, i.e. MFPs 7, can be made comprising from 8 up to 182 amino acids.

FIG. 1D illustrates an exemplary embodiment of MFPs that can be generated from the G5 and the G5 domain. As illustrated in FIG. 1D, one MFP can be made, i.e. MFP 8, spanning the G4-G5 domain. As illustrated in FIG. 1D, MFP 8 does not contain cleavage sites for BMP-1 or related BMP-1 proteins. Alternatively, a number of MFPs, i.e., MFPs 9, can be made comprising from 8 up to 315 amino acids.

2.3 Expression Systems

MFSs polynucleotides encoding MFPs can be used to make a variety of expression vectors to express MFPs which can then be used in the diagnostic, screening and therapeutic applications described below. The expression vectors may be either self-replicating extrachromosomal vectors or vectors which integrate into a host genome. Generally, these expression vectors include transcriptional and translational regulatory nucleic acid operably linked to the oligonucleotide encoding the MFP protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

An oligonucleotide is "operably linked" when it is placed into a functional relationship with another olignonucleotide sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the MFP protein; for example, transcriptional and translational regulatory nucleic acid sequences from *Bacillus* are preferably used to express the MFP protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

MFPs are produced by culturing a host cell transformed with an expression vector containing an oligonucleotide encoding an MFP, under the appropriate conditions to induce or cause expression of the MFP. The conditions appropriate for MFP expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are primary human keratinocytes, although other cells also can be used, i.e. *Drosophila melanogaster* cells, *Saccharomyces cerevisiae* and other yeasts, *E. coli, Bacillus subtilis,* 293 cells, CHO, other human cell and cell lines.

In some embodiments, the MFPs are expressed in mammalian cells. Mammalian expression systems are also known in the art, and include retroviral systems. A preferred expression vector system is a retroviral vector system such as is generally described in Dajee et al., 2003, *Nature,* 421: 639-643, which is incorporated herein by reference in its entirety. Of particular use as mammalian promoters are the promoters from mammalian viral genes, since the viral genes are often highly expressed and have a broad host range. Examples include, but are not limited to, the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

For example, the full length laminin −5 α3 cDNA can be ligated into a pENTR1A™ vector (Invitrogen). The full length laminin −5 α3 cDNA can be cleaved and the PCR used to obtain a MF oligonucleotide sequence from the G4 and/or G5 domain. The resulting PCR product can be ligated into a pENTR1A™ vector and the cloning product confirmed by sequencing. The cloned product can then be transferred from the pENTR1A™ vector to a Gateway adapted LSRZ retroviral vector through lambda phage recombination. See Dajee et al., 2003, *Nature,* 421: 639-643.

In some embodiments, MFPs are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the MFP in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

MFS's and MFPs can be identified as described in the examples. For example, in a specific embodiment, various oligonucleotides can be generated from the G4 and G5 domain of the human laminin-5 α3 and subcloned into a retroviral vector. The resulting retroviral vectors can be transduced into cell cultures and the cells analyzed for cell scattering and cell migration (see e.g., Examples and FIGS. 5 and 6; see also Ryan, et al., 1994, *J. Biol. Chem.,* 269: 22779-22787). Alternatively, laminin-5 negative primary human keratinocytes co-expressing Ras, a stable NF-κB repressor mutant of IκBα (i.e. IKB), and one or more MFS(s) can be retrovirally transduced and used to regenerate human skin on immune deficient mice (i.e. nude mice). The subsequent development of neoplasms can be monitored and compared to wild type mice (see e.g., Examples, FIG. 7; and Dajee et al., 2003, Nature, 421:639-643).

In some embodiments, matrigel, which contains heparin sulfate proteoglycan, is used as a matrix for the suspension of RAS/IKB transformed keratinocytes prior to subcutaneous injection into nude mice. In other embodiments, MFPs can be suspended in matrigel prior to injection of RAS/IKB transformed keratinocytes.

In some embodiments, MFPs are purified or isolated after expression. MFPs may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the MFP may be purified using a standard anti-MFP antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the MFP protein. In some instances no purification will be necessary.

2.4 Antisense Sequences

The MFSs and MFPs can be used in a variety of different ways. In some embodiments, MFSs can be used to make antisense therapeutic agents that affect the expression and activity of MFPs. Antisense technology relies on the modulation of expression of a target protein through the specific binding of an antisense sequence to a target sequence encoding the target protein or directing its expression. (See, e.g., Agrawal, S., ed., 1996, Antisense Therapeutics, Humana Press Inc., Totawa N.J.; Alama et al. (1997) Pharmacol Res. 36(3):171-178; Crooke, S. T., 1997, Adv. Pharmacol. 40:1-49; and Lavrosky et al., 1997, Biochem. Mol. Med. 62(1):11-22.). Antisense sequences are nucleic acid sequences capable of specifically hybridizing to at least a portion of a target sequence. Antisense sequences can bind to cellular mRNA or genomic DNA, blocking translation or transcription and thus interfering with expression of a targeted protein product. Antisense sequences can be any nucleic acid material, including DNA, RNA, or any nucleic acid mimics or analogs. (See, e.g., Rossi et al., 1991, Antisense Res. Dev. 1(3):285-288; Pardridge et al., 1995, Proc. Nat. Acad. Sci. 92 (12):5592-5596; Nielsen, P. E. and G. Haaima, 1997, Chem. Soc. Rev. 96:73-78; and Lee et al., 1998, Biochemistry 37 (3):900-1010.). Delivery of antisense sequences can be accomplished in a variety of ways, such as through intracellular delivery using an expression vector. Site-specific delivery of exogenous genes is also contemplated, such as techniques in which cells are first transfected in culture and stable transfectants are subsequently delivered to the target site.

Typically, antisense oligonucleotides between 15 to 25 nucleobases or nucleobase analogs are capable of producing the desired therapeutic effect, i.e., direct disruption of translation of an MFP. In addition, chemically reactive groups, such as iron-linked ethylenediamine-tetraacetic acid (EDTA-Fe), can be attached to antisense oligonucleotides, causing cleavage of the RNA at the site of hybridization. These and other uses of antisense methods to inhibit the in vitro translation of genes are well known in the art (see, e.g., Marcus-Sakura (1988) Anal. Biochem. 172:289).

In some embodiments, antisense oligonucleotides are designed such that they disrupt the translation of the laminin-5 α3 chain. In other embodiments, antisense oligonucleotides are designed such that they disrupt the translation of an MFP from the G4 domain or subdomain thereof. In still other embodiments, antisense oligonucleotides are designed such that they disrupt the translation of an MFP from the G5 domain or subdomain thereof. In yet other embodiment, antisense oligonucleotides are designed such that they disrupt the translation of an MFP from the G4 and G5 domain or subdomain thereof.

Delivery of antisense agents can be achieved intracellularly through using a recombinant expression vector such as a chimeric virus or a colloidal dispersion system which, upon transcription, produces a sequence complementary to at least a portion of the cellular sequence encoding the target protein (see, e.g., Slater et al., 1998, J. Allergy Cli. Immunol. 102 (3): 469-475). Delivery of antisense sequences can also be achieved through various viral vectors, including retrovirus and adeno-associated virus vectors. (See, e.g., Miller, 1990, Blood, 76: 271; and Uckert and Walther, 1994, Pharacol. Ther., 63(3): 323-347). Suitable viral vectors include, but are not limited to, adenoviruses, herpes viruses, vaccinia, and RNA viruses such as retroviruses.

Retroviral vectors can be derivatives of murine or avian retrovirus. Retroviral vectors can be made target-specific by inserting, for example, a polynucleotide encoding a protein or proteins such that the desired ligand is expressed on the surface of the viral vector. The ligand can be a glycolipid carbohydrate or protein. Preferred targeting can also be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide. See, e.g, WO 91/04753.

Other delivery mechanisms that can be used for delivery of antisense sequences to target cells include colloidal dispersion and liposome-derived systems, artificial viral envelopes, and other systems available to one of skill in the art (see, e.g., Rossi, 1995, Br. Med. Bull. 51 (1): 217-225; Morris et al., 1997, Nucl. Acids Res. 25 (14): 2730-2736; Boado et al., 1998, J. Pharm. Sci. 87 (11): 1308-1315; and WO 90/10448). For example, delivery systems can make use of macromolecule complexes, nanocapsules, microspheres, beads, and lipid-based systems including oil-in-water emulsions, micelles, mixed micelles, and liposomes.

2.5 Antibodies

In some embodiments, the MFPs are used to generate antibodies that can be used in the screening and therapeutic applications described herein. Preferably, the MFP should comprise at least one epitope or determinant. In some embodiments, the epitope is unique; that is, antibodies generated to a unique epitope show little or no cross-reactivity. The term "antibody" can include polyclonal antibodies, monoclonal antibodies, chimeric antibodies, antibody fragments, such as Fab, $Fab_2$, single chain antibodies (Fv for example) etc., either produced by the modification of whole antibodies or those synthesized de novo using recombinant DNA technologies.

MFPs can be evaluated to determine regions of immunogenicity. As discussed above, methods of analysis and epitope selection are well-known in the art. Analysis and selection can also be accomplished, for example, by various software packages, such as LASERGENE NAVIGATOR software (DNASTAR; Madison, Wis.). The polypeptides or fragments used to induce antibodies should be antigenic, but need not necessarily be biologically active. An antigenic fragment or polypeptide is at least 5 amino acids in length, more preferably, at least 10 amino acids in length, and most preferably, at least 15 amino acids in length. It is preferable that the antibody-inducing fragment or polypeptide is identical to at least a portion of the amino acid sequence of the G4 and/or G5 domain, or subdomains thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor, and antibodies can be produced against the chimeric molecule.

Methods for the production of antibodies are well-known in the art. For example, various hosts, including goats, rabbits, rats, mice, humans, and others, may be immunized by injection with the MFP or any immunogenic fragment or peptide thereof. Depending on the host species, various adjuvants may be used to increase immunological response. Such adjuvants include, but are not limited to, Freund's adjuvant, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

Monoclonal and polycolonal antibodies can be prepared using any technique which provides for the production of antibody molecules by continuous cell lines in culture. Techniques for in vivo and in vitro production are well-known in the art (see, e.g., Pound, J. D., 1998, *Immunochemical Protocols*, Humana Press, Totowa N.J.; Harlow, E. and D. Lane, 1988, Antibodies, A Laboratory Manual, Cold Spring Harbor Laboratory, New York). The production of chimeric antibodies is also well-known, as is the production of single-chain antibodies (see, e.g., Morrison et al., 1984, *Proc. Natl. Acad. Sci.* 81: 6851-6855; Neuberger et al., 1984, *Nature*, 312: 604-608; Takeda et al., 1985, *Nature*, 314: 452-454). Antibodies with related specificity, but of distinct idiotypic composition, may be generated, for example, by chain shuffling from random combinatorial immunoglobin libraries (see, e.g., Burton, 1991, *Proc. Natl. Acad. Sci.* 88: 11120-11123).

Antibodies may also be produced by inducing in vivo production in the lymphocyte population or by screening immunoglobulin libraries or panels of highly specific binding reagents (see, e.g., Orlandi et al., 1989, *Proc. Natl. Acad. Sci.* 86: 3833-3837; Winter, G. and C. Milstein, 1991, *Nature*, 349: 293-299). Antibody fragments which contain specific binding sites for the target polypeptide may also be generated. Such antibody fragments include, but are not limited to, F(ab')$_2$ fragments, which can be produced by pepsin digestion of the antibody molecule, and Fab fragments, which can be generated by reducing the disulfide bridges of the F(ab')$_2$ fragments. Alternatively, Fab expression libraries may be constructed to allow rapid and easy identification of monoclonal Fab fragments with the desired specificity (see, e.g., Huse et al., 1989, *Science*, 254: 1275-1281).

In some embodiments, the antibodies are bispecific antibodies. Bispecific antibodies are monoclonal, preferably human or humanized, antibodies that have binding specificities for at least two different antigens. In the present case, one of the binding specificities is for a MFP, and the other one is for any other antigen, such as a cell-surface protein or receptor or receptor subunit, preferably one that is tumor specific.

In some embodiments, the antibodies to MFPs are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin (Jones et al., 1986, *Nature*, 321: 522-525; Riechmann et al., 1988, *Nature*, 332: 323-329; and Presta, 1992, *Curr. Op. Struct. Biol.*, 2: 593-596).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., 1986, *Nature*, 321: 522-525; Riechmann et al., 1988, *Nature*, 332: 323-329; Verhoeyen et al., 1988, *Science*, 239: 1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, 1991, *J. Mol. Biol.*, 227: 381; Marks et al., 1991, *J. Mol. Biol.*, 222: 581). The techniques of Cole et al. and Boemer et al. are also available for the preparation of human monoclonal antibodies (Cole et al., 1985, Monoclonal Antibodies and Cancer Therapy, Alan R. Liss, p. 77, and Boemer et al., 1991, *J. Immunol.*, 147(1): 86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., 1992, *Bio/Technology*, 10: 779-783; Lonberg et al., 1994, *Nature*, 368: 856-859; Morrison, 1994, *Nature*, 368: 812-13; Fishwild et al., 1996, *Nature Biotechnology*, 14: 845-51; Neuberger, 1996, *Nature Biotechnology*, 14: 826; Lonberg and Huszar, 1995, *Intern. Rev. Immunol.* 13 65-93.

Antibodies can be tested for anti-MFP activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art (see, e.g., Harlow and Lane, supra). Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed (see, e.g. Maddox et al., 1983, *J Exp Med*, 158: 1211).

Once made, the antibodies can be used to identify MFPs in a sample, e.g., from biopsied tissue, etc. The amount of MFPs or mRNAs encoding MRPs can be determined using methods well known in the art, including but not limited to, quantitative image analysis, and reverse transcriptase polymerase chain reaction (RT-PCR) using portions of the biopsied tissue. Quantitation of mRNA corresponding to MFPs, can be determined by a competition reaction using equal volumes of the patient sample run against a series of decreasing known concentrations, e.g., of a mimic or mutant cDNA fragment.

MFP antibodies as described herein, are capable of specifically binding to MFPs. By "specifically binding" herein is meant that the antibodies bind to the protein with a binding constant in the range of at least $10^{-4}$-$10^{-9}$ M$^{-1}$, preferably in the range of $10^{-4}$-$10^{-6}$ M$^{-1}$, with a preferred range being $10^{-7}$-$10^{-9}$ M$^{-1}$.

In some embodiments, antibodies to MFPs are capable of reducing or eliminating the biological activity or function of the MFP(s). That is, the addition of anti-MFP antibodies (i.e., polyclonal or monoclonal) to SCC or neoplastic epithelial cells expressing a MFP reduces or eliminates the MFP activity. Generally, at least a 25% decrease in activity is preferred, with at least about 50% being particularly preferred and about a 95-100% decrease being especially preferred.

In some embodiments, antibodies to MFPs are conjugated to a therapeutic moiety. For example, the therapeutic moiety can be an agent inhibit enzymatic activity such as protease or protein kinase activity associated with SCC. In other embodiments, the therapeutic moiety can be a cytotoxic agent. Cytotoxic agents are numerous and varied and include, but are not limited to, radiochemicals, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like.

2.6 Diagnosis and Therapy

The MFSs and MFPs can be used in a variety of different ways. For example, the MFSs and MFPs can be used in diagnostic assays, screening assays, and in therapeutic application. In some embodiments, the MFPS and antibodies to MFPs are used diagnostic markers for the detection of SCC. Detection of MFPs in putative SCC tissue or patients allows for a determination or diagnosis of SCC. To detect or diagnose SCC, baseline values for the expression or activity of MFPs are established in order to provide a basis for the diagnosis and/or prognosis of SCC in a patient. In some embodiments, this is accomplished by combining body fluids, tissue biopsies, or cell extracts taken from normal subjects with one or more antibody(ies) to a MFP under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified MFP. Standard values obtained from normal samples may be compared with values obtained from samples from subjects suspected of having SCC. Deviation between standard and subject values establishes the presence of or predisposition to the disease state.

In other embodiments, the expression levels of genes are determined for different cellular states in the SCC phenotype; that is, the expression levels of genes in normal tissue and in SCC tissue are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or SCC tissue.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus lymphoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the MF protein and standard immunoassays (ELISAs, etc.) or other techniques, including mass spectroscopy assays, 2D gel electrophoresis assays, etc. Thus, the proteins corresponding to MF genes, i.e. those identified as being important in a SCC phenotype, can be evaluated in a SCC diagnostic test.

Numerous methods known to those of ordinary skill in the art find use in diagnosisng SCC. For example, in some embodiments, proteins can be obtained from a sample or a patient are separated by electrophoresis on a gel (typically a denaturing and reducing protein gel, but may be any other type of gel including isoelectric focusing gels and the like). Following separation of the proteins, MFPs can be detected by immunoblotting with antibodies raised against the MFPs. Methods of immunoblotting are well known to those of ordinary skill in the art.

In some embodiments, antibodies to the MFPs find use in in situ imaging techniques. In this method cells are contacted with from one to many antibodies to MFP(s). Following washing to remove non-specific antibody binding, the presence of the antibody or antibodies is detected. In one embodiment the antibody is detected by incubating with a secondary antibody that contains a detectable label. In another method the primary antibody to the MFP(s) contains a detectable label. In another preferred embodiment each one of multiple primary antibodies contains a distinct and detectable label. This method finds particular use in simultaneous screening for a plurality of MFPs. As will be appreciated by one of ordinary skill in the art, numerous other histological imaging techniques are useful in the invention.

In some embodiments the label is detected in a fluorometer which has the ability to detect and distinguish emissions of different wavelengths. In addition, a fluorescence activated cell sorter (FACS) can be used in the method.

In some embodiments, in situ hybridization of labeled MF nucleic acid probes to tissue arrays is done. For example, arrays of tissue samples, including SCC tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes which indicate the diagnosis may differ from those which indicate the prognosis.

In a preferred embodiment, the MF proteins, antibodies, nucleic acids, and cells containing MF sequences are used in prognosis assays. In some embodiments, gene expression profiles can be generated that correlate to SCC severity, in terms of long term prognosis. Again, this may be done on either a protein or gene level, with the use of genes being preferred. In some embodiments, MF probes are attached to solid supports for the detection and quantification of MF sequences in a tissue or patient. The assays proceed as outlined for diagnosis.

The efficacy of therapeutic agents, such as antibodies and/or other candidate drugs also can be determined using the diagnostic assays described above. As will be appreciated by a person of skill in the art, assays to determine the efficacy of a therapeutic agent require the establishment of baseline values. In some embodiments, this is accomplished by combining body fluids, tissue biopsies, or cell extracts taken from a patient with SCC prior to treatment with the candidate drug with one or more antibody(ies) to a MFP under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified MFP. Standard values obtained from a patient before treatment may be compared with values obtained from a patient after treatment. Deviation between standard and subject values establishes the efficacy of the drug.

2.7 Screening Assays

In some embodiments, the MF proteins, antibodies, nucleic acids, and cells containing the MF proteins are used in screening assays. For example, screens for agents that modulate the SCC phenotype can be run. This can be done by screening for modulators of gene expression or for modulators of protein activity at the individual gene or protein level or by evaluating the effect of drug candidates on a "gene expression profile". In some embodiments, the expression profiles are used in conjunction with high throughput screening techniques to allow monitoring for expression profile genes after treatment with a candidate agent (see Zlokamik, et al., 1998, *Science,* 279: 84-8).

"Modulation" includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. If a gene exhibits a 4 fold increase in tumor compared to normal tissue, a decrease of about four fold is desired; a 10 fold decrease in tumor compared to normal tissue gives a 10 fold increase in expression for a candidate agent is desired, etc.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the MFPd and standard immunoassays. Alternatively, binding and bioactivity assays with the protein may be done as outlined below.

In some embodiments, gene expression monitoring is done and a number of genes, i.e. an expression profile, are monitored simultaneously. If desired, multiple protein expression monitoring can be done as well. In embodiments monitoring multiple genes or proteins, the corresponding MF probes are immobilized to solid supports. It is understood that immobilization can occur by any means, including for example; by covalent attachment, by electrostatic immobilization, by attachment through a ligand/ligand interaction, by contact or by depositing on the surface. "Solid support" or "solid substrate" refers to any solid phase material upon which a MF sequence, MFP, or antibody is synthesized, attached, ligated or otherwise immobilized. A solid support may be composed of organic polymers such as polystyrene, polyethylene, polypropylene, polyfluoroethylene, polyethyleneoxy, and polyacrylamide, as well as copolymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

Generally, a candidate bioactive agent is added prior to analysis. The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the SCC phenotype, binding to and/or modulating the bioactivity of an MFP, or the expression of a MF sequence. In a particularly preferred embodiment, the candidate agent suppresses a SCC phenotype, for example to a normal tissue fingerprint. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of an MFP. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, proteins, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In assays for altering the expression profile of one or more MF sequences, after the candidate agent has been added and the cells allowed to incubate for some period of time, the sample containing the MF sequences to be analyzed is added to a solid support. If required, the MF sequence is prepared using known techniques. For example, the sample may be treated to lyse the cells, using known lysis buffers, electroporation, etc., with purification and/or amplification such as PCR occurring as needed, as will be appreciated by those in the art.

Generally, one of the assay components is labeled to provide a means of detecting the binding complex of interest. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the MF nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., 1962, *Nature,* 144: 945; David et al., 1974, *Biochemistry,* 13: 1014; Pain et al., 1981, *J. Immunol. Meth.,* 40: 219; and Nygren, 1982, *J. Histochem. and Cytochem.,* 30: 407. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, or individual proteins, forming an expression profile.

In some embodiments, screening is done to alter the biological function of the expression product of an MF gene. Again, having identified the importance of a gene in a particular state, screening for agents that bind and/or modulate the biological activity of the gene product can be run as is more fully outlined below.

In some embodiments, screens are designed to first find candidate agents that can bind to MF proteins, and then these agents may be used in assays that evaluate the ability of the candidate agent to modulate the MFP activity and the SCC phenotype. As will be appreciated by those in the art, there are a number of different assays which may be run; binding assays and activity assays.

In some embodiments, binding assays are done. In general, purified or isolated MFPs are used. The methods comprise combining a MFP and a candidate bioactive agent, and determining the binding of the candidate agent to the MFP. Generally, the MFP or the candidate agent is non-diffusably bound to a solid support having isolated sample receiving areas (e.g. a microtiter plate, an array, etc.). Microtiter plates and arrays are especially convenient because a large number of assays can be carried out simultaneously, using small amounts of reagents and samples. The particular manner of binding of the composition is not crucial so long as it is compatible with the reagents, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In some embodiments, the MFP is bound to the support, and a candidate bioactive agent is added to the assay. Alternatively, the candidate agent is bound to the support and the MFP is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the MFP may be done in a number of ways. In a preferred embodiment, the candidate bioactive agent is labeled, and binding determined directly. For example, this may be done by attaching all or a portion of the MFP to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In some embodiments, the binding of the candidate bioactive agent is determined through the use of competitive binding assays. In this embodiment, the competitor is a binding moiety known to bind to the MFP, such as an antibody, peptide, binding partner, ligand, etc. Under certain circumstances, there may be competitive binding as between the bioactive agent and the binding moiety, with the binding moiety displacing the bioactive agent.

In some embodiments, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate bioactive agent. Displacement of the competitor is an indication that the candidate bioactive agent is binding to the MFP and thus is capable of binding to, and potentially modulating, the activity of the MFP. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In other embodiments, the candidate bioactive agent is added first, with incubation and washing, followed by the competitor. The absence of binding by the competitor may indicate that the bioactive agent is bound to the MFP with a higher affinity. Thus, if the candidate bioactive agent is labeled, the presence of the label on the support, coupled with a lack of competitor binding, may indicate that the candidate agent is capable of binding to the MFP.

In some embodiments, the methods comprise differential screening to identity bioactive agents that are capable of modulating the activity of the MFPs. In this embodiment, the methods comprise combining a MFP and a competitor in a first sample. A second sample comprises a candidate bioactive agent, a MFP and a competitor. The binding of the competitor is determined for both samples, and a change, or difference in binding between the two samples indicates the presence of an agent capable of binding to the MFP and potentially modulating its activity. That is, if the binding of the competitor is different in the second sample relative to the first sample, the agent is capable of binding to the MFP.

In some embodiments, methods for screening for bioactive agents capable of modulating the activity of a MFP in a cell are provided. The methods comprise adding a candidate bioactive agent, as defined above, to a cell comprising MFPs. Typically, laminin-5 negative primary human keratinocytes are used. The cells can also contain recombinant nucleic acids that encode MF sequences, Ras and a stable NF-κB repressor mutant of IκBα (i.e. IKB) (see Dajee et al., 2003, *Nature*, 421: 630-643). Methods for culturing cells and for assaying cell scattering, adhesion and migration are described in Russell et al., 2003, J. Cell Sci., 116: 3543-3556, the entire contents of which are incorporated herein by reference.

In some embodiments, candidate agents can be introduced into immunodeficient mice that can subsequently be challenged with a MFPs and monitored for the development of tumors. For example, intraperitoneal injections of antibodies against one or more MFPS can be given to mice bearing human foreskin xenografts (see Examples; and Li et al., 2003, EMBO J., 22: 2400-2410). The mice can then be challenged with Ras/IKB transformed human keratinocytes and monitored for tumor growth and histology as described in Dajee et al., 2003, *Nature*, 421: 630-643.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

2.8 Pharmaceutical Compositions

Bioactive agents having pharmacological activity are identified as described above. By "pharmacological activity" herein is meant that the compounds are able to enhance or interfere with the activity of MFPs. The compounds having the desired pharmacological activity may be administered in a physiologically acceptable carrier to a patient. A "patient" includes both humans and other animals, particularly mammals, and domestic animals. Thus, the methods are applicable to both human therapy and veterinary applications.

In some embodiments, bioactive agents include antibodies that recognize MFPs and that have been demonstrated to inhibit or modulate SCC as described herein. In other embodiments, bioactive agents include antisense compositions. These agents can be delivered directly or in pharmaceutical compositions along with suitable carriers or excipients, as well known in the art. Present methods of treatment include embodiments providing for administration of an effective amount of a compound or agent that inhibits the activity or expression of a MFP to a patient in need of treatment.

An effective amount of such agents can readily be determined by routine experimentation, as can the most effective and convenient route of administration and the most appropriate formulation. Various formulations and drug delivery systems are available in the art. (See, e.g., Remington's Pharmaceutical Sciences, supra.)

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the agents can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges for use in an inhaler or insufflator may be formulated. These typically contain a powder mix of the agent and a suitable powder base such as lactose or starch.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

As mentioned above, the compositions can also be formulated as a depot preparation. Such long acting formulations may be administered by implantation (for example, subcutaneously or intramuscularly) or by intramuscular injection. Thus, for example, the present agents may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic agents and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the agents may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the agents for a few weeks up to over 100 days. Depending on the chemical nature and the biological stability of the therapeutic reagent, additional strategies for protein stabilization may be employed.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of MFP activity is desired, the concentration of the test agent that achieves a half-maximal inhibition of MFP activity can be determined. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels or tissue levels of the active moiety which are sufficient to affect the expression or activity of MFPs, as desired, i.e. minimal effective concentration (MEC). The MEC will vary for each agent but can be estimated from, for example, in vitro data, such as the concentration necessary to achieve 50-90% inhibition of MFP activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as squamous cell carcinoma or other cancers and conditions associated with altered expression of MFPs.

3. EXAMPLES

Example 1

Requirement for G4 and/or G5 Domains in SCC Tumors

Laminin-5 undergoes processing of both its γ2 and α3 chains. As the α3 chain contains the primary integrin binding site(s), we performed further studies to examine the functional effects of α3 chain processing on SCC tumor development. We created truncations at the following sites: 1) amino acid residue 1337 (1337Tr), and 2) at amino acid residue 1450 (1450Tr). Keratinocytes from a junctional epidermolysis bullosa (JEB) patient with absent laminin α3 chain expression were transduced with LZRS retroviral vectors containing full length, 1450Tr or 1337Tr cDNA (Matsui et al., 1998, J. Exp. Med., 187: 1273-83). Each of the cDNAs restored trimeric laminin-5 expression in treated JEB keratinocytes, and each cDNA produced comparable levels of secreted laminin-5, as assessed by Western blot using laminin α3 specific antibody. While JEB keratinocytes with no laminin-5 expression (LacZ) were rounded, WT, 1337Tr and 1450Tr expressing keratinocytes showed flattening and spreading. While laminin-5 negative JEB keratinocytes (LacZ) were hypoproliferative, 1337Tr, and 1450Tr showed normal levels of proliferation, comparable to that of wild type (FIG. 5).

Because laminin-5 processing is closely tied to migration, we studied the 1337Tr mutant in more detail, as truncation at this position simulated the effects of processing in vivo. We found that 1337Tr cells were capable of migration, in fact, 1337Tr cells migrated more efficiently in scratch assays compared to cells expressing wild type α3 chain (FIG. 6).

We have previously described a model of human SCC which is obtained from SQ injection of Ras/IKB over expressing human keratinocytes in nude mice (Dajee et al., 2003, Nature, 421: 639-43). Tumors formed in these mice histologically and biochemically, were extremely similar to human SCC tumors. We showed that while laminin-5 negative keratinocytes showed no tendency to form tumors after Ras/IKB transformation, retroviral transfer of laminin-5 cDNA restored both expression of laminin-5 and restored the capacity of these cells to form tumors. These results are significant in that they demonstrate that laminin-5 expression is absolutely required for SCC development.

As an extension of these tumor studies, we next studied the capacity of truncated laminin a3 chain to support SCC development. We Ras/IKB transformed JEB keratinocytes expressing a3 wild type (WT), 1337Tr or LacZ and injected SQ into nude mice. Through two sets of experiments with eight mice per condition, we found that the 1337Tr a3 chain expressing cells did not form any tumors and were most similar to LacZ negative controls (FIG. 7). In addition, 1450Tr cells, though one set of experiments and four mice total per condition, fail to produce SCC tumors either. Despite a lack of tumor formation,1337Tr and 1450Tr cells at injection sites clearly showed expression and extracellular deposition of mutant laminin-5 molecules. These results are significant in that they demonstrate that the G4-5 domain of laminin-5 is essential for SCC development.

Example 2

Cloning of G4 and/or G5 MF Sequences

The laminin α3 chain is processed at residues 1337-1338, according to N-terminal sequencing studies (Tsubota et al., 2000, *Biochem. Biophys. Res. Commun.*, 278: 614-620). As shown in preliminary results, we have produced a human laminin α3 cDNA (1337Tr) which codes for a protein truncated at amino acid 1337, simulating the cleavage product, and have also produced 1450Tr, an α 3 cDNA truncated at amino acid 1450. We propose to produce another laminin α3 cDNA (1551Tr), truncated near the beginning of the G5 domain at amino acid 1551. PCR primers will be designed to produce a product that spans from nucleotide 2771 to nucleotide 4653 of the full length wild type laminin α3 cDNA. This will include a unique BstII site on the laminin α3 cDNA, which will be on the 5' end of the PCR product, and a NotI site will be engineered into the 3' side of the PCR product. The full length laminin α3 cDNA in pENTR1A© (Invitrogen) Gateway plasmid will be cleaved with BstII and NotI enzymes and the PCR product described above will be ligated into the vector with the 3' end ligating with the BstII site in the laminin a3 cDNA, and the 3' end ligating with the pENTR1A multiple cloning site. This cloning product, which will be confirmed by sequencing, will comprise cDNA coding for the laminin α3 chain amino acids 1-1551. The laminin α3 1551Tr cDNA will then be transferred from the pENTR1A plasmid to a Gateway adapted LSRZ retroviral vector through lambda phage recombination reactions.

Three cDNA constructs coding for laminin α3 G domain will be produced. One termed G4 will code for amino acids 1338 to 1560, one termed G5 will code for amino acids 1560 to 1713, and a third termed G4-5 will code for amino acids 1338 to 1713. We will produce each by PCR of the wild type laminin α3 cDNA. In one PCR experiment, we will engineer an EcoR1 tail at either end of each of the three PCR products for cloning into the bacterial expression vector pGEX (Amersham). These constructs will be confirmed by sequencing, and then utilized to produce purified G4, G5 and G4-5 domains in a bacterial expression system.

In another PCR experiment, we will insert an NheI tail on the 5' side and a Not I tail on the 3' side of each of the G4. G5 and G4/5 PCR products. These will be cloned into the mammalian expression vector pCEP which contains a BM40 signal sequence to which cDNA can be cloned to via an NheI restriction site. We have previously used the BM40 signal sequence in this vector to successfully promote secretion of collagen XVII ectodomain (Areida et al., 2001, J. Biol. Chem., 276: 1594-601). The G4, G5 and G4-5 will each be cloned into pCEP vector, to pick up the BM40 signal sequence, then the BM40 signal sequence and laminin α3 G domain cDNA will be removed from the vector by KpnI and NotI restriction sites and ligated into the pENTR1A Gateway vector, and by lambda phage recombination, the laminin α3 G domain cDNAs with their BM40 signal sequences will be cloned into a Gateway adapted LZRS retroviral plasmid.

Example 3

Assays for Detecting Inhibition of SCC Tumorigenesis

At present, it is unclear whether G4-5 domain performs its function in SCC before or after it becomes processed and dissociated from laminin-5. We propose to test this question by attempting to restore tumor generating capabilities in Ras/IKB transformed 1337Tr keratinocytes by adding exogenous G4-5 protein or G4-5 cDNA. If Ras/IKB transformed 1337Tr keratinocytes can form tumors in nude mice after receiving G4-5 protein or cDNA, this would indicate that the G4-5 domain is active in SCC tumors in a soluble form.

Matrigel, which contains heparin sulfate proteoglycan as one of its primary constituents, is the material in which we suspend our Ras/IKB tumors cells in, during subcutaneous injection into nude mice. As the laminin a3 G4-5 domain has heparin binding properties (Amano et al., 2000, J. Biol. Chem., 275: 22728-35), we will suspend the G4-5 domain at 100 μg/250 μl into Matrigel and use it as a substrate for injection of Ras/IKB transformed 1337Tr keratinocytes. We will use laminin α3 G4-5 domain (as described in Aim 1) suspended in Matrigel as a control. We hypothesize that laminin G4-5 domain will remain localized to the Matrigel impregnated matrix surrounding tumor cells and will be slowly released as matrix is gradually remodeled by tumor cells. We will test this on four mice injected with Ras/IKB treated 1337 cells embedded in G4-5 domain containing Matrigel, using four serial biopsies at 1 week intervals by IDIF using G4-5 domain specific antibodies to assess the persistence of G4-5 domain protein in injection/tumor sites.

If laminin α3 G4-5 domain protein is detected and shown to persist in injection sites, we will perform a second set of experiments injecting Ras/IKB transformed cells embedded in Matrigel containing either laminin α3 or laminin α3 G4-5 domain. These cells will be injected into nude mice and assessed over the course of 4 weeks for tumor development. Wild type Ras/IKB transformed keratinocytes will be used as a positive control and 6 mice per condition will be used.

Alternatively, the laminin G4 domain cDNA can be delivered by gene therapy as described below. This technique should promote long term G4-5 domain expression in 1337 Tr cells over the course of the 4 week assay.

Laminin G4-5 domain cDNA will be cloned into LZRS retroviral vector. LacZ or laminin G4-5 cDNA containing retrovirus will be used to infect 1337Tr keratinocytes. Cells will be selected with Blasticidin, transformed with Ras/IKB and then injected into nude mice. Six mice per condition will be assessed over 4 weeks for tumor growth as previously described (Dajee et al, 2003, Nature, 421: 639). Tumors will be analyzed by IDIF using G4/5 or LacZ antibodies to verify secretion of retroviral cDNA products.

The effects of laminin α3 G4 and laminin α3 G5 antibodies on tumor development. We will inject sufficient antibody to maintain a circulating titer of 1:1000 as tested by dilution of mouse sera by Western blot analysis of G4-5 domain protein. Laminin α3 G4, G5 and G4-5 domains cloned into pGEX vector as outlined above will be utilized to produce G4, G5 and G4-5 domain bacterial fusion proteins. Proteins will be affinity purified on a GST column, and GST tags will be subsequently removed by enterokinase (Invitrogen). Isolated G4 and G5 domain proteins will then be used to produce rabbit polyclonal antisera at Josman Labs, Napa, Calif., according to their recommended protocols.

Once high titer polyclonal antisera is obtained, additional G4, G5 and G4-5 protein will be produced, affinity purified and coupled to a Sepharose CL-4B column at a concentration of 0.5 mg protein per ml of gel. G4 polyclonal antisera will be affinity purified on a G4-sepharose column and G5 antisera will be affinity purified on a G5 sepharose column. Affinity purified G4, G5 and G4-5 antibodies will be dialyzed into PBS and filter sterilized. Initially, we will test the antibodies (G4, G5, G4-5) by IP injection of immunodeficient mice bearing human foreskin xenografts by a technique which we have utilized previously (Li et al., 2003, EMBO J., 22:2400-2410). Titers of circulating antibodies in treated mice will be assessed at 3 day intervals using sera obtained from tail vein bleeds. The amount of antibody injec vein bleeds. The amount of antibody injected and the injection intervals will be adjusted to maintain a titer sufficient to detect laminin G4-5 protein by Western blot at a 1:1000 serum dilution. We will clinically assess foreskin grafts and mouse skin over the course of three weeks of injections to determine whether epidermal separation is noted, and mice will be examined by autopsy to detect any epithelial sloughing of mucosa or internal organs.

Once the proper antibody dose and injection intervals are obtained, and if mice are able to tolerate antibody injections, we will go on to perform antibody inhibiton of Ras/IKB wild type keratinocyte derived tumors. In these studies, nude mice will be administered periodic G4, G5 or G4-5 antibody injections to maintain a constant circulating antibody titer as described above. Once antibody titers are initiated, then mice will receive SC injections of Ras/IKB transformed human keratinocytes. Three groups of 6 mice each will be studied, using affinity purified laminin a3 G4 antibody, laminin a3 G5 antibody or mouse IgG. G domain antibody conditions will be analyzed for tumor growth and tumor histology as previously described (Dajee et al., 2003, Nature, 421:639-43).

While the foregoing has presented specific embodiments, it is to be understood that these embodiments have been presented by way of example only. It is expected that others will perceive and practice variations which, though differing from the foregoing, do not depart form the spirit and scope of the inventions as described and claimed herein. All patent applications, patents, and literature references cited in this specification are hereby incorporated by reference in their entirety. In case of conflict or inconsistency, the present description, including definitions, will control.

What is claimed is:

1. A composition comprising a monoclonal antibody against an epitope in the human laminin 5 alpha 3 G4-5 domain, which antibody specifically binds an epitope in the human laminin 5 alpha 3 G4-5 domain lying between amino acid 1399 and amino acid 1713 of SEQ ID NO:2, and a pharmaceutically acceptable carrier.

2. A composition comprising a monoclonal antibody against an epitope in the human laminin 5 alpha 3 G4-5 domain, wherein said antibody binds to an epitope in the laminin 5 alpha 3 G4 domain lying between amino acid 1375 and amino acid 1390 of SEQ ID NO:2 and a pharmaceutically acceptable carrier.

3. A composition according to claim 1, wherein said antibody does not bind to an epitope for a BMP-1 cleavage site within said laminin 5 alpha 3 G4-5 domain.

4. A composition comprising a monoclonal antibody against an epitope in the human laminin 5 alpha 3 G4-5 domain, wherein said antibody binds to an epitope in laminin 5 alpha 3 G4 domain lying between amino acid 1358 and amino acid 1366 of SEQ ID NO:2 and a pharmaceutically acceptable carrier.

* * * * *

SEQUENCE LISTING

<160> NUMBER OF SEQ ID NOS: 24

<210> SEQ ID NO 1
<211> LENGTH: 5433
<212> TYPE: DNA
<213> ORGANISM: Homo sapiens

<400> SEQUENCE: 1

| | | | | | | |
|---|---|---|---|---|---|---|
| atgggatggc | tgtggatctt | tggggcagcc | ctggggcagt | gtctgggcta | cagttcacag | 60 |
| cagcaaaggg | tgccatttct | tcagcctccc | ggtcaaagtc | aactgcaagc | gagttatgtg | 120 |
| gagtttagac | ccagccaggg | ttgtagccct | ggatactatc | gggatcataa | aggcttgtat | 180 |
| accggacggt | gtgttccctg | caattgcaac | ggacattcaa | atcaatgcca | ggatggctca | 240 |
| ggcatatgtg | ttaactgtca | gcacaacacc | gcgggagagc | actgtgaacg | ctgccaggag | 300 |
| ggctactatg | gcaacgccgt | ccacggatcc | tgcagggcct | gcccatgtcc | tcacactaac | 360 |
| agctttgcca | ctggctgtgt | ggtgaatggg | ggagacgtgc | ggtgctcctg | caaagctggg | 420 |
| tacacaggaa | cacagtgtga | aggtgtgca | ccgggatatt | tcgggaatcc | ccagaaattc | 480 |
| ggaggtagct | gccaaccatg | cagttgtaac | agcaatggcc | agctgggcag | ctgtcatccc | 540 |
| ctgactggga | actgcataaa | ccaagaaccc | aaagatagca | gccctgcaga | gaatgtgat | 600 |
| gattgcgaca | gctgtgtgat | gaccctcctg | aacgacctgg | ccaccatggg | cgagcagctc | 660 |
| cgcctggtca | gtctcagct | gcagggcct | agtgccagcg | cagggcttct | ggagcagatg | 720 |
| aggcacatgg | agacccaggc | caaggacctg | aggaatcagt | tgctcaacta | ccgttctgcc | 780 |
| atttcaaatc | atggatcaaa | aatagaaggc | ctggaaagag | aactgactga | tttgaatcaa | 840 |
| gaatttgaga | ctttgcaaga | aaaggctcaa | gtaaattcca | gaaaagcaca | aacattaaac | 900 |
| aacaatgtta | tcgggcaac | acaaagcgca | aagaactgg | atgtgaagat | taaaaatgtc | 960 |
| atccggaatg | tgcacattct | tttaaagcag | atctctggga | cagatggaga | gggaaacaac | 1020 |
| gtgccttcag | gtgacttttc | cagagagtgg | gctgaagccc | agcgcatgat | gagggaactg | 1080 |
| cggaacagga | actttggaaa | gcacctcaga | gaagcagaag | ctgataaaag | ggagtcgcag | 1140 |
| ctcttgctga | accggataag | gacctggcag | aaaacccacc | aggggagaa | caatgggctt | 1200 |
| gctaacagta | tccgggattc | tttaaatgaa | tacgaagcca | aactcagtga | ccttcgtgct | 1260 |
| cggctgcagg | aggcagctgc | ccaagccaag | caggcaaatg | gcttgaacca | agaaaacgag | 1320 |
| agagctttgg | gagccattca | gagacaagtg | aaagaaataa | attccctgca | gagtgatttc | 1380 |
| accaagtatc | taaccactgc | agactcatct | ttgttgcaaa | ccaacattgc | gctgcagctg | 1440 |
| atggagaaaa | gccagaagga | atatgaaaaa | ttagctgcca | gtttaaatga | agcaagacaa | 1500 |
| gaactaagtg | acaaagtaag | agaactttcc | agatctgctg | gcaaaacatc | ccttgtggag | 1560 |
| gaggcagaaa | agcacgcgcg | gtccttacaa | gagctggcaa | agcagctgga | agagatcaag | 1620 |
| agaaacgcca | gcgggatga | gctggtgcgc | tgtgctgtgg | atgccgccac | cgcctacgag | 1680 |
| aacatcctca | tgccatcaa | agcggccgag | gacgcagcca | acgggctgc | cagtgcatct | 1740 |
| gaatctgccc | tccagacagt | gataaaggaa | gatctgccaa | gaaagctaa | accctgagt | 1800 |
| tccaacagtg | ataaactgtt | aaatgaagcc | aagatgacac | aaaagaagct | aaagcaagaa | 1860 |
| gtcagtccag | ctctcaacaa | cctacagcaa | accctgaata | ttgtgacagt | tcagaaagaa | 1920 |
| gtgatagaca | ccaatctcac | aactctccga | gatggtcttc | atgggataca | gagaggtgat | 1980 |
| attgatgcta | tgatcagtag | tgcaaagagc | atggtcagaa | aggccaacga | catcacagat | 2040 |

-continued

```
gaggttctgg atgggctcaa ccccatccag acagatgtgg aaagaattaa ggacacctat    2100
gggaggacac agaacgaaga cttcaaaaag gctctgactg atgcagataa ctcggtgaat    2160
aagttaacca acaaactacc tgatcttttgg cgcaagattg aaagtatcaa ccaacagctg    2220
ttgcccttgg gaaacatctc tgacaacatg gacagaatac gagaactaat tcagcaggcc    2280
agagatgctg ccagtaaggt tgctgtcccc atgaggttca atggtaaatc tggagtcgaa    2340
gtccgactgc caaatgacct ggaagatttg aaaggatata catctctgtc cttgtttctc    2400
caaaggccca actcaagaga aaatgggggt actgagaata tgtttgtgat gtaccttgga    2460
aataaagatg cctcccggga ctacatcggc atggcagttg tggatggcca gctcacctgt    2520
gtctacaacc tgggggaccg tgaggctgaa ctccaagtgg accagatctt gaccaagagt    2580
gagactaagg aggcagttat ggatcgggtg aaatttcaga gaatttatca gtttgcaagg    2640
cttaattaca ccaaaggagc cacatccagt aaaccagaaa cacccggagt ctatgacatg    2700
gatggtagaa atagcaatac actccttaat ttggatcctg aaaatgttgt atttatgtt    2760 ggaggttacc cacctgattt taaacttccc agtcgactaa gtttccctcc atacaaaggt    2820
tgtattgaat tagatgacct caatgaaaat gttctgagct tgtacaactt caaaaaaaca    2880
ttcaatctca acacaactga agtggagcct tgtagaagga ggaaggaaga gtcagacaaa    2940
aattattttg aaggtacggg ctatgctcga gttccaactc aaccacatgc tcccatccca    3000
acctttggac agacaattca gaccaccgtg gatagaggct tgctgttctt tgcagaaaac    3060
ggggatcgct tcatatctct aaatatagaa gatggcaagc tcatggtgag atacaaactg    3120
aattcagagc taccaaaaga gagggagtt ggagacgcca taaacaacgg cagagaccat    3180
tcgattcaga tcaaaattgg aaaactccaa aagcgtatgt ggataaatgt ggacgttcaa    3240
aacactataa ttgatggtga agtatttgat ttcagcacat attatctggg aggaattcca    3300
attgcaatca gggaaagatt taacatttct acgcctgctt tccgaggctg catgaaaaat    3360
ttgaagaaaa ccagtggtgt cgttagattg aatgatactg tgggagtaac caaaaagtgc    3420
tcggaagact ggaagcttgt gcgatctgcc tcattctcca gaggaggaca attgagtttc    3480
actgatttgg gcttaccacc tactgaccac ctccaggcct catttggatt tcagaccttt    3540
caacccagtg gcatattatt agatcatcag acatggacaa ggaacctgca ggtcactctg    3600
gaagatggtt acattgaatt gagcaccagc gatagcggcg gcccaatttt taaatctcca    3660
cagacgtata tggatggttt actgcattat gtatctgtaa taagcgacaa ctctggacta    3720
cggcttctca tcgatgacca gcttctgaga aatagcaaaa ggctaaaaca catttcaagt    3780
tcccggcagt ctctgcgtct gggcgggagc aattttgagg gttgtattag caatgttttt    3840
gtccagaggt tatcactgag tcctgaagtc ctagatttga ccagtaactc tctcaagaga    3900
gatgtgtccc tgggaggctg cagtttaaac aaaccacctt ttctaatgtt gcttaaaggt    3960
tctaccaggt ttaacaagac caagacttt cgtatcaacc agctgttgca ggacacacca    4020
gtggcctccc caaggagcgt gaaggtgtgg caagatgctt gctcaccact tcccaagacc    4080
caggccaatc atggagccct ccagtttggg acattccca ccagccactt gctattcaag    4140
cttcctcagg agctgctgaa acccaggtca cagtttgctg tggacatgca gacaacatcc    4200
tccagaggac tggtgtttca cacgggcact aagaactcct ttatggctct ttatctttca    4260
aaaggacgtc tggtctttgc actggggaca gatgggaaaa aattgaggat caaaagcaag    4320
gagaaatgca atgatgggaa atggcacacg gtggtgtttg ccatgatgg ggaaaagggg    4380
```

-continued

```
cgcttggttg tggatggact gagggcccgg gagggaagtt tgcctggaaa ctccaccatc    4440
agcatcagag cgccagttta cctgggatca cctccatcag ggaaaccaaa gagcctcccc    4500
acaaacagct tgtgggatg cctgaagaac tttcagctgg attcaaaacc cttgtatacc     4560
ccttcttcaa gcttcggggt gtcttcctgc ttgggtggtc ctttggagaa aggcatttat    4620
ttctctgaag aaggaggtca tgtcgtcttg gctcactctg tattgttggg gccagaattt    4680
aagcttgttt tcagcatccg cccaagaagt ctcactggga tcctaataca catcggaagt    4740
cagcccggga agcacttatg tgtttacctg gaggcaggaa aggtcacggc ctctatggac    4800
agtggggcag gtgggacctc aacgtcggtc acaccaaagc agtctctgtg tgatggacag    4860
tggcactcgg tggcagtcac cataaaacaa cacatcctgc acctggaact ggacacagac    4920
agtagctaca cagctggaca gatcccttc ccacctgcca gcactcaaga gccactacac     4980
cttggaggtg ctccagccaa tttgacgaca ctgaggatcc ctgtgtggaa atcattcttt    5040
ggctgtctga ggaatattca tgtcaatcac atccctgtcc ctgtcactga agccttggaa    5100
gtccaggggc ctgtcagtct gaatggttgt cctgaccagt aacccaagcc tatttcacag    5160
caaggaaatt caccttcaaa agcactgatt acccaatgca cctccctccc cagctcgaga    5220
tcattcttca attaggacac aaaccagaca ggtttaatag cgaatctaat tttgaattct    5280
gaccatggat acccatcact ttggcattca gtgctacatg tgtatttat ataaaaatcc     5340
catttcttga agataaaaaa attgttattc aaattgttat gcacagaatg ttttggtaa     5400
tattaatttc cactaaaaaa ttaaatgtct ttt                                 5433
```

<210> SEQ ID NO 2
<211> LENGTH: 1713
<212> TYPE: PRT
<213> ORGANISM: Homo sapiens

<400> SEQUENCE: 2

```
Met Gly Trp Leu Trp Ile Phe Gly Ala Ala Leu Gly Gln Cys Leu Gly
1               5                   10                  15

Tyr Ser Ser Gln Gln Gln Arg Val Pro Phe Leu Gln Pro Gly Gln
            20                  25                  30

Ser Gln Leu Gln Ala Ser Tyr Val Glu Phe Arg Pro Ser Gln Gly Cys
        35                  40                  45

Ser Pro Gly Tyr Tyr Arg Asp His Lys Gly Leu Tyr Thr Gly Arg Cys
    50                  55                  60

Val Pro Cys Asn Cys Asn Gly His Ser Asn Gln Cys Gln Asp Gly Ser
65                  70                  75                  80

Gly Ile Cys Val Asn Cys Gln His Asn Thr Ala Gly Glu His Cys Glu
                85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190
```

```
Ser Ser Pro Ala Glu Glu Cys Asp Asp Cys Asp Ser Cys Val Met Thr
        195                 200                 205
Leu Leu Asn Asp Leu Ala Thr Met Gly Glu Gln Leu Arg Leu Val Lys
        210                 215                 220
Ser Gln Leu Gln Gly Leu Ser Ala Ser Ala Gly Leu Leu Glu Gln Met
225                 230                 235                 240
Arg His Met Glu Thr Gln Ala Lys Asp Leu Arg Asn Gln Leu Leu Asn
                245                 250                 255
Tyr Arg Ser Ala Ile Ser Asn His Gly Ser Lys Ile Glu Gly Leu Glu
                260                 265                 270
Arg Glu Leu Thr Asp Leu Asn Gln Glu Phe Glu Thr Leu Gln Glu Lys
            275                 280                 285
Ala Gln Val Asn Ser Arg Lys Ala Gln Thr Leu Asn Asn Asn Val Asn
        290                 295                 300
Arg Ala Thr Gln Ser Ala Lys Glu Leu Asp Val Lys Ile Lys Asn Val
305                 310                 315                 320
Ile Arg Asn Val His Ile Leu Leu Lys Gln Ile Ser Gly Thr Asp Gly
                325                 330                 335
Glu Gly Asn Asn Val Pro Ser Gly Asp Phe Ser Arg Glu Trp Ala Glu
                340                 345                 350
Ala Gln Arg Met Met Arg Glu Leu Arg Asn Arg Asn Phe Gly Lys His
            355                 360                 365
Leu Arg Glu Ala Glu Ala Asp Lys Arg Glu Ser Gln Leu Leu Leu Asn
        370                 375                 380
Arg Ile Arg Thr Trp Gln Lys Thr His Gln Gly Glu Asn Asn Gly Leu
385                 390                 395                 400
Ala Asn Ser Ile Arg Asp Ser Leu Asn Glu Tyr Glu Ala Lys Leu Ser
                405                 410                 415
Asp Leu Arg Ala Arg Leu Gln Glu Ala Ala Gln Ala Lys Gln Ala
            420                 425                 430
Asn Gly Leu Asn Gln Glu Asn Glu Arg Ala Leu Gly Ala Ile Gln Arg
        435                 440                 445
Gln Val Lys Glu Ile Asn Ser Leu Gln Ser Asp Phe Thr Lys Tyr Leu
    450                 455                 460
Thr Thr Ala Asp Ser Ser Leu Leu Gln Thr Asn Ile Ala Leu Gln Leu
465                 470                 475                 480
Met Glu Lys Ser Gln Lys Glu Tyr Glu Lys Leu Ala Ala Ser Leu Asn
                485                 490                 495
Glu Ala Arg Gln Glu Leu Ser Asp Lys Val Arg Glu Leu Ser Arg Ser
            500                 505                 510
Ala Gly Lys Thr Ser Leu Val Glu Glu Ala Glu Lys His Ala Arg Ser
        515                 520                 525
Leu Gln Glu Leu Ala Lys Gln Leu Glu Glu Ile Lys Arg Asn Ala Ser
        530                 535                 540
Gly Asp Glu Leu Val Arg Cys Ala Val Asp Ala Ala Thr Ala Tyr Glu
545                 550                 555                 560
Asn Ile Leu Asn Ala Ile Lys Ala Ala Glu Asp Ala Ala Asn Arg Ala
                565                 570                 575
Ala Ser Ala Ser Glu Ser Ala Leu Gln Thr Val Ile Lys Glu Asp Leu
            580                 585                 590
Pro Arg Lys Ala Lys Thr Leu Ser Ser Asn Ser Asp Lys Leu Leu Asn
        595                 600                 605
```

```
Glu Ala Lys Met Thr Gln Lys Lys Leu Lys Gln Glu Val Ser Pro Ala
    610                 615                 620

Leu Asn Asn Leu Gln Gln Thr Leu Asn Ile Val Thr Val Gln Lys Glu
625                 630                 635                 640

Val Ile Asp Thr Asn Leu Thr Thr Leu Arg Asp Gly Leu His Gly Ile
                645                 650                 655

Gln Arg Gly Asp Ile Asp Ala Met Ile Ser Ser Ala Lys Ser Met Val
            660                 665                 670

Arg Lys Ala Asn Asp Ile Thr Asp Glu Val Leu Asp Gly Leu Asn Pro
        675                 680                 685

Ile Gln Thr Asp Val Glu Arg Ile Lys Asp Thr Tyr Gly Arg Thr Gln
    690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
                725                 730                 735

Asn Gln Gln Leu Leu Pro Leu Gly Asn Ile Ser Asp Asn Met Asp Arg
            740                 745                 750

Ile Arg Glu Leu Ile Gln Gln Ala Arg Asp Ala Ala Ser Lys Val Ala
        755                 760                 765

Val Pro Met Arg Phe Asn Gly Lys Ser Gly Val Glu Val Arg Leu Pro
    770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
                805                 810                 815

Met Tyr Leu Gly Asn Lys Asp Ala Ser Arg Asp Tyr Ile Gly Met Ala
            820                 825                 830

Val Val Asp Gly Gln Leu Thr Cys Val Tyr Asn Leu Gly Asp Arg Glu
        835                 840                 845

Ala Glu Leu Gln Val Asp Gln Ile Leu Thr Lys Ser Glu Thr Lys Glu
    850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
                885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
        915                 920                 925

Leu Pro Ser Arg Leu Ser Phe Pro Pro Tyr Lys Gly Cys Ile Glu Leu
    930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro  Thr Phe Gly Gln Thr  Ile Gln Thr
        995                 1000                1005

Thr Val  Asp Arg Gly Leu Leu  Phe Phe Ala Glu Asn  Gly Asp Arg
    1010                1015                1020

Phe Ile  Ser Leu Asn Ile Glu  Asp Gly Lys Leu Met  Val Arg Tyr
```

-continued

|     |     |     |     |     |     |     |     |     |     |     |     |
|-----|-----|-----|-----|-----|-----|-----|-----|-----|-----|-----|-----|
|     | 1025 |    |     |     | 1030 |    |     |     | 1035 |    |     |
| Lys | Leu | Asn | Ser | Glu | Leu | Pro | Lys | Glu | Arg | Gly | Val | Gly | Asp | Ala |
|     | 1040 |    |     |     | 1045 |    |     |     | 1050 |    |     |
| Ile | Asn | Asn | Gly | Arg | Asp | His | Ser | Ile | Gln | Ile | Lys | Ile | Gly | Lys |
|     | 1055 |    |     |     | 1060 |    |     |     | 1065 |    |     |

Lys Leu Asn Ser Glu Leu Pro Lys Glu Arg Gly Val Gly Asp Ala
    1040                1045                1050

Ile Asn Asn Gly Arg Asp His Ser Ile Gln Ile Lys Ile Gly Lys
    1055                1060                1065

Leu Gln Lys Arg Met Trp Ile Asn Val Asp Val Gln Asn Thr Ile
    1070                1075                1080

Ile Asp Gly Glu Val Phe Asp Phe Ser Thr Tyr Tyr Leu Gly Gly
    1085                1090                1095

Ile Pro Ile Ala Ile Arg Glu Arg Phe Asn Ile Ser Thr Pro Ala
    1100                1105                1110

Phe Arg Gly Cys Met Lys Asn Leu Lys Lys Thr Ser Gly Val Val
    1115                1120                1125

Arg Leu Asn Asp Thr Val Gly Val Thr Lys Lys Cys Ser Glu Asp
    1130                1135                1140

Trp Lys Leu Val Arg Ser Ala Ser Phe Ser Arg Gly Gly Gln Leu
    1145                1150                1155

Ser Phe Thr Asp Leu Gly Leu Pro Pro Thr Asp His Leu Gln Ala
    1160                1165                1170

Ser Phe Gly Phe Gln Thr Phe Gln Pro Ser Gly Ile Leu Leu Asp
    1175                1180                1185

His Gln Thr Trp Thr Arg Asn Leu Gln Val Thr Leu Glu Asp Gly
    1190                1195                1200

Tyr Ile Glu Leu Ser Thr Ser Asp Ser Gly Gly Pro Ile Phe Lys
    1205                1210                1215

Ser Pro Gln Thr Tyr Met Asp Gly Leu Leu His Tyr Val Ser Val
    1220                1225                1230

Ile Ser Asp Asn Ser Gly Leu Arg Leu Leu Ile Asp Asp Gln Leu
    1235                1240                1245

Leu Arg Asn Ser Lys Arg Leu Lys His Ile Ser Ser Ser Arg Gln
    1250                1255                1260

Ser Leu Arg Leu Gly Gly Ser Asn Phe Glu Gly Cys Ile Ser Asn
    1265                1270                1275

Val Phe Val Gln Arg Leu Ser Leu Ser Pro Glu Val Leu Asp Leu
    1280                1285                1290

Thr Ser Asn Ser Leu Lys Arg Asp Val Ser Leu Gly Gly Cys Ser
    1295                1300                1305

Leu Asn Lys Pro Pro Phe Leu Met Leu Leu Lys Gly Ser Thr Arg
    1310                1315                1320

Phe Asn Lys Thr Lys Thr Phe Arg Ile Asn Gln Leu Leu Gln Asp
    1325                1330                1335

Thr Pro Val Ala Ser Pro Arg Ser Val Lys Val Trp Gln Asp Ala
    1340                1345                1350

Cys Ser Pro Leu Pro Lys Thr Gln Ala Asn His Gly Ala Leu Gln
    1355                1360                1365

Phe Gly Asp Ile Pro Thr Ser His Leu Leu Phe Lys Leu Pro Gln
    1370                1375                1380

Glu Leu Leu Lys Pro Arg Ser Gln Phe Ala Val Asp Met Gln Thr
    1385                1390                1395

Thr Ser Ser Arg Gly Leu Val Phe His Thr Gly Thr Lys Asn Ser
    1400                1405                1410

Phe Met Ala Leu Tyr Leu Ser Lys Gly Arg Leu Val Phe Ala Leu
    1415                1420                1425

Gly Thr Asp Gly Lys Lys Leu Arg Ile Lys Ser Lys Glu Lys Cys
            1430                1435                1440

Asn Asp Gly Lys Trp His Thr Val Val Phe Gly His Asp Gly Glu
        1445                1450                1455

Lys Gly Arg Leu Val Val Asp Gly Leu Arg Ala Arg Glu Gly Ser
    1460                1465                1470

Leu Pro Gly Asn Ser Thr Ile Ser Ile Arg Ala Pro Val Tyr Leu
1475                1480                1485

Gly Ser Pro Pro Ser Gly Lys Pro Lys Ser Leu Pro Thr Asn Ser
    1490                1495                1500

Phe Val Gly Cys Leu Lys Asn Phe Gln Leu Asp Ser Lys Pro Leu
1505                1510                1515

Tyr Thr Pro Ser Ser Ser Phe Gly Val Ser Ser Cys Leu Gly Gly
    1520                1525                1530

Pro Leu Glu Lys Gly Ile Tyr Phe Ser Glu Gly Gly His Val
    1535                1540                1545

Val Leu Ala His Ser Val Leu Leu Gly Pro Glu Phe Lys Leu Val
    1550                1555                1560

Phe Ser Ile Arg Pro Arg Ser Leu Thr Gly Ile Leu Ile His Ile
1565                1570                1575

Gly Ser Gln Pro Gly Lys His Leu Cys Val Tyr Leu Glu Ala Gly
    1580                1585                1590

Lys Val Thr Ala Ser Met Asp Ser Gly Ala Gly Gly Thr Ser Thr
    1595                1600                1605

Ser Val Thr Pro Lys Gln Ser Leu Cys Asp Gly Gln Trp His Ser
    1610                1615                1620

Val Ala Val Thr Ile Lys Gln His Ile Leu His Leu Glu Leu Asp
    1625                1630                1635

Thr Asp Ser Ser Tyr Thr Ala Gly Gln Ile Pro Phe Pro Pro Ala
    1640                1645                1650

Ser Thr Gln Glu Pro Leu His Leu Gly Gly Ala Pro Ala Asn Leu
    1655                1660                1665

Thr Thr Leu Arg Ile Pro Val Trp Lys Ser Phe Phe Gly Cys Leu
    1670                1675                1680

Arg Asn Ile His Val Asn His Ile Pro Val Pro Val Thr Glu Ala
    1685                1690                1695

Leu Glu Val Gln Gly Pro Val Ser Leu Asn Gly Cys Pro Asp Gln
    1700                1705                1710

<210> SEQ ID NO 3
<211> LENGTH: 10511
<212> TYPE: DNA
<213> ORGANISM: Homo sapiens

<400> SEQUENCE: 3
gcaggtccgg gaggcgcagg cggagagcgg cggtgccccc gagcccctct gcggacggct        60
caggcgggag gaccccgcgc ggctggatgg cggcggccgc cgcggcctcgg ggtcgggcac      120 tgggccagt actgccgccg acgccgctgc tcctgctggt actgcgggtg ctgccagcct        180
gcggggcgac cgctcgggat cccggggccg cggccgggct cagccttcac ccgacttact      240
tcaacctggc cgaggcggcg aggatttggg ccaccgccac ctgcggggag aggggacccg      300
gcgaggggag gccccagccc gagctctact gcaagttggt cggggggccc accgccccag      360
gcagcggcca caccatccag ggccagttct gtgactattg caattctgaa gaccccagga      420

-continued

```
aagcacatcc tgtcaccaat gccatcgatg gatctgaacg ttggtggcaa agccctcccc      480
tgtcctcagg cacacagtac aacagagtca acctcacctt ggatctgggg cagctcttcc      540
atgtggccta tattttaatc aaatttgcaa attctcctcg ccctgatctt tgggtcttgg      600
aaagatctgt agactttgga agcacctact caccatggca atattttgct cattctaaag      660
tagactgttt aaaagaattt gggcgggagg caaatatggc tgtcacccgg gatgatgatg      720
tactttgtgt tactgaatat tcccgtattg taccctttgga aaatggtgag gttgtggtgt      780
ccttgataaa cggtcgtcca ggtgcaaaaa attttacttt ctctcacacc ctgagggagt      840
ttaccaaggc aacaaacatc cgcttgcgtt ttcttagaac caatacgctt cttggacacc      900
tcatctccaa agcccagcga gatccaactg tcactcggcg gtattattac agcataaagg      960
acatcagcat tggtgggcag tgtgtttgca atggccatgc tgaagtgtgc aatataaaca     1020
atcctgaaaa actgtttcgg tgtgaatgcc agcaccacac ctgtggggag acgtgtgatc     1080
gctgctgcac agggtacaat cagaggcgct ggcggcccgc cgcttgggag cagagccacg     1140
agtgtgaagc atgcaactgc cacggccatg ccagcaactg ttactatgat ccagatgttg     1200
agcggcagca ggcaagcttg aatacccagg gcatctatgc tggtggaggg gtctgcatta     1260
actgtcagca caacacagct ggagtaaact gtgaacagtg tgctaagggc tattaccgcc     1320 cttatgggt tccagtggat gcccctgatg gctgcatccc ctgcagctgt gaccctgagc     1380
atgcggatgg ctgtgaacag ggttcaggcc gctgtcactg caagccaaat ttccacggag     1440
acaactgtga gaagtgtgca attggatact acaatttccc attttgcttg gaattccca     1500 tttttcctgt ttctacacca agttcagaag atccagtagc tggagatata aaagggtgtg     1560
actgtaatct ggaaggtgtt ctccctgaaa tatgtgatgc ccacgacgg tgcctgtgcc     1620 gccctgggt tgagggccct cgatgtgata cctgccgctc tggtttctac tcattcccta     1680
tttgccaagc ctgctggtgt tcagcccttg gatcctacca gatgccctgc agctcagtga     1740
ctggacagtg tgaatgtcgg ccaggagtta caggacagcg gtgtgacagg tgtctctcag     1800
gagcttatga tttcccccac tgccaaggtt ccagcagtgc ttgtgaccca gctggtacca     1860
tcaactccaa tttggggtat tgccaatgca agcttcatgt tgaaggtcct acttgtagcc     1920
gctgcaaact gttatattgg aatctggaca agaaaaccc cagtggatgt tcagaatgca     1980
agtgccataa ggcgggaaca gtgagtggaa ctggagagtg taggcaggga gatggtgact     2040
gtcactgcaa gtcccatgtg ggtggcgatt cctgcgacac ctgtgaagat ggatattttg     2100 cttttggaaaa gagcaattac tttgggtgtc aagggtgtca gtgtgacatt ggtgggcat     2160 tgtcctccat gtgcagtggg ccctcgggag tgtgccagtg ccgagagcat gtcgtgggaa     2220
aggtgtgcca gcggcctgaa aacaactact atttcccaga tttgcatcat atgaagtatg     2280
agattgaaga cggcagcaca cctaatggga gagaccttcg atttggatttt gatccgctgg     2340 catttcctga gtttagctgg agaggatatg cccaaatgac ctcagtacag aatgatgtaa     2400
gaataacatt gaatgtaggg aagtcaagtg gctccttgtt tcgtgttatt ctgagatacg     2460
ttaaccctgg aactgaagca gtatctggcc atataactat ttatccatcc tggggtgctg     2520
ctcaaagcaa agagatcatc ttcctgccga gtaaggagcc agcctttgtc actgtccctg     2580
gaaatggttt tgcagaccca ttttcaatca caccaggaat atgggttgct tgtattaagg     2640
cagaaggagt ccttctggat tacctggtgc tgctccccag ggactactat gaagcctctg     2700
tactgcagct gccagtcaca gaaccatgtg cctacgcagg acctcccaa gaaaattgct     2760
```

```
tactctacca gcatttgcca gtgaccagat tccctgtac cctggcttgt gaggccagac    2820
acttcctgct tgatggggag ccaagacccg tggcagtgag gcagcccaca cctgcacacc    2880
ctgtcatggt ggacctcagc gggagagagg tggaattgca tctgcggctg cgcatcccac    2940
aggttggcca ctacgtggtt gtggtcgagt attccacgga ggcagctcag ctgtttgtgg    3000
ttgatgtgaa tgtgaagagc tccgggtctg ttctggcagg ccaggtgaac atttacagct    3060
gcaactacag tgttctctgc cggagtgctg tgattgatca catgagccgc atcgccatgt    3120
atgagctatt ggcagatgca gacattcagc tcaagggaca catggcccga ttccttctgc    3180
atcaagtttg tatcatacct attgaagaat tctcagctga gtatgtgaga ccacaagtcc    3240
actgcattgc cagttatggg cgatttgtca atcaaagtgc cacctgtgtc tccttggccc    3300
atgaaactcc tccaacagca ttaattttgg atgttctaag tggcaggcct ttccctcacc    3360
tgccccagca gtcgtcacct tctgttgatg ttcttcctgg ggtcaccttg aaggcaccgc    3420
agaatcaagt gaccctgaga ggacgtgtac cacacctggg ccgatacgtc tttgtcatcc    3480
atttttacca agcagcgcac ccgacgtttc ccgcgcaggt gtcggtggat ggcgggtggc    3540
cacgggcagg ctccttccat gcctcttttt gccccatgt gcttggctgc cgggatcaag    3600
tgattgccga aggccagatt gagtttgaca tctcagagcc tgaagtggcc gcaactgtga    3660
aggttccaga aggaaagtcc ttggttttgg tccgtgttct agtggtgcct gcagaaaact    3720
atgactacca aatacttcac aaaaaatcca tggacaagtc actcgagttt atcaccaatt    3780
gtggaaaaaa cagcttttac cttgacccc agacagcctc cagattctgt aagaattccg    3840
ccaggtccct ggtggccttt taccacaagg gcgccctgcc ttgtgagtgc caccccactg    3900
gggccaccgg ccctcactgc agccctgagg gtgggcagtg cccatgccag cccaacgtca    3960
tcggcggca gtgcacccgc tgtgcaacag gccactacgg attcccacgc tgcaagccgt    4020
gcagctgtgg tcggcgcctt tgtgaagaga tgacggggca gtgccgctgc cctcccgca    4080
cggtcaggcc ccagtgtgag gtgtgtgaga cacactcatt cagcttccac cccatggccg    4140
gctgcgaagg ctgcaactgt tccaggaggg gcaccatcga ggctgccatg ccggagtgtg    4200
accgggacag cgggcagtgc agatgcaagc ccagaatcac agggcggcag tgtgaccgat    4260
gtgcttccgg gttttaccgc tttcctgagt gtgttccctg caattgcaac agagatggga    4320
ctgagccagg agtgtgtgac ccagggaccg gggcttgcct ctgcaaggaa aatgtagaag    4380
gcacagagtg taatgtgtgt cgagaaggct cattccattt ggaccagcc aatctcaagg    4440
gttgtaccag ctgtttctgt tttggagtaa ataatcaatg tcacagctca cataagcgaa    4500
ggactaagtt tgtggatatg ctgggctggc acctggagac agcagacaga gtggacatcc    4560
ctgtctcttt caacccaggc agcaacagta tggtggcgga tctccaggag ctgcccgcaa    4620
ccatccacag cgcgtcctgg gtcgcaccca cctcctacct gggggacaag gtttcttcat    4680
atggtggtta cctcacttac caagccaagt cctttggctt gctggcgac atggttcttc    4740
tggaaaagaa gccggatgta cagctcactg gtcagcacat gtccatcatc tatgaggaga    4800
caaacacccc acggccagac cggctgcatc atggacgagt gcacgtggtc gagggaaact    4860
tcagacatgc cagcagccgt gccccagtgt ctagggagga gctgatgaca gtgctgtcta    4920
gactggcaga tgtgcgcatc caaggcctct acttcacaga gactcaaagg ctcacctga    4980
gcgaggtggg gctagaggaa gcctctgaca caggaagtgg gcgcatagca cttgctgtgg    5040
aaatctgtgc ctgcccccct gcctacgctg gtgactcttg tcaggttgt agccctggat    5100
actatcggga tcataaaggc ttgtataccg gacggtgtgt tccctgcaat tgcaacggac    5160
```

-continued

```
attcaaatca atgccaggat ggctcaggca tatgtgttaa ctgtcagcac aacaccgcgg    5220
gagagcactg tgaacgctgc caggagggct actatggcaa cgccgtccac ggatcctgca    5280
gggcctgccc atgtcctcac actaacagct ttgccactgg ctgtgtggtg aatgggggag    5340
acgtgcggtg ctcctgcaaa gctgggtaca caggaacaca gtgtgaaagg tgtgcaccgg    5400
gatatttcgg gaatcccag aaattcggag gtagctgcca accatgcagt tgtaacagca    5460
atggccagct gggcagctgt catccctga ctggagactg cataaaccaa gaacccaaag    5520
atagcagccc tgcagaagaa tgtgatgatt gcgacagctg tgtgatgacc ctcctgaacg    5580
acctggccac catgggcgag cagctccgcc tggtcaagtc tcagctgcag ggcctgagtg    5640
ccagcgcagg gcttctggag cagatgaggc acatggagac ccaggccaag gacctgagga    5700
atcagttgct caactaccgt tctgccattt caaatcatgg atcaaaaata gaaggcctgg    5760
aaagagaact gactgatttg aatcaagaat ttgagacttt gcaagaaaag gctcaagtaa    5820
attccagaaa agcacaaaca ttaaacaaca atgttaatcg ggcaacacaa agcgcaaaag    5880
aactggatgt gaagattaaa aatgtcatcc ggaatgtgca cattctttta aagcagatct    5940
ctgggacaga tggagaggga acaacgtgc cttcaggtga cttttccaga gagtgggctg    6000
aagcccagcg catgatgagg gaactgcgga acaggaactt tggaaagcac ctcagagaag    6060
cagaagctga taaaagggag tcgcagctct tgctgaaccg gataaggacc tggcagaaaa    6120
cccaccaggg ggagaacaat gggcttgcta acagtatccg ggattcttta aatgaatacg    6180
aagccaaact cagtgacctt cgtgctcggc tgcaggaggc agctgcccaa gccaagcagg    6240
caaatggctt gaaccaagaa acgagagag ctttgggagc cattcagaga caagtgaaag    6300
aaataaattc cctgcagagt gatttcacca agtatctaac cactgcagac tcatctttgt    6360
tgcaaaccaa cattgcgctg cagctgatgg agaaaagcca gaggaatat gaaaaattag    6420 ctgccagttt aaatgaagca agacaagaac taagtgacaa agtaagagaa ctttccagat    6480
ctgctggcaa acatcccctt gtggaggagg cagaaaagca cgcgcggtcc ttacaagagc    6540
tggcaaagca gctggaagag atcaagagaa acgccagcgg ggatgagctg gtgcgctgtg    6600
ctgtggatgc cgccaccgcc tacgagaaca tcctcaatgc catcaaagcg gccgaggacg    6660
cagccaacag ggctgccagt gcatctgaat ctgccctcca gacagtgata aggaagatc    6720 tgccaagaaa agctaaaacc ctgagttcca acagtgataa actgttaaat gaagccaaga    6780
tgacacaaaa gaagctaaag caagaagtca gtccagctct caacaaccta cagcaaaccc    6840
tgaatattgt gacagttcag aaagaagtga tagacaccaa tctcacaact ctccgagatg    6900
gtcttcatgg gatacagaga ggtgatattg atgctatgat cagtagtgca aagagcatgg    6960
tcagaaaggc caacgacatc acagatgagg ttctggatgg gctcaacccc atccagacag    7020
atgtggaaag aattaaggac acctatggga ggacacagaa cgaagacttc aaaaaggctc    7080
tgactgatgc agataactcg gtgaataagt taaccaacaa actacctgat ctttggcgca    7140
agattgaaag tatcaaccaa cagctgttgc ccttgggaaa catctctgac aacatggaca    7200
gaatacgaga actaattcag caggccagag atgctgccag taaggttgct gtccccatga    7260
ggttcaatgg taaatctgga gtcgaagtcc gactgccaaa tgacctggaa gatttgaaag    7320
gatatacatc tctgtccttg tttctccaaa ggcccaactc aagagaaaat gggggtactg    7380
agaatatgtt tgtgatgtac cttggaaata aagatgcctc ccgggactac atcggcatgg    7440
cagttgtgga tggccagctc acctgtgtct acaacctggg ggaccgtgag gctgaactcc    7500
```

-continued

```
aagtggacca gatcttgacc aagagtgaga ctaaggaggc agttatggat cgggtgaaat    7560
ttcagagaat ttatcagttt gcaaggctta attacaccaa aggagccaca tccagtaaac    7620
cagaaacacc cggagtctat gacatggatg gtagaaatag caatacactc cttaatttgg    7680
atcctgaaaa tgttgtattt tatgttggag gttacccacc tgattttaaa cttcccagtc    7740
gactaagttt ccctccatac aaaggttgta ttgaattaga tgacctcaat gaaaatgttc    7800
tgagcttgta caacttcaaa aaaacattca atctcaacac aactgaagtg gagccttgta    7860
gaaggaggaa ggaagagtca gacaaaaatt attttgaagg tacgggctat gctcgagttc    7920
caactcaacc acatgctccc atcccaacct ttggacagca aattcagacc accgtggata    7980
gaggcttgct gttctttgca gaaaacgggg atcgcttcat atctctaaat atagaagatg    8040
gcaagctcat ggtgagatac aaactgaatt cagagctacc aaaagagaga ggagttggag    8100
acgccataaa caacggcaga gaccattcga ttcagatcaa aattggaaaa ctccaaaagc    8160
gtatgtggat aaatgtggac gttcaaaaca ctataattga tggtgaagta tttgatttca    8220
gcacatatta tctgggagga attccaattg caatcaggga agatttaac atttctacgc    8280 ctgctttccg aggctgcatg aaaaatttga agaaaaccag tggtgtcgtt agattgaatg    8340
atactgtggg agtaaccaaa aagtgctcgg aagactggaa gcttgtgcga tctgcctcat    8400
tctccagagg aggacaattg agtttcactg atttgggctt accacctact gaccacctcc    8460
aggcctcatt tggatttcag acctttcaac ccagtggcat attattagat catcagacat    8520
ggacaaggaa cctgcaggtc actctggaag atggttacat tgaattgagc accagcgata    8580
gcggcagccc aattttttaaa tctccacaga cgtatatgga tggtttactg cattatgtat    8640
ctgtaataag cgacaactct ggactacggc ttctcatcga tgaccagctt ctgagaaata    8700
gcaaaaggct aaaacacatt tcaagttccc ggcagtctct gcgtctgggc gggagcaatt    8760
ttgagggttg tattagcaat gttttttgtcc agaggttatc actgagtcct gaagtcctag    8820
atttgaccag taactctctc aagagagatg tgtccctggg aggctgcagt ttaaacaaac    8880
caccttttct aatgttgctt aaaggttcta ccaggtttaa caagaccaag acttttcgta    8940
tcaaccagct gttgcaggac acaccagtgg cctccccaag gagcgtgaag gtgtggcaag    9000
atgcttgctc accacttccc aagacccagg ccaatcatgg agccctccag tttgggggaca    9060 ttcccaccag ccacttgcta ttcaagcttc ctcaggagct gctgaaaccc aggtcacagt    9120
ttgctgtgga catgcagaca acatcctcca gaggactggt gtttcacacg ggcactaaga    9180
actcctttat ggctctttat ctttcaaaag gacgtctggt ctttgcactg gggacagatg    9240
ggaaaaaatt gaggatcaaa agcaaggaga aatgcaatga tgggaaatgg cacacggtgg    9300
tgtttggcca tgatggggaa aagggggcgct tggttgtgga tggactgagg gcccgggagg    9360
gaagtttgcc tggaaactcc accatcagca tcagagcgcc agtttacctg ggatcacctc    9420
catcagggaa accaaagagc ctccccacaa acagctttgt gggatgcctg aagaactttc    9480
agctggattc aaaaccctt g tatacccctt cttcaagctt cggggtgtct tcctgcttgg    9540
gtggtccttt ggagaaaggc atttatttct ctgaagaagg aggtcatgtc gtcttggctc    9600
actctgtatt gttggggcca gaatttaagc ttgttttcag catccgccca agaagtctca    9660
ctgggatcct aatacacatc ggaagtcagc ccgggaagca cttatgtgtt tacctggagg    9720
caggaaaggt cacggcctct atggacagtg gggcaggtgg gacctcaacg tcggtcacac    9780
caaagcagtc tctgtgtgat ggacagtggc actcggtggc agtcaccata aaacaacaca    9840
tcctgcacct ggaactggac acagacagta gctacacagc tggacagatc cccttcccac    9900
```

-continued

```
ctgccagcac tcaagagcca ctacaccttg gaggtgctcc agccaatttg acgacactga    9960
ggatccctgt gtggaaatca ttctttggct gtctgaggaa tattcatgtc aatcacatcc   10020
ctgtccctgt cactgaagcc ttggaagtcc aggggcctgt cagtctgaat ggttgtcctg   10080
accagtaacc caagcctatt tcacagcaag gaaattcacc ttcaaaagca ctgattaccc   10140
aatgcacctc cctccccagc tcgagatcat tcttcactca ggacacaaac cagacaggtt   10200
taatagcgaa tctaattttg aattctgacc atggataccc atcactttgg cattcagtgc   10260
tacatgtgta ttttatataa aaatcccatt tcttgaagat aaaaaaattg ttattcaaat   10320
tgttatgcac agaatgtttt tggtaatatt aatttccact aaaaaattaa atgtctttta   10380
agaaacattc ttttccactt gttaaaaaaa ttaaatatat tttaaagcac tttaagaata   10440
tgaaactttc atatatgtta aaggattata atttatggaa ttaaaaaatg cagtgtagtc   10500
cttaaaaaaa a                                                         10511
```

<210> SEQ ID NO 4
<211> LENGTH: 3333
<212> TYPE: PRT
<213> ORGANISM: Homo sapiens

<400> SEQUENCE: 4

```
Met Ala Ala Ala Arg Pro Arg Gly Arg Ala Leu Gly Pro Val Leu
1               5                   10                  15

Pro Pro Thr Pro Leu Leu Leu Val Leu Arg Val Leu Pro Ala Cys
            20                  25                  30

Gly Ala Thr Ala Arg Asp Pro Gly Ala Ala Gly Leu Ser Leu His
            35                  40                  45

Pro Thr Tyr Phe Asn Leu Ala Glu Ala Ala Arg Ile Trp Ala Thr Ala
    50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
            100                 105                 110

Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
        195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                245                 250                 255
```

```
Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Tyr Tyr Tyr
    275                 280                 285

Ser Ile Lys Asp Ile Ser Ile Gly Gly Gln Cys Val Cys Asn Gly His
        290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
                355                 360                 365

Pro Asp Val Glu Arg Gln Gln Ala Ser Leu Asn Thr Gln Gly Ile Tyr
    370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
                405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
435                 440                 445

Phe His Gly Asp Asn Cys Glu Lys Cys Ala Ile Gly Tyr Tyr Asn Phe
    450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
            485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
    515                 520                 525

Ser Phe Pro Ile Cys Gln Ala Cys Trp Cys Ser Ala Leu Gly Ser Tyr
    530                 535                 540

Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
            565                 570                 575

Pro His Cys Gln Gly Ser Ser Ala Cys Asp Pro Ala Gly Thr Ile
    580                 585                 590

Asn Ser Asn Leu Gly Tyr Cys Gln Cys Lys Leu His Val Glu Gly Pro
    595                 600                 605

Thr Cys Ser Arg Cys Lys Leu Leu Tyr Trp Asn Leu Asp Lys Glu Asn
    610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Cys His Cys Lys Ser
            645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
```

```
                675                 680                 685
Gly Gly Ala Leu Ser Ser Met Cys Ser Gly Pro Ser Gly Val Cys Gln
690                 695                 700
Cys Arg Glu His Val Val Gly Lys Val Cys Gln Arg Pro Glu Asn Asn
705                 710                 715                 720
Tyr Tyr Phe Pro Asp Leu His Met Lys Tyr Glu Ile Glu Asp Gly
                725                 730                 735
Ser Thr Pro Asn Gly Arg Asp Leu Arg Phe Gly Phe Asp Pro Leu Ala
                740                 745                 750
Phe Pro Glu Phe Ser Trp Arg Gly Tyr Ala Gln Met Thr Ser Val Gln
                755                 760                 765
Asn Asp Val Arg Ile Thr Leu Asn Val Gly Lys Ser Ser Gly Ser Leu
                770                 775                 780
Phe Arg Val Ile Leu Arg Tyr Val Asn Pro Gly Thr Glu Ala Val Ser
785                 790                 795                 800
Gly His Ile Thr Ile Tyr Pro Ser Trp Gly Ala Ala Gln Ser Lys Glu
                805                 810                 815
Ile Ile Phe Leu Pro Ser Lys Glu Pro Ala Phe Val Thr Val Pro Gly
                820                 825                 830
Asn Gly Phe Ala Asp Pro Phe Ser Ile Thr Pro Gly Ile Trp Val Ala
                835                 840                 845
Cys Ile Lys Ala Glu Gly Val Leu Leu Asp Tyr Leu Val Leu Leu Pro
                850                 855                 860
Arg Asp Tyr Tyr Glu Ala Ser Val Leu Gln Leu Pro Val Thr Glu Pro
865                 870                 875                 880
Cys Ala Tyr Ala Gly Pro Pro Gln Glu Asn Cys Leu Leu Tyr Gln His
                885                 890                 895
Leu Pro Val Thr Arg Phe Pro Cys Thr Leu Ala Cys Glu Ala Arg His
                900                 905                 910
Phe Leu Leu Asp Gly Glu Pro Arg Pro Val Ala Val Arg Gln Pro Thr
                915                 920                 925
Pro Ala His Pro Val Met Val Asp Leu Ser Gly Arg Glu Val Glu Leu
                930                 935                 940
His Leu Arg Leu Arg Ile Pro Gln Val Gly His Tyr Val Val Val
945                 950                 955                 960
Glu Tyr Ser Thr Glu Ala Ala Gln Leu Phe Val Val Asp Val Asn Val
                965                 970                 975
Lys Ser Ser Gly Ser Val Leu Ala Gly Gln Val Asn Ile Tyr Ser Cys
                980                 985                 990
Asn Tyr Ser Val Leu Cys Arg Ser  Ala Val Ile Asp His  Met Ser Arg
                995                 1000                1005
Ile Ala  Met Tyr Glu Leu Leu  Ala Asp Ala Asp Ile  Gln Leu Lys
    1010                1015                1020
Gly His  Met Ala Arg Phe Leu  Leu His Gln Val Cys  Ile Ile Pro
    1025                1030                1035
Ile Glu  Glu Phe Ser Ala Glu  Tyr Val Arg Pro Gln  Val His Cys
    1040                1045                1050
Ile Ala  Ser Tyr Gly Arg Phe  Val Asn Gln Ser Ala  Thr Cys Val
    1055                1060                1065
Ser Leu  Ala His Glu Thr Pro  Pro Thr Ala Leu Ile  Leu Asp Val
    1070                1075                1080
Leu Ser  Gly Arg Pro Phe Pro  His Leu Pro Gln Gln  Ser Ser Pro
    1085                1090                1095
```

-continued

```
Ser Val Asp Val Leu Pro Gly Val Thr Leu Lys Ala Pro Gln Asn
    1100                1105                1110

Gln Val Thr Leu Arg Gly Arg Val Pro His Leu Gly Arg Tyr Val
    1115                1120                1125

Phe Val Ile His Phe Tyr Gln Ala Ala His Pro Thr Phe Pro Ala
    1130                1135                1140

Gln Val Ser Val Asp Gly Gly Trp Pro Arg Ala Gly Ser Phe His
    1145                1150                1155

Ala Ser Phe Cys Pro His Val Leu Gly Cys Arg Asp Gln Val Ile
    1160                1165                1170

Ala Glu Gly Gln Ile Glu Phe Asp Ile Ser Glu Pro Glu Val Ala
    1175                1180                1185

Ala Thr Val Lys Val Pro Glu Gly Lys Ser Leu Val Leu Val Arg
    1190                1195                1200

Val Leu Val Val Pro Ala Glu Asn Tyr Asp Tyr Gln Ile Leu His
    1205                1210                1215

Lys Lys Ser Met Asp Lys Ser Leu Glu Phe Ile Thr Asn Cys Gly
    1220                1225                1230

Lys Asn Ser Phe Tyr Leu Asp Pro Gln Thr Ala Ser Arg Phe Cys
    1235                1240                1245

Lys Asn Ser Ala Arg Ser Leu Val Ala Phe Tyr His Lys Gly Ala
    1250                1255                1260

Leu Pro Cys Glu Cys His Pro Thr Gly Ala Thr Gly Pro His Cys
    1265                1270                1275

Ser Pro Glu Gly Gly Gln Cys Pro Cys Gln Pro Asn Val Ile Gly
    1280                1285                1290

Arg Gln Cys Thr Arg Cys Ala Thr Gly His Tyr Gly Phe Pro Arg
    1295                1300                1305

Cys Lys Pro Cys Ser Cys Gly Arg Arg Leu Cys Glu Glu Met Thr
    1310                1315                1320

Gly Gln Cys Arg Cys Pro Pro Arg Thr Val Arg Pro Gln Cys Glu
    1325                1330                1335

Val Cys Glu Thr His Ser Phe Ser Phe His Pro Met Ala Gly Cys
    1340                1345                1350

Glu Gly Cys Asn Cys Ser Arg Arg Gly Thr Ile Glu Ala Ala Met
    1355                1360                1365

Pro Glu Cys Asp Arg Asp Ser Gly Gln Cys Arg Cys Lys Pro Arg
    1370                1375                1380

Ile Thr Gly Arg Gln Cys Asp Arg Cys Ala Ser Gly Phe Tyr Arg
    1385                1390                1395

Phe Pro Glu Cys Val Pro Cys Asn Cys Asn Arg Asp Gly Thr Glu
    1400                1405                1410

Pro Gly Val Cys Asp Pro Gly Thr Gly Ala Cys Leu Cys Lys Glu
    1415                1420                1425

Asn Val Glu Gly Thr Glu Cys Asn Val Cys Arg Glu Gly Ser Phe
    1430                1435                1440

His Leu Asp Pro Ala Asn Leu Lys Gly Cys Thr Ser Cys Phe Cys
    1445                1450                1455

Phe Gly Val Asn Asn Gln Cys His Ser Ser His Lys Arg Arg Thr
    1460                1465                1470

Lys Phe Val Asp Met Leu Gly Trp His Leu Glu Thr Ala Asp Arg
    1475                1480                1485
```

-continued

```
Val Asp Ile Pro Val Ser Phe Asn Pro Gly Ser Asn  Ser Met Val
1490             1495                 1500

Ala Asp Leu Gln Glu Leu Pro Ala Thr Ile His Ser  Ala Ser Trp
1505             1510                 1515

Val Ala Pro Thr Ser Tyr Leu Gly Asp Lys Val Ser  Ser Tyr Gly
1520             1525                 1530

Gly Tyr Leu Thr Tyr Gln Ala Lys Ser Phe Gly Leu  Pro Gly Asp
1535             1540                 1545

Met Val Leu Leu Glu Lys Lys Pro Asp Val Gln Leu  Thr Gly Gln
1550             1555                 1560

His Met Ser Ile Ile Tyr Glu Glu Thr Asn Thr Pro  Arg Pro Asp
1565             1570                 1575

Arg Leu His His Gly Arg Val His Val Val Glu Gly  Asn Phe Arg
1580             1585                 1590

His Ala Ser Ser Arg Ala Pro Val Ser Arg Glu Glu  Leu Met Thr
1595             1600                 1605

Val Leu Ser Arg Leu Ala Asp Val Arg Ile Gln Gly  Leu Tyr Phe
1610             1615                 1620

Thr Glu Thr Gln Arg Leu Thr Leu Ser Glu Val Gly  Leu Glu Glu
1625             1630                 1635

Ala Ser Asp Thr Gly Ser Gly Arg Ile Ala Leu Ala  Val Glu Ile
1640             1645                 1650

Cys Ala Cys Pro Pro Ala Tyr Ala Gly Asp Ser Cys  Gln Gly Cys
1655             1660                 1665

Ser Pro Gly Tyr Tyr Arg Asp His Lys Gly Leu Tyr  Thr Gly Arg
1670             1675                 1680

Cys Val Pro Cys Asn Cys Asn Gly His Ser Asn Gln  Cys Gln Asp
1685             1690                 1695

Gly Ser Gly Ile Cys Val Asn Cys Gln His Asn Thr  Ala Gly Glu
1700             1705                 1710

His Cys Glu Arg Cys Gln Glu Gly Tyr Tyr Gly Asn  Ala Val His
1715             1720                 1725

Gly Ser Cys Arg Ala Cys Pro Cys Pro His Thr Asn  Ser Phe Ala
1730             1735                 1740

Thr Gly Cys Val Val Asn Gly Gly Asp Val Arg Cys  Ser Cys Lys
1745             1750                 1755

Ala Gly Tyr Thr Gly Thr Gln Cys Glu Arg Cys Ala  Pro Gly Tyr
1760             1765                 1770

Phe Gly Asn Pro Gln Lys Phe Gly Gly Ser Cys Gln  Pro Cys Ser
1775             1780                 1785

Cys Asn Ser Asn Gly Gln Leu Gly Ser Cys His Pro  Leu Thr Gly
1790             1795                 1800

Asp Cys Ile Asn Gln Glu Pro Lys Asp Ser Ser Pro  Ala Glu Glu
1805             1810                 1815

Cys Asp Asp Cys Asp Ser Cys Val Met Thr Leu Leu  Asn Asp Leu
1820             1825                 1830

Ala Thr Met Gly Glu Gln Leu Arg Leu Val Lys Ser  Gln Leu Gln
1835             1840                 1845

Gly Leu Ser Ala Ser Ala Gly Leu Leu Glu Gln Met  Arg His Met
1850             1855                 1860

Glu Thr Gln Ala Lys Asp Leu Arg Asn Gln Leu Leu  Asn Tyr Arg
1865             1870                 1875

Ser Ala Ile Ser Asn His Gly Ser Lys Ile Glu Gly  Leu Glu Arg
```

```
                    1880          1885          1890
Glu Leu Thr Asp Leu Asn Gln Glu Phe Glu Thr Leu Gln Glu Lys
        1895              1900              1905
Ala Gln Val Asn Ser Arg Lys Ala Gln Thr Leu Asn Asn Asn Val
        1910              1915              1920
Asn Arg Ala Thr Gln Ser Ala Lys Glu Leu Asp Val Lys Ile Lys
        1925              1930              1935
Asn Val Ile Arg Asn Val His Ile Leu Leu Lys Gln Ile Ser Gly
        1940              1945              1950
Thr Asp Gly Glu Gly Asn Asn Val Pro Ser Gly Asp Phe Ser Arg
        1955              1960              1965
Glu Trp Ala Glu Ala Gln Arg Met Met Arg Glu Leu Arg Asn Arg
        1970              1975              1980
Asn Phe Gly Lys His Leu Arg Glu Ala Glu Ala Asp Lys Arg Glu
        1985              1990              1995
Ser Gln Leu Leu Leu Asn Arg Ile Arg Thr Trp Gln Lys Thr His
        2000              2005              2010
Gln Gly Glu Asn Asn Gly Leu Ala Asn Ser Ile Arg Asp Ser Leu
        2015              2020              2025
Asn Glu Tyr Glu Ala Lys Leu Ser Asp Leu Arg Ala Arg Leu Gln
        2030              2035              2040
Glu Ala Ala Ala Gln Ala Lys Gln Ala Asn Gly Leu Asn Gln Glu
        2045              2050              2055
Asn Glu Arg Ala Leu Gly Ala Ile Gln Arg Gln Val Lys Glu Ile
        2060              2065              2070
Asn Ser Leu Gln Ser Asp Phe Thr Lys Tyr Leu Thr Thr Ala Asp
        2075              2080              2085
Ser Ser Leu Leu Gln Thr Asn Ile Ala Leu Gln Leu Met Glu Lys
        2090              2095              2100
Ser Gln Lys Glu Tyr Glu Lys Leu Ala Ala Ser Leu Asn Glu Ala
        2105              2110              2115
Arg Gln Glu Leu Ser Asp Lys Val Arg Glu Leu Ser Arg Ser Ala
        2120              2125              2130
Gly Lys Thr Ser Leu Val Glu Glu Ala Glu Lys His Ala Arg Ser
        2135              2140              2145
Leu Gln Glu Leu Ala Lys Gln Leu Glu Glu Ile Lys Arg Asn Ala
        2150              2155              2160
Ser Gly Asp Glu Leu Val Arg Cys Ala Val Asp Ala Ala Thr Ala
        2165              2170              2175
Tyr Glu Asn Ile Leu Asn Ala Ile Lys Ala Ala Glu Asp Ala Ala
        2180              2185              2190
Asn Arg Ala Ala Ser Ala Ser Glu Ser Ala Leu Gln Thr Val Ile
        2195              2200              2205
Lys Glu Asp Leu Pro Arg Lys Ala Lys Thr Leu Ser Ser Asn Ser
        2210              2215              2220
Asp Lys Leu Leu Asn Glu Ala Lys Met Thr Gln Lys Lys Leu Lys
        2225              2230              2235
Gln Glu Val Ser Pro Ala Leu Asn Asn Leu Gln Gln Thr Leu Asn
        2240              2245              2250
Ile Val Thr Val Gln Lys Glu Val Ile Asp Thr Asn Leu Thr Thr
        2255              2260              2265
Leu Arg Asp Gly Leu His Gly Ile Gln Arg Gly Asp Ile Asp Ala
        2270              2275              2280
```

```
Met Ile Ser Ser Ala Lys Ser Met Val Arg Lys Ala Asn Asp Ile
    2285                2290                2295

Thr Asp Glu Val Leu Asp Gly Leu Asn Pro Ile Gln Thr Asp Val
    2300                2305                2310

Glu Arg Ile Lys Asp Thr Tyr Gly Arg Thr Gln Asn Glu Asp Phe
    2315                2320                2325

Lys Lys Ala Leu Thr Asp Ala Asp Asn Ser Val Asn Lys Leu Thr
    2330                2335                2340

Asn Lys Leu Pro Asp Leu Trp Arg Lys Ile Glu Ser Ile Asn Gln
    2345                2350                2355

Gln Leu Leu Pro Leu Gly Asn Ile Ser Asp Asn Met Asp Arg Ile
    2360                2365                2370

Arg Glu Leu Ile Gln Gln Ala Arg Asp Ala Ala Ser Lys Val Ala
    2375                2380                2385

Val Pro Met Arg Phe Asn Gly Lys Ser Gly Val Glu Val Arg Leu
    2390                2395                2400

Pro Asn Asp Leu Glu Asp Leu Lys Gly Tyr Thr Ser Leu Ser Leu
    2405                2410                2415

Phe Leu Gln Arg Pro Asn Ser Arg Glu Asn Gly Gly Thr Glu Asn
    2420                2425                2430

Met Phe Val Met Tyr Leu Gly Asn Lys Asp Ala Ser Arg Asp Tyr
    2435                2440                2445

Ile Gly Met Ala Val Val Asp Gly Gln Leu Thr Cys Val Tyr Asn
    2450                2455                2460

Leu Gly Asp Arg Glu Ala Glu Leu Gln Val Asp Gln Ile Leu Thr
    2465                2470                2475

Lys Ser Glu Thr Lys Glu Ala Val Met Asp Arg Val Lys Phe Gln
    2480                2485                2490

Arg Ile Tyr Gln Phe Ala Arg Leu Asn Tyr Thr Lys Gly Ala Thr
    2495                2500                2505

Ser Ser Lys Pro Glu Thr Pro Gly Val Tyr Asp Met Asp Gly Arg
    2510                2515                2520

Asn Ser Asn Thr Leu Leu Asn Leu Asp Pro Glu Asn Val Val Phe
    2525                2530                2535

Tyr Val Gly Gly Tyr Pro Pro Asp Phe Lys Leu Pro Ser Arg Leu
    2540                2545                2550

Ser Phe Pro Pro Tyr Lys Gly Cys Ile Glu Leu Asp Asp Leu Asn
    2555                2560                2565

Glu Asn Val Leu Ser Leu Tyr Asn Phe Lys Lys Thr Phe Asn Leu
    2570                2575                2580

Asn Thr Thr Glu Val Glu Pro Cys Arg Arg Arg Lys Glu Glu Ser
    2585                2590                2595

Asp Lys Asn Tyr Phe Glu Gly Thr Gly Tyr Ala Arg Val Pro Thr
    2600                2605                2610

Gln Pro His Ala Pro Ile Pro Thr Phe Gly Gln Thr Ile Gln Thr
    2615                2620                2625

Thr Val Asp Arg Gly Leu Leu Phe Phe Ala Glu Asn Gly Asp Arg
    2630                2635                2640

Phe Ile Ser Leu Asn Ile Glu Asp Gly Lys Leu Met Val Arg Tyr
    2645                2650                2655

Lys Leu Asn Ser Glu Leu Pro Lys Glu Arg Gly Val Gly Asp Ala
    2660                2665                2670
```

```
Ile Asn Asn Gly Arg Asp His Ser Ile Gln Ile Lys Ile Gly Lys
2675                 2680                 2685

Leu Gln Lys Arg Met Trp Ile Asn Val Asp Val Gln Asn Thr Ile
2690                 2695                 2700

Ile Asp Gly Glu Val Phe Asp Phe Ser Thr Tyr Tyr Leu Gly Gly
2705                 2710                 2715

Ile Pro Ile Ala Ile Arg Glu Arg Phe Asn Ile Ser Thr Pro Ala
2720                 2725                 2730

Phe Arg Gly Cys Met Lys Asn Leu Lys Lys Thr Ser Gly Val Val
2735                 2740                 2745

Arg Leu Asn Asp Thr Val Gly Val Thr Lys Lys Cys Ser Glu Asp
2750                 2755                 2760

Trp Lys Leu Val Arg Ser Ala Ser Phe Ser Arg Gly Gly Gln Leu
2765                 2770                 2775

Ser Phe Thr Asp Leu Gly Leu Pro Pro Thr Asp His Leu Gln Ala
2780                 2785                 2790

Ser Phe Gly Phe Gln Thr Phe Gln Pro Ser Gly Ile Leu Leu Asp
2795                 2800                 2805

His Gln Thr Trp Thr Arg Asn Leu Gln Val Thr Leu Glu Asp Gly
2810                 2815                 2820

Tyr Ile Glu Leu Ser Thr Ser Asp Ser Gly Ser Pro Ile Phe Lys
2825                 2830                 2835

Ser Pro Gln Thr Tyr Met Asp Gly Leu Leu His Tyr Val Ser Val
2840                 2845                 2850

Ile Ser Asp Asn Ser Gly Leu Arg Leu Leu Ile Asp Asp Gln Leu
2855                 2860                 2865

Leu Arg Asn Ser Lys Arg Leu Lys His Ile Ser Ser Arg Gln
2870                 2875                 2880

Ser Leu Arg Leu Gly Gly Ser Asn Phe Glu Gly Cys Ile Ser Asn
2885                 2890                 2895

Val Phe Val Gln Arg Leu Ser Leu Ser Pro Glu Val Leu Asp Leu
2900                 2905                 2910

Thr Ser Asn Ser Leu Lys Arg Asp Val Ser Leu Gly Gly Cys Ser
2915                 2920                 2925

Leu Asn Lys Pro Pro Phe Leu Met Leu Leu Lys Gly Ser Thr Arg
2930                 2935                 2940

Phe Asn Lys Thr Lys Thr Phe Arg Ile Asn Gln Leu Leu Gln Asp
2945                 2950                 2955

Thr Pro Val Ala Ser Pro Arg Ser Val Lys Val Trp Gln Asp Ala
2960                 2965                 2970

Cys Ser Pro Leu Pro Lys Thr Gln Ala Asn His Gly Ala Leu Gln
2975                 2980                 2985

Phe Gly Asp Ile Pro Thr Ser His Leu Leu Phe Lys Leu Pro Gln
2990                 2995                 3000

Glu Leu Leu Lys Pro Arg Ser Gln Phe Ala Val Asp Met Gln Thr
3005                 3010                 3015

Thr Ser Ser Arg Gly Leu Val Phe His Thr Gly Thr Lys Asn Ser
3020                 3025                 3030

Phe Met Ala Leu Tyr Leu Ser Lys Gly Arg Leu Val Phe Ala Leu
3035                 3040                 3045

Gly Thr Asp Gly Lys Lys Leu Arg Ile Lys Ser Lys Glu Lys Cys
3050                 3055                 3060

Asn Asp Gly Lys Trp His Thr Val Val Phe Gly His Asp Gly Glu
```

-continued

| | | | | | | | | | |
|---|---|---|---|---|---|---|---|---|---|
| | 3065 | | | 3070 | | | 3075 | | |

Lys Gly Arg Leu Val Val Asp Gly Leu Arg Ala Arg Glu Gly Ser
     3080                3085                3090

Leu Pro Gly Asn Ser Thr Ile Ser Ile Arg Ala Pro Val Tyr Leu
     3095                3100                3105

Gly Ser Pro Pro Ser Gly Lys Pro Lys Ser Leu Pro Thr Asn Ser
     3110                3115                3120

Phe Val Gly Cys Leu Lys Asn Phe Gln Leu Asp Ser Lys Pro Leu
     3125                3130                3135

Tyr Thr Pro Ser Ser Ser Phe Gly Val Ser Ser Cys Leu Gly Gly
     3140                3145                3150

Pro Leu Glu Lys Gly Ile Tyr Phe Ser Glu Gly Gly His Val
     3155                3160                3165

Val Leu Ala His Ser Val Leu Leu Gly Pro Glu Phe Lys Leu Val
     3170                3175                3180

Phe Ser Ile Arg Pro Arg Ser Leu Thr Gly Ile Leu Ile His Ile
     3185                3190                3195

Gly Ser Gln Pro Gly Lys His Leu Cys Val Tyr Leu Glu Ala Gly
     3200                3205                3210

Lys Val Thr Ala Ser Met Asp Ser Gly Ala Gly Gly Thr Ser Thr
     3215                3220                3225

Ser Val Thr Pro Lys Gln Ser Leu Cys Asp Gly Gln Trp His Ser
     3230                3235                3240

Val Ala Val Thr Ile Lys Gln His Ile Leu His Leu Glu Leu Asp
     3245                3250                3255

Thr Asp Ser Ser Tyr Thr Ala Gly Gln Ile Pro Phe Pro Pro Ala
     3260                3265                3270

Ser Thr Gln Glu Pro Leu His Leu Gly Gly Ala Pro Ala Asn Leu
     3275                3280                3285

Thr Thr Leu Arg Ile Pro Val Trp Lys Ser Phe Phe Gly Cys Leu
     3290                3295                3300

Arg Asn Ile His Val Asn His His Ile Pro Val Pro Val Thr Glu Ala
     3305                3310                3315

Leu Glu Val Gln Gly Pro Val Ser Leu Asn Gly Cys Pro Asp Gln
     3320                3325                3330

<210> SEQ ID NO 5
<211> LENGTH: 5601
<212> TYPE: DNA
<213> ORGANISM: Homo sapiens

<400> SEQUENCE: 5
gggatgcctc cagcagtgag gcggtcagcc tgcagcatgg gatggctgtg gatctttggg      60
gcagccctgg ggcagtgtct gggctacagt tcacagcagc aaagggtgcc atttcttcag     120
cctcccggtc aaagtcaact gcaagcgagt tatgtggagt ttagacccag ccagggttgt     180
agccctggat actatcggga tcataaaggc ttgtataccg gacggtgtgt tccctgcaat     240
tgcaacggac attcaaatca atgccaggat ggctcaggca tatgtgttaa ctgtcagcac     300
aacaccgcgg gagagcactg tgaacgctgc caggagggct actatggcaa cgccgtccac     360
ggatcctgca gggcctgccc atgtcctcac actaacagct tgccactggc tgtgtggtg      420 aatgggggag acgtgcggtg ctcctgcaaa gctgggtaca caggaacaca gtgtgaaagg     480
tgtgcaccgg gatatttcgg gaatcccccag aaattcggag gtagcctgcca accatgcagt     540

```
tgtaacagca atggccagct gggcagctgt catcccctga ctggagactg cataaaccaa      600
gaacccaaag atagcagccc tgcagaagaa tgtgatgatt gcgacagctg tgtgatgacc      660
ctcctgaacg acctggccac catgggcgag cagctccgcc tggtcaagtc tcagctgcag      720
ggcctgagtg ccagcgcagg gcttctggag cagatgaggc acatggagac ccaggccaag      780
gacctgagga atcagttgct caactaccgt tctgccattt caaatcatgg atcaaaaata      840
gaaggcctgg aaagagaact gactgatttg aatcaagaat ttgagacttt gcaagaaaag      900
gctcaagtaa attccagaaa agcacaaaca ttaaacaaca atgttaatcg ggcaacacaa      960
agcgcaaaag aactggatgt gaagattaaa aatgtcatcc ggaatgtgca cattctttta     1020
aagcagatct ctgggacaga tggagaggga acaacgtgc cttcaggtga cttttccaga      1080
gagtgggctg aagcccagcg catgatgagg gaactgcgga acaggaactt tggaaagcac     1140
ctcagagaag cagaagctga taaaagggag tcgcagctct gctgaaccg ataaggacc       1200 tggcagaaaa cccaccaggg ggagaacaat gggcttgcta acagtatccg ggattcttta     1260
aatgaatacg aagccaaact cagtgacctt cgtgctcggc tgcaggaggc agctgcccaa     1320
gccaagcagg caaatggctt gaaccaagaa acgagagag ctttgggagc cattcagaga      1380
caagtgaaag aaataaattc cctgcagagt gatttcacca agtatctaac cactgcagac     1440
tcatctttgt tgcaaaccaa cattgcgctg cagctgatgg agaaaagcca gaaggaatat     1500
gaaaaattag ctgccagttt aaatgaagca agacaagaac taagtgacaa agtaagagaa     1560 cttttccagat ctgctggcaa acatcccctt gtggaggagg cagaaaagca cgcgcggtcc    1620
ttacaagagc tggcaaagca gctggaagag atcaagagaa acgccagcgg ggatgagctg     1680
gtgcgctgtg ctgtggatgc cgccaccgcc tacgagaaca tcctcaatgc catcaaagcg     1740
gccgaggacg cagccaacag gctgccagt gcatctgaat ctgccctcca gacagtgata     1800
aaggaagatc tgccaagaaa agctaaaacc ctgagttcca acagtgataa actgttaaat     1860
gaagccaaga tgacacaaaa gaagctaaag caagaagtca gtccagctct caacaaccta     1920
cagcaaaccc tgaatattgt gacagttcag aaagaagtga tagacaccaa tctcacaact     1980
ctccgagatg gtcttcatgg gatacagaga ggtgatattg atgctatgat cagtagtgca     2040
aagagcatgg tcagaaaggc caacgacatc acagatgagg ttctggatgg gctcaaccc      2100 atccagacag atgtggaaag aattaaggac acctatggga ggacacagaa cgaagacttc     2160
aaaaaggctc tgactgatgc agataactcg gtgaataagt taaccaacaa actacctgat     2220 cttttggcgca agattgaaag tatcaaccaa cagctgttgc ccttgggaaa catctctgac     2280
aacatggaca gaatacgaga actaattcag caggccagag atgctgccag taaggttgct     2340
gtccccatga ggttcaatgg taaatctgga gtcgaagtcc gactgccaaa tgacctggaa     2400
gatttgaaag gatatacatc tctgtccttg tttctccaaa ggcccaactc aagagaaaat     2460
gggggtactg agaatatgtt tgtgatgtac cttggaaata agatgcctc ccgggactac      2520 atcggcatgg cagttgtgga tggccagctc acctgtgtct acaacctggg ggaccgtgag     2580
gctgaactcc aagtggacca gatcttgacc aagagtgaga ctaaggaggc agttatggat     2640
cgggtgaaat ttcagagaat ttatcagttt gcaaggctta attacaccaa aggagccaca     2700
tccagtaaac cagaaacacc cggagtctat gacatggatg gtagaaatag caatacactc     2760
cttaatttgg atcctgaaaa tgttgtattt tatgttggag gttacccacc tgatttaaaa     2820
cttcccagtc gactaagttt ccctccatac aaaggttgta ttgaattaga tgacctcaat     2880
gaaaatgttc tgagcttgta caacttcaaa aaaacattca atctcaacac aactgaagtg     2940
```

```
gagccttgta aaggaggaa ggaagagtca gacaaaaatt attttgaagg tacgggctat    3000
gctcgagttc aactcaacc acatgctccc atcccaacct ttggacagac aattcagacc    3060
accgtggata gaggcttgct gttctttgca gaaaacgggg atcgcttcat atctctaaat    3120
atagaagatg gcaagctcat ggtgagatac aaactgaatt cagagctacc aaaagagaga    3180
ggagttggag acgccataaa caacggcaga gaccattcga ttcagatcaa aattggaaaa    3240
ctccaaaagc gtatgtggat aaatgtggac gttcaaaaca ctataattga tggtgaagta    3300
tttgatttca gcacatatta tctgggagga attccaattg caatcaggga agatttaac     3360 atttctacgc ctgctttccg aggctgcatg aaaaatttga agaaaaccag tggtgtcgtt    3420
agattgaatg atactgtggg agtaaccaaa aagtgctcgg aagactggaa gcttgtgcga    3480
tctgcctcat tctccagagg aggacaattg agtttcactg atttgggctt accacctact    3540
gaccacctcc aggcctcatt tggatttcag acctttcaac ccagtggcat attattagat    3600
catcagacat ggacaaggaa cctgcaggtc actctggaag atggttacat tgaattgagc    3660
accagcgata gcggcagccc aatttttaaa tctccacaga cgtatatgga tggtttactg    3720
cattatgtat ctgtaataag cgacaactct ggactacggc ttctcatcga tgaccagctt    3780
ctgagaaata gcaaaaggct aaaacacatt tcaagttccc ggcagtctct gcgtctgggc    3840
gggagcaatt ttgagggttg tattagcaat gttttttgtcc agaggttatc actgagtcct    3900
gaagtcctag atttgaccag taactctctc aagagagatg tgtccctggg aggctgcagt    3960
ttaaacaaac caccttttct aatgttgctt aaaggttcta ccaggtttaa caagaccaag    4020
acttttcgta tcaaccagct gttgcaggac acaccagtgg cctccccaag gagcgtgaag    4080
gtgtggcaag atgcttgctc accacttccc aagacccagg ccaatcatgg agccctccag    4140
tttggggaca ttcccaccag ccacttgcta ttcaagcttc ctcaggagct gctgaaaccc    4200
aggtcacagt ttgctgtgga catgcagaca acatcctcca gaggactggt gtttcacacg    4260
ggcactaaga actcctttat ggctcttat ctttcaaaag gacgtctggt cttttgcactg    4320 gggacagatg ggaaaaaatt gaggatcaaa agcaaggaga aatgcaatga tgggaaatgg    4380
cacacggtgg tgtttggcca tgatggggaa aaggggcgct tggttgtgga tggactgagg    4440
gcccgggagg gaagtttgcc tggaaactcc accatcagca tcagagcgcc agtttacctg    4500
ggatcacctc catcagggaa accaaagagc ctccccacaa acagctttgt gggatgcctg    4560
aagaactttc agctggattc aaaacccttg tatacccctt cttcaagctt cggggtgtct    4620
tcctgcttgg gtggtccttt ggagaaaggc atttatttct ctgaagaagg aggtcatgtc    4680
gtcttggctc actctgtatt gttggggcca gaatttaagc ttgttttcag catccgccca    4740
agaagtctca ctgggatcct aatacacatc ggaagtcagc ccgggaagca cttatgtgtt    4800
tacctggagg caggaaaggt cacggcctct atggacagtg gggcaggtgg gacctcaacg    4860
tcggtcacac caaagcagtc tctgtgtgat ggacagtggc actcggtggc agtcaccata    4920
aaacaacaca tcctgcacct ggaactggac acagacagta gctacacagc tggacagatc    4980
cccttcccac ctgccagcac tcaagagcca ctacaccttg gaggtgctcc agccaatttg    5040
acgacactga ggatccctgt gtggaaatca ttctttggct gtctgaggaa tattcatgtc    5100
aatcacatcc ctgtccctgt cactgaagcc ttggaagtcc aggggcctgt cagtctgaat    5160
ggttgtcctg accagtaacc caagcctatt tcacagcaag gaaattcacc ttcaaaagca    5220
ctgattaccc aatgcacctc cctccccagc tcgagatcat tcttcactca ggacacaaac    5280
```

-continued

```
cagacaggtt taatagcgaa tctaattttg aattctgacc atggataccc atcactttgg    5340
cattcagtgc tacatgtgta ttttatataa aaatcccatt tcttgaagat aaaaaaattg    5400
ttattcaaat tgttatgcac agaatgtttt tggtaatatt aatttccact aaaaaattaa    5460
atgtctttta agaaacattc ttttccactt gttaaaaaaa ttaaatatat tttaaagcac    5520
tttaagaata tgaaactttc atatatgtta aaggattata atttatggaa ttaaaaaatg    5580
cagtgtagtc cttaaaaaaa a                                              5601
```

<210> SEQ ID NO 6
<211> LENGTH: 1724
<212> TYPE: PRT
<213> ORGANISM: Homo sapiens

<400> SEQUENCE: 6

```
Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
            20                  25                  30

Gln Arg Val Pro Phe Leu Gln Pro Gly Gln Ser Gln Leu Gln Ala
        35                  40                  45

Ser Tyr Val Glu Phe Arg Pro Ser Gln Gly Cys Ser Pro Gly Tyr Tyr
    50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
        115                 120                 125

His Thr Asn Ser Phe Ala Thr Gly Cys Val Val Asn Gly Gly Asp Val
    130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
        195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
        275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320
```

```
Ala Lys Glu Leu Asp Val Lys Ile Lys Asn Val Ile Arg Asn Val His
            325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
            355                 360                 365

Arg Glu Leu Arg Asn Arg Asn Phe Gly Lys His Leu Arg Glu Ala Glu
            370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
            405                 410                 415

Asp Ser Leu Asn Glu Tyr Glu Ala Lys Leu Ser Asp Leu Arg Ala Arg
            420                 425                 430

Leu Gln Glu Ala Ala Ala Gln Ala Lys Gln Ala Asn Gly Leu Asn Gln
            435                 440                 445

Glu Asn Glu Arg Ala Leu Gly Ala Ile Gln Arg Gln Val Lys Glu Ile
450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
            485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
            515                 520                 525

Leu Val Glu Glu Ala Glu Lys His Ala Arg Ser Leu Gln Glu Leu Ala
            530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
            565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
            610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
            645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
            675                 680                 685

Ile Thr Asp Glu Val Leu Asp Gly Leu Asn Pro Ile Gln Thr Asp Val
            690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
            725                 730                 735
```

```
Leu Pro Asp Leu Trp Arg Lys Ile Glu Ser Ile Asn Gln Gln Leu Leu
            740                 745                 750

Pro Leu Gly Asn Ile Ser Asp Asn Met Asp Arg Ile Arg Glu Leu Ile
            755                 760                 765

Gln Gln Ala Arg Asp Ala Ala Ser Lys Val Ala Val Pro Met Arg Phe
770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
            805                 810                 815

Arg Glu Asn Gly Gly Thr Glu Asn Met Phe Val Met Tyr Leu Gly Asn
            820                 825                 830

Lys Asp Ala Ser Arg Asp Tyr Ile Gly Met Ala Val Val Asp Gly Gln
            835                 840                 845

Leu Thr Cys Val Tyr Asn Leu Gly Asp Arg Glu Ala Glu Leu Gln Val
            850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
            885                 890                 895

Gly Ala Thr Ser Ser Lys Pro Glu Thr Pro Gly Val Tyr Asp Met Asp
            900                 905                 910

Gly Arg Asn Ser Asn Thr Leu Leu Asn Leu Asp Pro Glu Asn Val Val
            915                 920                 925

Phe Tyr Val Gly Gly Tyr Pro Pro Asp Phe Lys Leu Pro Ser Arg Leu
            930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
            965                 970                 975

Thr Glu Val Glu Pro Cys Arg Arg Lys Glu Glu Ser Asp Lys Asn
            980                 985                 990

Tyr Phe Glu Gly Thr Gly Tyr Ala  Arg Val Pro Thr Gln Pro His Ala
            995                 1000                1005

Pro Ile  Pro Thr Phe Gly Gln  Thr Ile Gln Thr Thr  Val Asp Arg
    1010                1015                1020

Gly Leu  Leu Phe Phe Ala Glu  Asn Gly Asp Arg Phe  Ile Ser Leu
    1025                1030                1035

Asn Ile  Glu Asp Gly Lys Leu  Met Val Arg Tyr Lys  Leu Asn Ser
    1040                1045                1050

Glu Leu  Pro Lys Glu Arg Gly  Val Gly Asp Ala Ile  Asn Asn Gly
    1055                1060                1065

Arg Asp  His Ser Ile Gln Ile  Lys Ile Gly Lys Leu  Gln Lys Arg
    1070                1075                1080

Met Trp  Ile Asn Val Asp Val  Gln Asn Thr Ile Ile  Asp Gly Glu
    1085                1090                1095

Val Phe  Asp Phe Ser Thr Tyr  Tyr Leu Gly Gly Ile  Pro Ile Ala
    1100                1105                1110

Ile Arg  Glu Arg Phe Asn Ile  Ser Thr Pro Ala Phe  Arg Gly Cys
    1115                1120                1125

Met Lys  Asn Leu Lys Lys Thr  Ser Gly Val Val Arg  Leu Asn Asp
    1130                1135                1140

Thr Val  Gly Val Thr Lys Lys  Cys Ser Glu Asp Trp  Lys Leu Val
```

-continued

```
            1145                1150                1155

Arg Ser Ala Ser Phe Ser Arg Gly Gly Gln Leu Ser Phe Thr Asp
    1160                1165                1170

Leu Gly Leu Pro Pro Thr Asp His Leu Gln Ala Ser Phe Gly Phe
    1175                1180                1185

Gln Thr Phe Gln Pro Ser Gly Ile Leu Leu Asp His Gln Thr Trp
    1190                1195                1200

Thr Arg Asn Leu Gln Val Thr Leu Glu Asp Gly Tyr Ile Glu Leu
    1205                1210                1215

Ser Thr Ser Asp Ser Gly Ser Pro Ile Phe Lys Ser Pro Gln Thr
    1220                1225                1230

Tyr Met Asp Gly Leu Leu His Tyr Val Ser Val Ile Ser Asp Asn
    1235                1240                1245

Ser Gly Leu Arg Leu Leu Ile Asp Asp Gln Leu Leu Arg Asn Ser
    1250                1255                1260

Lys Arg Leu Lys His Ile Ser Ser Arg Gln Ser Leu Arg Leu
    1265                1270                1275

Gly Gly Ser Asn Phe Glu Gly Cys Ile Ser Asn Val Phe Val Gln
    1280                1285                1290

Arg Leu Ser Leu Ser Pro Glu Val Leu Asp Leu Thr Ser Asn Ser
    1295                1300                1305

Leu Lys Arg Asp Val Ser Leu Gly Gly Cys Ser Leu Asn Lys Pro
    1310                1315                1320

Pro Phe Leu Met Leu Leu Lys Gly Ser Thr Arg Phe Asn Lys Thr
    1325                1330                1335

Lys Thr Phe Arg Ile Asn Gln Leu Leu Gln Asp Thr Pro Val Ala
    1340                1345                1350

Ser Pro Arg Ser Val Lys Val Trp Gln Asp Ala Cys Ser Pro Leu
    1355                1360                1365

Pro Lys Thr Gln Ala Asn His Gly Ala Leu Gln Phe Gly Asp Ile
    1370                1375                1380

Pro Thr Ser His Leu Leu Phe Lys Leu Pro Gln Glu Leu Leu Lys
    1385                1390                1395

Pro Arg Ser Gln Phe Ala Val Asp Met Gln Thr Thr Ser Ser Arg
    1400                1405                1410

Gly Leu Val Phe His Thr Gly Thr Lys Asn Ser Phe Met Ala Leu
    1415                1420                1425

Tyr Leu Ser Lys Gly Arg Leu Val Phe Ala Leu Gly Thr Asp Gly
    1430                1435                1440

Lys Lys Leu Arg Ile Lys Ser Lys Glu Lys Cys Asn Asp Gly Lys
    1445                1450                1455

Trp His Thr Val Val Phe Gly His Asp Gly Glu Lys Gly Arg Leu
    1460                1465                1470

Val Val Asp Gly Leu Arg Ala Arg Glu Gly Ser Leu Pro Gly Asn
    1475                1480                1485

Ser Thr Ile Ser Ile Arg Ala Pro Val Tyr Leu Gly Ser Pro Pro
    1490                1495                1500

Ser Gly Lys Pro Lys Ser Leu Pro Thr Asn Ser Phe Val Gly Cys
    1505                1510                1515

Leu Lys Asn Phe Gln Leu Asp Ser Lys Pro Leu Tyr Thr Pro Ser
    1520                1525                1530

Ser Ser Phe Gly Val Ser Ser Cys Leu Gly Gly Pro Leu Glu Lys
    1535                1540                1545
```

```
Gly Ile Tyr Phe Ser Glu Glu Gly Gly His Val Val Leu Ala His
    1550                1555                1560
Ser Val Leu Leu Gly Pro Glu Phe Lys Leu Val Phe Ser Ile Arg
    1565                1570                1575
Pro Arg Ser Leu Thr Gly Ile Leu Ile His Ile Gly Ser Gln Pro
    1580                1585                1590
Gly Lys His Leu Cys Val Tyr Leu Glu Ala Gly Lys Val Thr Ala
    1595                1600                1605
Ser Met Asp Ser Gly Ala Gly Gly Thr Ser Thr Ser Val Thr Pro
    1610                1615                1620
Lys Gln Ser Leu Cys Asp Gly Gln Trp His Ser Val Ala Val Thr
    1625                1630                1635
Ile Lys Gln His Ile Leu His Leu Glu Leu Asp Thr Asp Ser Ser
    1640                1645                1650
Tyr Thr Ala Gly Gln Ile Pro Phe Pro Pro Ala Ser Thr Gln Glu
    1655                1660                1665
Pro Leu His Leu Gly Gly Ala Pro Ala Asn Leu Thr Thr Leu Arg
    1670                1675                1680
Ile Pro Val Trp Lys Ser Phe Phe Gly Cys Leu Arg Asn Ile His
    1685                1690                1695
Val Asn His Ile Pro Val Pro Val Thr Glu Ala Leu Glu Val Gln
    1700                1705                1710
Gly Pro Val Ser Leu Asn Gly Cys Pro Asp Gln
    1715                1720
```

<210> SEQ ID NO 7
<211> LENGTH: 5264
<212> TYPE: DNA
<213> ORGANISM: Rattus norvegicus

<400> SEQUENCE: 7

```
gtataagagg aagaacacaa aggtttgcag cagccaggca gaacaccaag ggatcaagat      60
gccgcctaca gtgaggtggt cagcctggtg cacaggatgg ctgtggatct ttggggcagc    120
tctgggccag tgcctggggt atggctcaga gcagcaaagg gtagcatttc ttcagcatcc    180
agggcaaaac catctgcaag caagttatat ggagcttaga cccagccagg ctgtcgccc    240
aggatactat cgagacatca aaagcttccc tgcgggaagg tctgttccct gcaattgcaa    300
cggacattca aatagatgcc aagacggctc gggagtgtgc attaactgtc agcacaacac    360
agctggggag cactgtgagc gttgcaagag gggttactat ggaagcgcca tccatggatc    420
ctgcagggtt tgcccctgtc ctcacaccaa cagctttgcc actggctgtg ctgtggatgg    480
aggagctgtg aggtgtgcct gcaaacccgg atacacagga gcacagtgtg agaggtgtgc    540
accaggatat tttgggaacc cccagaaatt tggaggtagc tgccaaccat gcaattgcaa    600
cagtaatggc cagtttggca cttgtgatcc cctaactgga gactgtgtaa gccaagaacc    660
caaagatggc agccctgcag aagaatgtga tgactgtgac agctgtgtga tgactctcct    720
aaatgacttg gtccccatgg gtgaggaact cgccctggtg aaatcaaaac ttcagggggct    780
gagtgtgaac actggttctc tggaacagat ccggcatgtg agatgcagg ccaaggacct    840
gaggaaccag ctgcttggct tccgttccgc catctccagt cacgggtccc aaatggacgg    900
cctggaaaaa gaactcagtc atttgtacca ggaattcgaa actttgcaag aaaaggcgca    960
ggtcaattcc agaaaagcac aaacattata taacaacatc gatacgacaa tccaaaacgc   1020
```

-continued

```
caaagagttg gacatgaaga ttaaaaacat acttacgaat gtgcacattc tcctgaagca   1080
gatcgctcgg ccaggtggag aaggaatgga cttgccggtg ggcgactggt ccagggagtc   1140
ggcggaagct cagcgcatgt tgcgggagct gcgaggccga gactttaaaa agcacctcca   1200
agaagcagag gcccagaaaa tggaagccca gctcttactg aaccgaatca ggacctggct   1260
ggaatcccac caggtggaga caatggact gctaaagaat attcgggatt cattaaatga    1320
ttatgaagcc aaacttcagg acctgcgttc cgtgcttcag gaggcggcag cccagggaaa   1380
gcaggctaca ggcctcaacc acgaaaatga ggggtccta ggagccatcc agagacaaat    1440
gaaggaaatg gattccctga agaagtacct caccgagcac ctggccacag cagacgcttc   1500
cctgctgcaa accaacagtc tactgcagcg gatggacacg agccagaagg agtatgaaag   1560
cttagctgct gctttaaacg gagcaagaca ggaactgaat gaccaagtgc gggaactctc   1620
cagatccgga ggcaaagcac ccctggtggc tgaggccgag aagcacgctc agtctttaca   1680
ggagctggca aagcagctgg aagagataaa gagaaacacc agtggggatg agtcggtgcg   1740
ctgtgtcgtg gacgctgcca ctgcctatga gagcatcctc aacgccatcc gagcagcaga   1800
ggatgcagcc ggcaaggccg acagtgcctc agagtccgcc ttccagacag tgataaagga   1860
agatcttccg agaagagcca aaccctgag ttctgacagc gaggaactgt taaacgaggc    1920
caagatgaca cggaaaaggc tacagcaaga aatcaatcca gctctcaaca gcctacagca   1980
aaccctgaag actgtatcag ttcagaagga cctgctagat gccaatgtca ctgctgtccg   2040
taatgacctt cgtgggatcc agagaggtga tattgacagt gtggtgagtg gagcgaagag   2100
catggtcagg aaagccaatg ggataacgag cgaggtcctg gacgggctca gccccatcca   2160
gacggatttg ggaaggatta aggacagcta cgggagcaca cggcatgagg acttcaacaa   2220
agctctgatt gacgccaata actcagtaaa gaaattaacc aagaagttgc ctgatctttt   2280
tgtcaagatt gaaagcatca atcaacagtt gctgccctg ggaaacatct ctgacaatgt    2340
agaccgaatc cgagagctca ttacgcaggc cagagatgct gcgaacaagg ttgcaattcc   2400
catgaggttc aatggtaaat ctggtgttga agtccgtctg ccaaatgacc tagaagactt   2460
gaagggatac acgtctctgt ctttgttcct ccaaagacca gacttaagag agaatggagg   2520
cactgaggac atgtttgtaa tgtaccttgg aaacaaggat gcctccaagg actacatcgg   2580
catggcggtt gtagatggcc agctgacgtg tgtctacaac ctgggggacc gagaagctga   2640
agttcagatc gatcaggtcc tgacggagag tgagtctcag gaggcagtta tggaccgggt   2700
gaagttccag agaatatatc aatttgccaa gcttaattac accaaagaag ccacgtccaa   2760
taaacccaaa gctcccgcgg tctacgacct ggagggtggc agtagcaaca cgctccttaa   2820
tttggatccc gaggacgctg tgttttatgt cggaggttac ccaccggatt ttgaacttcc   2880
tagcagactg cggttccctc catacaaagg ctgtatcgaa ctagatgacc tcaatgaaaa   2940
cgttctaagc ttgtacaatt tcaagacaac tttcaatctc aacaccacgg aggtggagcc   3000
ttgtaggagg agaaaggaag agtcagacaa aaattacttt gaaggtacag gctatgctcg   3060
catccctact caaccaaatg ctcccttccc aaacttcata cagaccatcc agactactgt   3120
ggacagaggt ttactgttct tcgcagaaaa ccaggataac ttcatatctc tgaacataga   3180
agatggcaat ctcatggtga gatacaaact aaattcagag ccacccaaag agaagggaat   3240
tcgagacacc atcaacgatg ggaaagatca ttcgatctta atcacaattg gaaaactaca   3300
aaaacgcatg tggataaatg tgaacgaacg cagtgtacga atcgaagggg aaatatttga   3360
tttcagcaca tattatttgg gcggaattcc aattgcaatc agagaaaggt ttaacatctc   3420
```

-continued

```
aacgcctgct tccaaggct gcatgaagaa tctgaagaaa accagtgggg ttgtcaggtt    3480
gaatgatact gtgggtgtaa ccaagaagtg ctcagaagac tggaagcttg tgcgaaccgc    3540
ctcgttctcc agaggagggc agatgagctt acaaacttg gacgtgccct cgactgaccg     3600
cttccagctc tcctttgggt ttcagacctt tcaacccagt ggcacactgc tcaatcatca    3660
gacgcggaca gcagcctgc tggtcaccct ggaagatggg cacattgagt tgagcactag     3720
ggacagcaac atcccaattt tcaagtctcc agggacctac atggacggtt tactgcatca    3780
tgtatctgta ataagtgaca cctcaggtct ccgccttctc atcgatgacc aggtcctgag    3840
aaggaaccag aggcttccta gcttctctaa cgcccagcag tcgctccgcc ttggaggagg    3900
tcatttcgag ggttgtatca gcaatgtttt agtccaaagg ttttcacaga gtccagaagt    3960
cctggatctg ccagtaaat ctaccaagaa ggatgcatcc ctaggaggct gcagtttaaa     4020
caagccacct tttcttatgt tgtttaaaag tcccaagaga tttaacaagg ccggatttt     4080 caatgttaat cagctgatgc aagatgcacc tcaggccaca aggagcacag aggcttggca    4140
agatgggagg tcctgcctac cacctctgaa caccaaggcc tctcacagag ccctgcagtt    4200
tggagacagc cccaccagcc acttgctact caagcttccc caggaactgc tgaaacctag    4260
gtcacagttt tctttagaca tacagacaac ttcccccaaa ggactggtgt tttacgcagg    4320
caccaaggac tccttcctgg ctctttatgt cgcagatggc cgtgttgtct ttgctttggg    4380
ggcaggaggg aagaaactga gactcaggag caaggagaga taccatgacg ggaagtggca    4440
cacggtggtg ttcggactaa atggaggaaa ggcacgcctg gttgtggatg ggctaagggc    4500
ccaggaaggc agtttgcctg gaaattctac catcagcccc agagaacagg tttacctagg    4560
gttgccgcta tcaagaaagc caagagcct accccagcac agttttgtgg ggtgcctgag     4620
agatttccag ttgaactcga aacccctgga ttctccttct gcgaggtttg gggtatctcc    4680
ctgcttgggt ggctctttag agaaaggcat ttatttctcc caaggaggag gccatgtgat    4740
cctagccaat tctgtgtcct tggggccaga gcttaagctc actttcagca ttcgcccacg    4800
gagtctcact ggggtcttaa tacacgtcgg aagtcaatct ggacagcgct taagtgtgta    4860
catggaggca ggaaaggtca caacctctgt gagcagtgat gcaggaggaa gtgtgacatc    4920
aattacaccg aagcagtctc tgtgtgatgg acagtggcac tcggtggcag tctccattaa    4980
acagcgcatc ctgcatctag aactggatac agacagtagc tacacagtcg caccactttc    5040
cttctcacca aacagcaccc gagggtcact gcacgtcgga ggtgtcccag acaaattgaa    5100
aatgcttaca ctccctgtgt ggaactcatt ttttggctgt ctgaagaata ttcaagtcaa    5160
ccatgtccct gtcccatca cagaagccac agaagtccaa ggttctgtca gcctgaatgg     5220
ctgccctgac cactaaccct acacagcaag attcaccttt ggag                    5264
```

<210> SEQ ID NO 8
<211> LENGTH: 1725
<212> TYPE: PRT
<213> ORGANISM: Rattus norvegicus

<400> SEQUENCE: 8

Met Pro Pro Thr Val Arg Trp Ser Ala Trp Cys Thr Gly Trp Leu Trp
1               5                   10                  15

Ile Phe Gly Ala Ala Leu Gly Gln Cys Leu Gly Tyr Gly Ser Glu Gln
                20                  25                  30

Gln Arg Val Ala Phe Leu Gln His Pro Gly Gln Asn His Leu Gln Ala
        35                  40                  45

```
Ser Tyr Met Glu Leu Arg Pro Ser Gln Gly Cys Arg Pro Gly Tyr Tyr
 50                  55                  60
Arg Asp Ile Lys Ser Phe Pro Ala Gly Arg Ser Val Pro Cys Asn Cys
 65                  70                  75                  80
Asn Gly His Ser Asn Arg Cys Gln Asp Gly Ser Gly Val Cys Ile Asn
                 85                  90                  95
Cys Gln His Asn Thr Ala Gly Glu His Cys Glu Arg Cys Lys Arg Gly
                100                 105                 110
Tyr Tyr Gly Ser Ala Ile His Gly Ser Cys Arg Val Cys Pro Cys Pro
            115                 120                 125
His Thr Asn Ser Phe Ala Thr Gly Cys Ala Val Asp Gly Gly Ala Val
        130                 135                 140
Arg Cys Ala Cys Lys Pro Gly Tyr Thr Gly Ala Gln Cys Glu Arg Cys
145                 150                 155                 160
Ala Pro Gly Tyr Phe Gly Asn Pro Gln Lys Phe Gly Gly Ser Cys Gln
                165                 170                 175
Pro Cys Asn Cys Asn Ser Asn Gly Gln Phe Gly Thr Cys Asp Pro Leu
            180                 185                 190
Thr Gly Asp Cys Val Ser Gln Glu Pro Lys Asp Gly Ser Pro Ala Glu
        195                 200                 205
Glu Cys Asp Asp Cys Asp Ser Cys Val Met Thr Leu Leu Asn Asp Leu
    210                 215                 220
Val Pro Met Gly Glu Glu Leu Ala Leu Val Lys Ser Lys Leu Gln Gly
225                 230                 235                 240
Leu Ser Val Asn Thr Gly Ser Leu Glu Gln Ile Arg His Val Glu Met
                245                 250                 255
Gln Ala Lys Asp Leu Arg Asn Gln Leu Leu Gly Phe Arg Ser Ala Ile
            260                 265                 270
Ser Ser His Gly Ser Gln Met Asp Gly Leu Glu Lys Glu Leu Ser His
        275                 280                 285
Leu Tyr Gln Glu Phe Glu Thr Leu Gln Glu Lys Ala Gln Val Asn Ser
    290                 295                 300
Arg Lys Ala Gln Thr Leu Tyr Asn Asn Ile Asp Thr Thr Ile Gln Asn
305                 310                 315                 320
Ala Lys Glu Leu Asp Met Lys Ile Lys Asn Ile Leu Thr Asn Val His
                325                 330                 335
Ile Leu Leu Lys Gln Ile Ala Arg Pro Gly Gly Glu Gly Met Asp Leu
            340                 345                 350
Pro Val Gly Asp Trp Ser Arg Glu Ser Ala Glu Ala Gln Arg Met Leu
        355                 360                 365
Arg Glu Leu Arg Gly Arg Asp Phe Lys Lys His Leu Gln Glu Ala Glu
    370                 375                 380
Ala Gln Lys Met Glu Ala Gln Leu Leu Leu Asn Arg Ile Arg Thr Trp
385                 390                 395                 400
Leu Glu Ser His Gln Val Glu Asn Asn Gly Leu Leu Lys Asn Ile Arg
                405                 410                 415
Asp Ser Leu Asn Asp Tyr Glu Ala Lys Leu Gln Asp Leu Arg Ser Val
            420                 425                 430
Leu Gln Glu Ala Ala Ala Gln Gly Lys Gln Ala Thr Gly Leu Asn His
        435                 440                 445
Glu Asn Glu Gly Val Leu Gly Ala Ile Gln Arg Gln Met Lys Glu Met
    450                 455                 460
```

-continued

```
Asp Ser Leu Lys Lys Tyr Leu Thr Glu His Leu Ala Thr Asp Ala
465                 470                 475                 480

Ser Leu Leu Gln Thr Asn Ser Leu Leu Gln Arg Met Asp Thr Ser Gln
            485                 490                 495

Lys Glu Tyr Glu Ser Leu Ala Ala Ala Leu Asn Gly Ala Arg Gln Glu
        500                 505                 510

Leu Asn Asp Gln Val Arg Glu Leu Ser Arg Ser Gly Lys Ala Pro
            515                 520                 525

Leu Val Ala Glu Ala Glu Lys His Ala Gln Ser Leu Gln Glu Leu Ala
        530                 535                 540

Lys Gln Leu Glu Glu Ile Lys Arg Asn Thr Ser Gly Asp Glu Ser Val
545                 550                 555                 560

Arg Cys Val Val Asp Ala Ala Thr Ala Tyr Glu Ser Ile Leu Asn Ala
                565                 570                 575

Ile Arg Ala Ala Glu Asp Ala Ala Gly Lys Ala Asp Ser Ala Ser Glu
            580                 585                 590

Ser Ala Phe Gln Thr Val Ile Lys Glu Asp Leu Pro Arg Arg Ala Lys
        595                 600                 605

Thr Leu Ser Ser Asp Ser Glu Glu Leu Leu Asn Glu Ala Lys Met Thr
    610                 615                 620

Arg Lys Arg Leu Gln Gln Glu Ile Asn Pro Ala Leu Asn Ser Leu Gln
625                 630                 635                 640

Gln Thr Leu Lys Thr Val Ser Val Gln Lys Asp Leu Leu Asp Ala Asn
                645                 650                 655

Val Thr Ala Val Arg Asn Asp Leu Arg Gly Ile Gln Arg Gly Asp Ile
            660                 665                 670

Asp Ser Val Val Ser Gly Ala Lys Ser Met Val Arg Lys Ala Asn Gly
        675                 680                 685

Ile Thr Ser Glu Val Leu Asp Gly Leu Ser Pro Ile Gln Thr Asp Leu
    690                 695                 700

Gly Arg Ile Lys Asp Ser Tyr Gly Ser Thr Arg His Glu Asp Phe Asn
705                 710                 715                 720

Lys Ala Leu Ile Asp Ala Asn Asn Ser Val Lys Lys Leu Thr Lys Lys
                725                 730                 735

Leu Pro Asp Leu Phe Val Lys Ile Glu Ser Ile Asn Gln Gln Leu Leu
            740                 745                 750

Pro Leu Gly Asn Ile Ser Asp Asn Val Asp Arg Ile Arg Glu Leu Ile
        755                 760                 765

Thr Gln Ala Arg Asp Ala Ala Asn Lys Val Ala Ile Pro Met Arg Phe
    770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asp Leu
                805                 810                 815

Arg Glu Asn Gly Gly Thr Glu Asp Met Phe Val Met Tyr Leu Gly Asn
            820                 825                 830

Lys Asp Ala Ser Lys Asp Tyr Ile Gly Met Ala Val Val Asp Gly Gln
        835                 840                 845

Leu Thr Cys Val Tyr Asn Leu Gly Asp Arg Glu Ala Glu Val Gln Ile
    850                 855                 860

Asp Gln Val Leu Thr Glu Ser Glu Ser Gln Glu Ala Val Met Asp Arg
865                 870                 875                 880

Val Lys Phe Gln Arg Ile Tyr Gln Phe Ala Lys Leu Asn Tyr Thr Lys
```

-continued

```
            885                 890                 895
Glu Ala Thr Ser Asn Lys Pro Lys Ala Pro Ala Val Tyr Asp Leu Glu
            900                 905                 910
Gly Gly Ser Ser Asn Thr Leu Leu Asn Leu Asp Pro Glu Asp Ala Val
            915                 920                 925
Phe Tyr Val Gly Gly Tyr Pro Pro Asp Phe Glu Leu Pro Ser Arg Leu
            930                 935                 940
Arg Phe Pro Pro Tyr Lys Gly Cys Ile Glu Leu Asp Asp Leu Asn Glu
945                 950                 955                 960
Asn Val Leu Ser Leu Tyr Asn Phe Lys Thr Thr Phe Asn Leu Asn Thr
            965                 970                 975
Thr Glu Val Glu Pro Cys Arg Arg Arg Lys Glu Glu Ser Asp Lys Asn
            980                 985                 990
Tyr Phe Glu Gly Thr Gly Tyr Ala Arg Ile Pro Thr Gln Pro Asn Ala
            995                 1000                1005
Pro Phe Pro Asn Phe Ile Gln Thr Ile Gln Thr Thr Val Asp Arg
            1010                1015                1020
Gly Leu Leu Phe Phe Ala Glu Asn Gln Asp Asn Phe Ile Ser Leu
            1025                1030                1035
Asn Ile Glu Asp Gly Asn Leu Met Val Arg Tyr Lys Leu Asn Ser
            1040                1045                1050
Glu Pro Pro Lys Glu Lys Gly Ile Arg Asp Thr Ile Asn Asp Gly
            1055                1060                1065
Lys Asp His Ser Ile Leu Ile Thr Ile Gly Lys Leu Gln Lys Arg
            1070                1075                1080
Met Trp Ile Asn Val Asn Glu Arg Ser Val Arg Ile Glu Gly Glu
            1085                1090                1095
Ile Phe Asp Phe Ser Thr Tyr Tyr Leu Gly Gly Ile Pro Ile Ala
            1100                1105                1110
Ile Arg Glu Arg Phe Asn Ile Ser Thr Pro Ala Phe Gln Gly Cys
            1115                1120                1125
Met Lys Asn Leu Lys Lys Thr Ser Gly Val Val Arg Leu Asn Asp
            1130                1135                1140
Thr Val Gly Val Thr Lys Lys Cys Ser Glu Asp Trp Lys Leu Val
            1145                1150                1155
Arg Thr Ala Ser Phe Ser Arg Gly Gly Gln Met Ser Phe Thr Asn
            1160                1165                1170
Leu Asp Val Pro Ser Thr Asp Arg Phe Gln Leu Ser Phe Gly Phe
            1175                1180                1185
Gln Thr Phe Gln Pro Ser Gly Thr Leu Leu Asn His Gln Thr Arg
            1190                1195                1200
Thr Ser Ser Leu Leu Val Thr Leu Glu Asp Gly His Ile Glu Leu
            1205                1210                1215
Ser Thr Arg Asp Ser Asn Ile Pro Ile Phe Lys Ser Pro Gly Thr
            1220                1225                1230
Tyr Met Asp Gly Leu Leu His His Val Ser Val Ile Ser Asp Thr
            1235                1240                1245
Ser Gly Leu Arg Leu Leu Ile Asp Asp Gln Val Leu Arg Arg Asn
            1250                1255                1260
Gln Arg Leu Pro Ser Phe Ser Asn Ala Gln Gln Ser Leu Arg Leu
            1265                1270                1275
Gly Gly Gly His Phe Glu Gly Cys Ile Ser Asn Val Leu Val Gln
            1280                1285                1290
```

-continued

Arg Phe Ser Gln Ser Pro Glu Val Leu Asp Leu Ala Ser Lys Ser
    1295                1300                1305

Thr Lys Lys Asp Ala Ser Leu Gly Gly Cys Ser Leu Asn Lys Pro
    1310                1315                1320

Pro Phe Leu Met Leu Phe Lys Ser Pro Lys Arg Phe Asn Lys Gly
    1325                1330                1335

Arg Ile Phe Asn Val Asn Gln Leu Met Gln Asp Ala Pro Gln Ala
    1340                1345                1350

Thr Arg Ser Thr Glu Ala Trp Gln Asp Gly Arg Ser Cys Leu Pro
    1355                1360                1365

Pro Leu Asn Thr Lys Ala Ser His Arg Ala Leu Gln Phe Gly Asp
    1370                1375                1380

Ser Pro Thr Ser His Leu Leu Leu Lys Leu Pro Gln Glu Leu Leu
    1385                1390                1395

Lys Pro Arg Ser Gln Phe Ser Leu Asp Ile Gln Thr Thr Ser Pro
    1400                1405                1410

Lys Gly Leu Val Phe Tyr Ala Gly Thr Lys Asp Ser Phe Leu Ala
    1415                1420                1425

Leu Tyr Val Ala Asp Gly Arg Val Val Phe Ala Leu Gly Ala Gly
    1430                1435                1440

Gly Lys Lys Leu Arg Leu Arg Ser Lys Glu Arg Tyr His Asp Gly
    1445                1450                1455

Lys Trp His Thr Val Val Phe Gly Leu Asn Gly Gly Lys Ala Arg
    1460                1465                1470

Leu Val Val Asp Gly Leu Arg Ala Gln Glu Gly Ser Leu Pro Gly
    1475                1480                1485

Asn Ser Thr Ile Ser Pro Arg Glu Gln Val Tyr Leu Gly Leu Pro
    1490                1495                1500

Leu Ser Arg Lys Pro Lys Ser Leu Pro Gln His Ser Phe Val Gly
    1505                1510                1515

Cys Leu Arg Asp Phe Gln Leu Asn Ser Lys Pro Leu Asp Ser Pro
    1520                1525                1530

Ser Ala Arg Phe Gly Val Ser Pro Cys Leu Gly Gly Ser Leu Glu
    1535                1540                1545

Lys Gly Ile Tyr Phe Ser Gln Gly Gly Gly His Val Ile Leu Ala
    1550                1555                1560

Asn Ser Val Ser Leu Gly Pro Glu Leu Lys Leu Thr Phe Ser Ile
    1565                1570                1575

Arg Pro Arg Ser Leu Thr Gly Val Leu Ile His Val Gly Ser Gln
    1580                1585                1590

Ser Gly Gln Arg Leu Ser Val Tyr Met Glu Ala Gly Lys Val Thr
    1595                1600                1605

Thr Ser Val Ser Ser Asp Ala Gly Gly Ser Val Thr Ser Ile Thr
    1610                1615                1620

Pro Lys Gln Ser Leu Cys Asp Gly Gln Trp His Ser Val Ala Val
    1625                1630                1635

Ser Ile Lys Gln Arg Ile Leu His Leu Glu Leu Asp Thr Asp Ser
    1640                1645                1650

Ser Tyr Thr Val Ala Pro Leu Ser Phe Ser Pro Asn Ser Thr Arg
    1655                1660                1665

Gly Ser Leu His Val Gly Gly Val Pro Asp Lys Leu Lys Met Leu
    1670                1675                1680

| Thr | Leu | Pro | Val | Trp | Asn | Ser | Phe | Phe | Gly | Cys | Leu | Lys | Asn | Ile |
| | 1685 | | | | 1690 | | | | | 1695 | | | | |

| Gln | Val | Asn | His | Val | Pro | Val | Pro | Ile | Thr | Glu | Ala | Thr | Glu | Val |
| | 1700 | | | | | 1705 | | | | | 1710 | | | |

| Gln | Gly | Ser | Val | Ser | Leu | Asn | Gly | Cys | Pro | Asp | His |
| | 1715 | | | | | 1720 | | | | | 1725 |

<210> SEQ ID NO 9
<211> LENGTH: 7323
<212> TYPE: DNA
<213> ORGANISM: Mus musculus

<400> SEQUENCE: 9

```
atgtcagagg gcatttgctg ccgagctggc gcactgtgca agagtggaca gcaagtttcc      60
actgtggtgg tggtagatcc accaaaccat gccagtggaa tgagaactga atgcagccca     120
ccagagcacg tgcacacgtg cattaaggaa cctcagaatc agctcttcca tgtggcttat     180
atcttaatca aatttgcaaa ctctccccgc cctgatcttt ggatcctgga agatctgta     240
gactttggaa gcacctactc accatggcag tattttgctc attctagaag agattgtgta     300
gaacagtttg ggcaagaagc aaacatggca attacccagg acgaccagat gctctgtgtc     360
acggagtatt cccgtatcgt gcctctggaa aatggcgaga ttgttgtatc cttgataaat     420
ggtcgtccag gtgcaaaaaa gtttgctttc tctgacactc tgagggagtt tactaaggca     480
acaaacatcc gcttgcggtt tctgcgaacc aacacccctcc tcgggcatct tatttccaag     540
gcagagcgag accccactgt cacgcgccgg tattattgca tggaagctga tgatgctctg     600
ttctctgtcc tgcagtatta ttacagcata aaggatatca gtgttggtgg gcggtgtgtt     660
tgcaacggcc atgcggaggc gtgcagtgct gacaaccctg aaaagcagtt ccgatgcgaa     720
tgccagcacc atacctgtgg agacacgtgt aaccgctgct gtgcaggtta caatcagagg     780
cgctggcagc ctgctggtca ggagcagcac aatgagtgtg aagcctgcaa ctgccatggg     840
catgctgtgg actgctacta tgacccagac gtggagcacc agcaggcgag cttgaacagc     900
aaaggcgtct acgcaggtgg aggggtctgc atcaactgtc agcacaacac tgcaggcgtg     960
aactgtgaaa agtgtgcgaa gggttacttc cggccccatg agttccggt ggatgcactg    1020
catgcgatgca tcccttgcag ctgtgaccca gaacgcgcag atgactgtga ccagggctca    1080
ggccactgcc attgtaagcc aaatttctcc ggagactact gtgagacgtg tgcagatggg    1140
tactataatt ttccattttg cttgagaatt ccagtctttc caactacac tccaagtcca    1200
gaagatccag tggctggcaa tataaaaggc aaggatccag ggactctaga cccaccagtc    1260
atagcaaatg gggcatatct tggagcttca agactagagc aaggagccac aggccagggc    1320
agccctgctg agagggtcac ccacaccaac tcatggctga gttcctcaat gcctatgctc    1380
caggttaggg ctgccatcca tgaggctaag tgttactctc tgtgtttctg tatgtatgtt    1440
gagcacagtg ggactgtacc acctgctctg gggtcaggtt atacagggga ctctgagcct    1500
aaaacaggaa cccaggcaaa aggggggtgt gactgtaact tggaaggtgt tctcccagag    1560
atatgtgacg atcgtggcag gtgcctgtgc cgccctgggg ttgagggtcc ccagtgtgac    1620
tcctgccgct cgggctccta ttcatttccc atatgccaag cttgccagtg ttcgacgatt    1680
ggatcctatc cagtgccctg tgacccgggg aatggccagt gtgactgcct gcctggaatt    1740
accgggaggc agtgtgacag gtgtctctcg ggagcctatg actttccata ctgccaaggt    1800
aaggaagccg gcagcatgtt ggaggctcgg tcctcatctg agtgggtgca gctgacctct    1860
```

```
tggagaagcc tgggttattg tcagtgcaag cagcatgttg caagtcctac atgtagtgtc    1920
tgcaaaccat tatattggaa tctggccaaa gaaaacccc gtggatgctc agagtgccag    1980
tgccatgaag cagggacatt gagtggaatt ggagagtgtg ggcaggagga cggtgactgt    2040
agctgcaaag cccatgtaac tggtgatgcc tgcgacacct gtgaagatgg gttttctct    2100 ttggagaaga gcaattactt tggctgtcaa gggtgtcagt gtgacattgg tggagcactc    2160
accaccatgt gtagtgggcc ctcgggagta tgccagtgca gagagcacgt ggaggggaaa    2220
cagtgccaga ggcctgaaaa taactactac ttcccggatt tgcaccacat gaagtatgag    2280
gtcgaagatg gcactggacc taatggaaga aacctgcggt ttggatttga tcccctggta    2340
ttccctgagt ttagctggag aggatatgct ccaatgacct cagtccaggt atatatgagt    2400
gagtgtgtgt gtcctctaca ctgcatgtta ttttggggta cttttcagaa tgaagtaagg    2460
gtgagattgt ctgtgaggca gtccagcctc tccttgttcc gcatcgttct gagatacatc    2520
agtcctggaa cggaagccat atccggccga atcactcttt actcatcgca gggagattcg    2580
gatgctttgc aaagcagaaa atcacccttt ccccgagta aagagccagc ctttgtcaca    2640
gtccctggga atggctttgc aggcccattc tccatcacac ctgggacgtg gattgcttgc    2700
atccaggtgg aaggagtcct tctggactac ctggtgctgc ttcccaggga ctactatgaa    2760
gcattcaccc tgcaagtgcc agtcacagag ccatgtgccc acacaggatc tccccaggac    2820
aactgtttgc tttaccagca tttaccactg actgcattct cctgtaccct ggcttgtgag    2880
gccagacact tcctgctgga tggagagctg agacccttgg caatgaggca gcccacaccc    2940
acacacccag ccatggtgga cctcagcggg agagaggtag aactgcagct tcgtctgcgg    3000
gtcccacagg ttggccacta cgtggtcctg ctggagtatg ccacggaggt ggagcagctt    3060
tttgtggtgg acgtgaatct gaagagctca gggtctgcct tggcaggcca ggtgaacata    3120
tacagctgca gtacagcat cccgtgcagg agtgtggtga ttgacagcct gagtcgcacg    3180
gctgtacatg agctgttggc agatgcagac attcagctca aggcgcacat ggcccatttc    3240
cttttgtatc acatttgtat tataccagct gaagaattct caactgaata tttgagacct    3300
caagtccact gcattgccag ctacaggcag catgctaatc caagtgcttc ctgtgtctcc    3360
ctggcccatg aaactcctcc aacagcctca attttggatg ctacaagtag ggccttttc    3420 tctgccctac ctcatgagcc ttcctctcct gcagatggag ttactctgaa ggcaccacag    3480
agtcaagtga ccctgaaagg actcatacca cacctgggcc gacacgtctt tgtcatccat    3540
ttttatcaag cagagcaccc agggtttccc actgaggtga ttgtgaatgg aggaagacag    3600
tggtcaggtt ccttccttgc ctccttctgt ccccacttac ttggctgccg ggaccaggtg    3660
atctctgatg gccaagtgga gtttgacatc tctgaagcag aggtagctgt gacagtgaag    3720
attccagatg gaaagtcctt aacattggtc cgggttctag tggtacctgc agagaattac    3780
gactaccaaa ttcttcacaa aacaacagtg gacaagtcct ccgagttcat cagcagttgt    3840
ggaggagaca gctttttatat tgatccccag gcagcctctg gattctgtaa gaattctgca    3900
aggtccctgg tagcctttta ccataacggt gccatacccc tgtgagtgcga ccctgctggg    3960 actgccggcc accactgtag tcctgagggt gggcagtgcc cttgccggcc caatgtcatc    4020
gggaggcagt gcagccgctg tgcgacaggc tactatggat tcccatactg caagccttgt    4080
aattgtggca gacgcctttg tgaagaggtg acagggaagt gtctctgccc accccacaca    4140
gtcaggcctc agtgtgaggt ctgtgagatg aattccttca actttcaccc tgtggctggc    4200
tgtgacgtct gcaactgctc caggaagggc accattgagg cggccgtctc tgagtgtgac    4260
```

-continued

```
agggacagcg ggcagtgcag gtgcaagcct agagtcacag ggcagcagtg tgacaagtgt    4320
gctcctggct tctaccagtt ccctgagtgt gtccctgca gctgtaacag agatgggact    4380
gagcccagcg tatgtgaccc agagactggg gcttgcatgt gcaaggaaaa tgtagagggc    4440
ccccaatgtc aactgtgtcg agaaggatca ttctacctgg acccaacaaa cccaaagggt    4500
tgtaccaagt gcttctgttt tggagtgaat actgactgtc agagttcgca taagcaacga    4560
gctaagtttg tagacatgat gggctggcgt ctggagacag cagatggagt tgatgtccct    4620
gtgtccttca accctggcag caacagcatg tggcagatc tgcaggagct gccaccctca    4680
gttcacagtg catcctgggt ggcacctcca tcctacctag gtgataaggt atcatcgtac    4740
ggcggctacc tcacctacca cgccaagtcc tttggcttac ctggagatat ggttcttctg    4800
ggaaagcagc cagatgtgca gctcactggt caacacatgt ccctcatcca taaggaaccc    4860
agcgacccac ggccagacag gctgcatcac ggaagagtgc aagtgattga gggaaacttc    4920
agacacgaag gcagcagtgc cccagtgtcc cgggaggagc tgatgactgt gctgtccaga    4980
ctggaaagac tccacatccg gggcctccat ttcaccgaga cacagcggct caccttgggt    5040
gaggtagggc tggaggaggc ctctgacacg ggaagcggac ccagggctca tcttgtggag    5100
atgtgtgcct gcccccctga ctacacaggt gactcatgcc agggttgtcg ccctggatac    5160
tattgggaca acaaaagctt acctgtagga aggtgtgttc cctgcaattg caacggacat    5220
tcaaatagat gccaggatgg ctccgggata tgcattaact gtcagcacaa cacagctggg    5280
gagcactgtg agcgttgcca agcaggtcac tatggaaatg ccatccacgg atcttgtagg    5340
gtctgcccct gccctcatac caacagtttt gccaccggct gtgctgtgga tggtggagct    5400
gtgaggtgtg cctgcaaacc cggatacaca ggaacacagt gtgagaggtg tgcaccagga    5460
tattttggga accccagaa atttggaggt agctgccagc catgcaattg taacagcaat    5520
ggccagttag gtccttgcga ccccctaact ggagactgta taaccaaga acccaaagat    5580 ggcagccctg cagaagaatg tgatgactgc gacagctgtg tgatgacgct cttaaatgac    5640
ttggcctcca tgggtgagga actccgcctg gtgaagtcaa agctgcaggg gctgagtgtg    5700
agcacgggtg ctctggaaca gatccggcac atggagacgc aggccaagga cctgaggaac    5760
cagctgcttg gcttccgttc tgccacctca agtcatgggt ccaaaatgga tgacctggaa    5820
aaagagctga gtcatttgaa ccgggaattt gaaactctgc agaaaaggc acaggtcaat    5880 tccagaaaag cacaaacatt atataacaac attgatcaga caatccaaag tgccaaagaa    5940
ctggacatga agattaaaaa catcgttcag aatgtgcaca ttctcctgaa gcagatggcg    6000
aggccaggtg gagaaggcac ggacttgcca gtgggtgact ggtccaggga gctgccgaa    6060 gctcaacgca tgatgcgaga cctgcgaagc cgagacttta aaaagcacct ccaagaagca    6120
gaggccgaga aaatggaagc ccagctctta ctgcaccgga tcaggacctg gctgaatcc    6180 caccaggtgg agaacaacgg actgctaaag aatattcggg actccttaaa tgattatgaa    6240
gacaaacttc aggacctacg ttccatcctc caggaggcag ctgcccaggc aaagcaggcc    6300
actggcatca accatgaaaa tgagggggtt ctcggagcca tccagagaca aatgaaagaa    6360
atggattccc tgaagaatga cttcaccaag tacctggcca cagccgactc ttccctgctg    6420
cagaccaaca atctactgca gcagatggac aaaagccaga aggaatatga aagcttagct    6480
gctgctttaa atgagcaag acaggaactg agtgacagag tgcgagaact gtccagatcg    6540
ggtggcaaag caccgctggt ggtggaggca gagaagcatg cacagtcttt acaggagctg    6600
```

```
gcaaagcagc tggaagagat aaagagaaac accagcgggg atgagctggt gcgttgtgct    6660
gtggatgctg ccacggccta tgagaacatc ctcaatgcca tcagagcagc agaggatgca    6720
gccagcaagg ccaccagtgc ctccaagtct gccttccaaa cagtgataaa ggaagacctt    6780
ccaaaaagag ctaagaccct gagttctgac agcgaggaac tgttaaatga agccaagatg    6840
acacagaaaa ggctacagca agtcagtcca gctctcaaca gcctacaaca aaccctgaag    6900
actgtatcag ttcagaagga cctgctagat gccaacctca ctgttgcccg tgatgatctt    6960
catgggatac agagaggtga tatcgacagt gtggtgatcg gtgcaaagag catggtcagg    7020
gaagccaacg gaataacaag cgaggtcctg gacgggctca accccatcca gacagatttg    7080
ggaaggatta aggacagcta tgagagcgca cggcgtgaag acttcagcaa ggctctggtc    7140
gatgccaata actcagtaaa gaaattaacc aggaagttgc ctgatctttt tatcaagatt    7200
gaaagtatca accaacagtt gctgcccctg gggaacatct ctgacaatgt ggaccgaatc    7260
cgagaactca ttcagcaggc cagagatgct gcaaacaagg tgggtattcc catttggctc    7320
tag                                                                  7323
```

<210> SEQ ID NO 10
<211> LENGTH: 2440
<212> TYPE: PRT
<213> ORGANISM: Mus musculus

<400> SEQUENCE: 10

```
Met Ser Glu Gly Ile Cys Cys Arg Ala Gly Ala Leu Cys Lys Ser Gly
1               5                   10                  15

Gln Gln Val Ser Thr Val Val Val Asp Pro Pro Asn His Ala Ser
                20                  25                  30

Gly Met Arg Thr Glu Cys Ser Pro Glu His Val His Thr Cys Ile
                35                  40                  45

Lys Glu Pro Gln Asn Gln Leu Phe His Val Ala Tyr Ile Leu Ile Lys
    50                  55                  60

Phe Ala Asn Ser Pro Arg Pro Asp Leu Trp Ile Leu Glu Arg Ser Val
65                  70                  75                  80

Asp Phe Gly Ser Thr Tyr Ser Pro Trp Gln Tyr Phe Ala His Ser Arg
                85                  90                  95

Arg Asp Cys Val Glu Gln Phe Gly Gln Glu Ala Asn Met Ala Ile Thr
                100                 105                 110

Gln Asp Asp Gln Met Leu Cys Val Thr Glu Tyr Ser Arg Ile Val Pro
        115                 120                 125

Leu Glu Asn Gly Glu Ile Val Val Ser Leu Ile Asn Gly Arg Pro Gly
    130                 135                 140

Ala Lys Lys Phe Ala Phe Ser Asp Thr Leu Arg Glu Phe Thr Lys Ala
145                 150                 155                 160

Thr Asn Ile Arg Leu Arg Phe Leu Arg Thr Asn Thr Leu Leu Gly His
                165                 170                 175

Leu Ile Ser Lys Ala Glu Arg Asp Pro Thr Val Thr Arg Arg Tyr Tyr
                180                 185                 190

Cys Met Glu Ala Asp Asp Ala Leu Phe Ser Val Leu Gln Tyr Tyr Tyr
        195                 200                 205

Ser Ile Lys Asp Ile Ser Val Gly Gly Arg Cys Val Cys Asn Gly His
    210                 215                 220

Ala Glu Ala Cys Ser Ala Asp Asn Pro Glu Lys Gln Phe Arg Cys Glu
225                 230                 235                 240
```

-continued

```
Cys Gln His His Thr Cys Gly Asp Thr Cys Asn Arg Cys Cys Ala Gly
                245                 250                 255
Tyr Asn Gln Arg Arg Trp Gln Pro Ala Gly Gln Glu Gln His Asn Glu
                260                 265                 270
Cys Glu Ala Cys Asn Cys His Gly His Ala Val Asp Cys Tyr Tyr Asp
            275                 280                 285
Pro Asp Val Glu His Gln Gln Ala Ser Leu Asn Ser Lys Gly Val Tyr
        290                 295                 300
Ala Gly Gly Val Cys Ile Asn Cys Gln His Asn Thr Ala Gly Val
305                 310                 315                 320
Asn Cys Glu Lys Cys Ala Lys Gly Tyr Phe Arg Pro His Gly Val Pro
                325                 330                 335
Val Asp Ala Leu His Gly Cys Ile Pro Cys Ser Cys Asp Pro Glu Arg
                340                 345                 350
Ala Asp Asp Cys Asp Gln Gly Ser Gly His Cys His Cys Lys Pro Asn
                355                 360                 365
Phe Ser Gly Asp Tyr Cys Glu Thr Cys Ala Asp Gly Tyr Tyr Asn Phe
        370                 375                 380
Pro Phe Cys Leu Arg Ile Pro Val Phe Pro Asn Tyr Thr Pro Ser Pro
385                 390                 395                 400
Glu Asp Pro Val Ala Gly Asn Ile Lys Gly Lys Asp Pro Gly Thr Leu
                405                 410                 415
Asp Pro Pro Val Ile Ala Asn Gly Ala Tyr Leu Gly Ala Ser Arg Leu
                420                 425                 430
Glu Gln Gly Ala Thr Gly Gln Gly Ser Pro Ala Glu Arg Val Thr His
            435                 440                 445
Thr Asn Ser Trp Leu Ser Ser Met Pro Met Leu Gln Val Arg Ala
450                 455                 460
Ala Ile His Glu Ala Lys Cys Tyr Ser Leu Cys Phe Cys Met Tyr Val
465                 470                 475                 480
Glu His Ser Gly Thr Val Pro Pro Ala Leu Gly Ser Gly Tyr Thr Gly
                485                 490                 495
Asp Ser Glu Pro Lys Thr Gly Thr Gln Ala Lys Arg Gly Cys Asp Cys
            500                 505                 510
Asn Leu Glu Gly Val Leu Pro Glu Ile Cys Asp Asp Arg Gly Arg Cys
            515                 520                 525
Leu Cys Arg Pro Gly Val Glu Gly Pro Gln Cys Asp Ser Cys Arg Ser
        530                 535                 540
Gly Ser Tyr Ser Phe Pro Ile Cys Gln Ala Cys Gln Cys Ser Thr Ile
545                 550                 555                 560
Gly Ser Tyr Pro Val Pro Cys Asp Pro Gly Asn Gly Gln Cys Asp Cys
                565                 570                 575
Leu Pro Gly Ile Thr Gly Arg Gln Cys Asp Arg Cys Leu Ser Gly Ala
                580                 585                 590
Tyr Asp Phe Pro Tyr Cys Gln Gly Lys Glu Ala Gly Ser Met Leu Glu
        595                 600                 605
Ala Arg Ser Ser Ser Glu Trp Val Gln Leu Thr Ser Trp Arg Ser Leu
        610                 615                 620
Gly Tyr Cys Gln Cys Lys Gln His Val Ala Ser Pro Thr Cys Ser Val
625                 630                 635                 640
Cys Lys Pro Leu Tyr Trp Asn Leu Ala Lys Glu Asn Pro Arg Gly Cys
                645                 650                 655
Ser Glu Cys Gln Cys His Glu Ala Gly Thr Leu Ser Gly Ile Gly Glu
```

-continued

```
                660                665                670
Cys Gly Gln Glu Asp Gly Asp Cys Ser Cys Lys Ala His Val Thr Gly
            675                680                685
Asp Ala Cys Asp Thr Cys Glu Asp Gly Phe Phe Ser Leu Glu Lys Ser
        690                695                700
Asn Tyr Phe Gly Cys Gln Gly Cys Gln Cys Asp Ile Gly Gly Ala Leu
705                710                715                720
Thr Thr Met Cys Ser Gly Pro Ser Gly Val Cys Gln Cys Arg Glu His
                725                730                735
Val Glu Gly Lys Gln Cys Gln Arg Pro Glu Asn Asn Tyr Tyr Phe Pro
            740                745                750
Asp Leu His His Met Lys Tyr Glu Val Glu Asp Gly Thr Gly Pro Asn
        755                760                765
Gly Arg Asn Leu Arg Phe Gly Phe Asp Pro Leu Val Phe Pro Glu Phe
770                775                780
Ser Trp Arg Gly Tyr Ala Pro Met Thr Ser Gln Val Tyr Met Ser
785                790                795                800
Glu Cys Val Cys Pro Leu His Cys Met Leu Phe Trp Gly Thr Phe Gln
                805                810                815
Asn Glu Val Arg Val Arg Leu Ser Val Arg Gln Ser Ser Leu Ser Leu
            820                825                830
Phe Arg Ile Val Leu Arg Tyr Ile Ser Pro Gly Thr Glu Ala Ile Ser
        835                840                845
Gly Arg Ile Thr Leu Tyr Ser Ser Gln Gly Asp Ser Asp Ala Leu Gln
        850                855                860
Ser Arg Lys Ile Thr Phe Pro Pro Ser Lys Glu Pro Ala Phe Val Thr
865                870                875                880
Val Pro Gly Asn Gly Phe Ala Gly Pro Phe Ser Ile Thr Pro Gly Thr
                885                890                895
Trp Ile Ala Cys Ile Gln Val Glu Gly Val Leu Leu Asp Tyr Leu Val
                900                905                910
Leu Leu Pro Arg Asp Tyr Tyr Glu Ala Phe Thr Leu Gln Val Pro Val
            915                920                925
Thr Glu Pro Cys Ala His Thr Gly Ser Pro Gln Asp Asn Cys Leu Leu
930                935                940
Tyr Gln His Leu Pro Leu Thr Ala Phe Ser Cys Thr Leu Ala Cys Glu
945                950                955                960
Ala Arg His Phe Leu Leu Asp Gly Glu Leu Arg Pro Leu Ala Met Arg
                965                970                975
Gln Pro Thr Pro Thr His Pro Ala Met Val Asp Leu Ser Gly Arg Glu
            980                985                990
Val Glu Leu Gln Leu Arg Leu Arg  Val Pro Gln Val Gly  His Tyr Val
            995                1000               1005
Val Leu  Leu Glu Tyr Ala Thr  Glu Val Glu Gln Leu  Phe Val Val
            1010               1015               1020
Asp Val  Asn Leu Lys Ser Ser  Gly Ser Ala Leu Ala  Gly Gln Val
            1025               1030               1035
Asn Ile  Tyr Ser Cys Lys Tyr  Ser Ile Pro Cys Arg  Ser Val Val
            1040               1045               1050
Ile Asp  Ser Leu Ser Arg Thr  Ala Val His Glu Leu  Leu Ala Asp
            1055               1060               1065
Ala Asp  Ile Gln Leu Lys Ala  His Met Ala His Phe  Leu Leu Tyr
            1070               1075               1080
```

-continued

```
His Ile Cys Ile Ile Pro Ala Glu Glu Phe Ser Thr Glu Tyr Leu
1085                1090                1095

Arg Pro Gln Val His Cys Ile Ala Ser Tyr Arg Gln His Ala Asn
1100                1105                1110

Pro Ser Ala Ser Cys Val Ser Leu Ala His Glu Thr Pro Pro Thr
1115                1120                1125

Ala Ser Ile Leu Asp Ala Thr Ser Arg Gly Leu Phe Ser Ala Leu
1130                1135                1140

Pro His Glu Pro Ser Ser Pro Ala Asp Gly Val Thr Leu Lys Ala
1145                1150                1155

Pro Gln Ser Gln Val Thr Leu Lys Gly Leu Ile Pro His Leu Gly
1160                1165                1170

Arg His Val Phe Val Ile His Phe Tyr Gln Ala Glu His Pro Gly
1175                1180                1185

Phe Pro Thr Glu Val Ile Val Asn Gly Gly Arg Gln Trp Ser Gly
1190                1195                1200

Ser Phe Leu Ala Ser Phe Cys Pro His Leu Leu Gly Cys Arg Asp
1205                1210                1215

Gln Val Ile Ser Asp Gly Gln Val Glu Phe Asp Ile Ser Glu Ala
1220                1225                1230

Glu Val Ala Val Thr Val Lys Ile Pro Asp Gly Lys Ser Leu Thr
1235                1240                1245

Leu Val Arg Val Leu Val Val Pro Ala Glu Asn Tyr Asp Tyr Gln
1250                1255                1260

Ile Leu His Lys Thr Thr Val Asp Lys Ser Ser Glu Phe Ile Ser
1265                1270                1275

Ser Cys Gly Gly Asp Ser Phe Tyr Ile Asp Pro Gln Ala Ala Ser
1280                1285                1290

Gly Phe Cys Lys Asn Ser Ala Arg Ser Leu Val Ala Phe Tyr His
1295                1300                1305

Asn Gly Ala Ile Pro Cys Glu Cys Asp Pro Ala Gly Thr Ala Gly
1310                1315                1320

His His Cys Ser Pro Glu Gly Gly Gln Cys Pro Cys Arg Pro Asn
1325                1330                1335

Val Ile Gly Arg Gln Cys Ser Arg Cys Ala Thr Gly Tyr Tyr Gly
1340                1345                1350

Phe Pro Tyr Cys Lys Pro Cys Asn Cys Gly Arg Arg Leu Cys Glu
1355                1360                1365

Glu Val Thr Gly Lys Cys Leu Cys Pro Pro His Thr Val Arg Pro
1370                1375                1380

Gln Cys Glu Val Cys Glu Met Asn Ser Phe Asn Phe His Pro Val
1385                1390                1395

Ala Gly Cys Asp Val Cys Asn Cys Ser Arg Lys Gly Thr Ile Glu
1400                1405                1410

Ala Ala Val Ser Glu Cys Asp Arg Asp Ser Gly Gln Cys Arg Cys
1415                1420                1425

Lys Pro Arg Val Thr Gly Gln Gln Cys Asp Lys Cys Ala Pro Gly
1430                1435                1440

Phe Tyr Gln Phe Pro Glu Cys Val Pro Cys Ser Cys Asn Arg Asp
1445                1450                1455

Gly Thr Glu Pro Ser Val Cys Asp Pro Glu Thr Gly Ala Cys Met
1460                1465                1470
```

-continued

```
Cys Lys Glu Asn Val Glu Gly Pro Gln Cys Gln Leu Cys Arg Glu
1475              1480              1485

Gly Ser Phe Tyr Leu Asp Pro Thr Asn Pro Lys Gly Cys Thr Lys
1490              1495              1500

Cys Phe Cys Phe Gly Val Asn Thr Asp Cys Gln Ser Ser His Lys
1505              1510              1515

Gln Arg Ala Lys Phe Val Asp Met Met Gly Trp Arg Leu Glu Thr
1520              1525              1530

Ala Asp Gly Val Asp Val Pro Val Ser Phe Asn Pro Gly Ser Asn
1535              1540              1545

Ser Met Val Ala Asp Leu Gln Glu Leu Pro Pro Ser Val His Ser
1550              1555              1560

Ala Ser Trp Val Ala Pro Pro Ser Tyr Leu Gly Asp Lys Val Ser
1565              1570              1575

Ser Tyr Gly Gly Tyr Leu Thr Tyr His Ala Lys Ser Phe Gly Leu
1580              1585              1590

Pro Gly Asp Met Val Leu Leu Gly Lys Gln Pro Asp Val Gln Leu
1595              1600              1605

Thr Gly Gln His Met Ser Leu Ile His Lys Glu Pro Ser Asp Pro
1610              1615              1620

Arg Pro Asp Arg Leu His His Gly Arg Val Gln Val Ile Glu Gly
1625              1630              1635

Asn Phe Arg His Glu Gly Ser Ser Ala Pro Val Ser Arg Glu Glu
1640              1645              1650

Leu Met Thr Val Leu Ser Arg Leu Glu Arg Leu His Ile Arg Gly
1655              1660              1665

Leu His Phe Thr Glu Thr Gln Arg Leu Thr Leu Gly Glu Val Gly
1670              1675              1680

Leu Glu Glu Ala Ser Asp Thr Gly Ser Gly Pro Arg Ala His Leu
1685              1690              1695

Val Glu Met Cys Ala Cys Pro Pro Asp Tyr Thr Gly Asp Ser Cys
1700              1705              1710

Gln Gly Cys Arg Pro Gly Tyr Tyr Trp Asp Asn Lys Ser Leu Pro
1715              1720              1725

Val Gly Arg Cys Val Pro Cys Asn Cys Asn Gly His Ser Asn Arg
1730              1735              1740

Cys Gln Asp Gly Ser Gly Ile Cys Ile Asn Cys Gln His Asn Thr
1745              1750              1755

Ala Gly Glu His Cys Glu Arg Cys Gln Ala Gly His Tyr Gly Asn
1760              1765              1770

Ala Ile His Gly Ser Cys Arg Val Cys Pro Cys Pro His Thr Asn
1775              1780              1785

Ser Phe Ala Thr Gly Cys Ala Val Asp Gly Gly Ala Val Arg Cys
1790              1795              1800

Ala Cys Lys Pro Gly Tyr Thr Gly Thr Gln Cys Glu Arg Cys Ala
1805              1810              1815

Pro Gly Tyr Phe Gly Asn Pro Gln Lys Phe Gly Gly Ser Cys Gln
1820              1825              1830

Pro Cys Asn Cys Asn Ser Asn Gly Gln Leu Gly Pro Cys Asp Pro
1835              1840              1845

Leu Thr Gly Asp Cys Val Asn Gln Glu Pro Lys Asp Gly Ser Pro
1850              1855              1860

Ala Glu Glu Cys Asp Asp Cys Asp Ser Cys Val Met Thr Leu Leu
```

-continued

```
            1865                1870                1875
Asn Asp Leu Ala Ser Met Gly Glu Glu Leu Arg Leu Val Lys Ser
    1880                1885                1890
Lys Leu Gln Gly Leu Ser Val Ser Thr Gly Ala Leu Glu Gln Ile
    1895                1900                1905
Arg His Met Glu Thr Gln Ala Lys Asp Leu Arg Asn Gln Leu Leu
    1910                1915                1920
Gly Phe Arg Ser Ala Thr Ser Ser His Gly Ser Lys Met Asp Asp
    1925                1930                1935
Leu Glu Lys Glu Leu Ser His Leu Asn Arg Glu Phe Glu Thr Leu
    1940                1945                1950
Gln Glu Lys Ala Gln Val Asn Ser Arg Lys Ala Gln Thr Leu Tyr
    1955                1960                1965
Asn Asn Ile Asp Gln Thr Ile Gln Ser Ala Lys Glu Leu Asp Met
    1970                1975                1980
Lys Ile Lys Asn Ile Val Gln Asn Val His Ile Leu Leu Lys Gln
    1985                1990                1995
Met Ala Arg Pro Gly Gly Glu Gly Thr Asp Leu Pro Val Gly Asp
    2000                2005                2010
Trp Ser Arg Glu Leu Ala Glu Ala Gln Arg Met Met Arg Asp Leu
    2015                2020                2025
Arg Ser Arg Asp Phe Lys Lys His Leu Gln Glu Ala Glu Ala Glu
    2030                2035                2040
Lys Met Glu Ala Gln Leu Leu Leu His Arg Ile Arg Thr Trp Leu
    2045                2050                2055
Glu Ser His Gln Val Glu Asn Asn Gly Leu Leu Lys Asn Ile Arg
    2060                2065                2070
Asp Ser Leu Asn Asp Tyr Glu Asp Lys Leu Gln Asp Leu Arg Ser
    2075                2080                2085
Ile Leu Gln Glu Ala Ala Ala Gln Ala Lys Gln Ala Thr Gly Ile
    2090                2095                2100
Asn His Glu Asn Glu Gly Val Leu Gly Ala Ile Gln Arg Gln Met
    2105                2110                2115
Lys Glu Met Asp Ser Leu Lys Asn Asp Phe Thr Lys Tyr Leu Ala
    2120                2125                2130
Thr Ala Asp Ser Ser Leu Leu Gln Thr Asn Asn Leu Leu Gln Gln
    2135                2140                2145
Met Asp Lys Ser Gln Lys Glu Tyr Glu Ser Leu Ala Ala Ala Leu
    2150                2155                2160
Asn Gly Ala Arg Gln Glu Leu Ser Asp Arg Val Arg Glu Leu Ser
    2165                2170                2175
Arg Ser Gly Gly Lys Ala Pro Leu Val Val Glu Ala Glu Lys His
    2180                2185                2190
Ala Gln Ser Leu Gln Glu Leu Ala Lys Gln Leu Glu Glu Ile Lys
    2195                2200                2205
Arg Asn Thr Ser Gly Asp Glu Leu Val Arg Cys Ala Val Asp Ala
    2210                2215                2220
Ala Thr Ala Tyr Glu Asn Ile Leu Asn Ala Ile Arg Ala Ala Glu
    2225                2230                2235
Asp Ala Ala Ser Lys Ala Thr Ser Ala Ser Lys Ser Ala Phe Gln
    2240                2245                2250
Thr Val Ile Lys Glu Asp Leu Pro Lys Arg Ala Lys Thr Leu Ser
    2255                2260                2265
```

-continued

```
Ser Asp Ser Glu Glu Leu Leu Asn Glu Ala Lys Met Thr Gln Lys
    2270                2275                2280

Arg Leu Gln Gln Val Ser Pro Ala Leu Asn Ser Leu Gln Gln Thr
    2285                2290                2295

Leu Lys Thr Val Ser Val Gln Lys Asp Leu Leu Asp Ala Asn Leu
    2300                2305                2310

Thr Val Ala Arg Asp Asp Leu His Gly Ile Gln Arg Gly Asp Ile
    2315                2320                2325

Asp Ser Val Val Ile Gly Ala Lys Ser Met Val Arg Glu Ala Asn
    2330                2335                2340

Gly Ile Thr Ser Glu Val Leu Asp Gly Leu Asn Pro Ile Gln Thr
    2345                2350                2355

Asp Leu Gly Arg Ile Lys Asp Ser Tyr Glu Ser Ala Arg Arg Glu
    2360                2365                2370

Asp Phe Ser Lys Ala Leu Val Asp Ala Asn Asn Ser Val Lys Lys
    2375                2380                2385

Leu Thr Arg Lys Leu Pro Asp Leu Phe Ile Lys Ile Glu Ser Ile
    2390                2395                2400

Asn Gln Gln Leu Leu Pro Leu Gly Asn Ile Ser Asp Asn Val Asp
    2405                2410                2415

Arg Ile Arg Glu Leu Ile Gln Gln Ala Arg Asp Ala Ala Asn Lys
    2420                2425                2430

Val Gly Ile Pro Ile Trp Leu
    2435                2440

<210> SEQ ID NO 11
<211> LENGTH: 360
<212> TYPE: PRT
<213> ORGANISM: Homo sapiens

<400> SEQUENCE: 11

Cys Ser Pro Leu Pro Lys Thr Gln Ala Asn His Gly Ala Leu Gln Phe
1               5                   10                  15

Gly Asp Ile Pro Thr Ser His Leu Leu Phe Lys Leu Pro Gln Glu Leu
                20                  25                  30

Leu Lys Pro Arg Ser Gln Phe Ala Val Asp Met Gln Thr Thr Ser Ser
            35                  40                  45

Arg Gly Leu Val Phe His Thr Gly Thr Lys Asn Ser Phe Met Ala Leu
        50                  55                  60

Tyr Leu Ser Lys Gly Arg Leu Val Phe Ala Leu Gly Thr Asp Gly Lys
65                  70                  75                  80

Lys Leu Arg Ile Lys Ser Lys Glu Lys Cys Asn Asp Gly Lys Trp His
                85                  90                  95

Thr Val Val Phe Gly His Asp Gly Glu Lys Gly Arg Leu Val Val Asp
                100                 105                 110

Gly Leu Arg Ala Arg Glu Gly Ser Leu Pro Gly Asn Ser Thr Ile Ser
            115                 120                 125

Ile Arg Ala Pro Val Tyr Leu Gly Ser Pro Pro Ser Gly Lys Pro Lys
        130                 135                 140

Ser Leu Pro Thr Asn Ser Phe Val Gly Cys Leu Lys Asn Phe Gln Leu
145                 150                 155                 160

Asp Ser Lys Pro Leu Tyr Thr Pro Ser Ser Ser Phe Gly Val Ser Ser
                165                 170                 175

Cys Leu Gly Gly Pro Leu Glu Lys Gly Ile Tyr Phe Ser Glu Glu Gly
```

```
                    180                 185                 190
Gly His Val Val Leu Ala His Ser Val Leu Gly Pro Glu Phe Lys
            195                 200                 205
Leu Val Phe Ser Ile Arg Pro Arg Ser Leu Thr Gly Ile Leu Ile His
210                 215                 220
Ile Gly Ser Gln Pro Gly Lys His Leu Cys Val Tyr Leu Glu Ala Gly
225                 230                 235                 240
Lys Val Thr Ala Ser Met Asp Ser Gly Ala Gly Thr Ser Thr Ser
                245                 250                 255
Val Thr Pro Lys Gln Ser Leu Cys Asp Gly Gln Trp His Ser Val Ala
            260                 265                 270
Val Thr Ile Lys Gln His Ile Leu His Leu Glu Leu Asp Thr Asp Ser
            275                 280                 285
Ser Tyr Thr Ala Gly Gln Ile Pro Phe Pro Pro Ala Ser Thr Gln Glu
            290                 295                 300
Pro Leu His Leu Gly Ala Pro Ala Asn Leu Thr Thr Leu Arg Ile
305                 310                 315                 320
Pro Val Trp Lys Ser Phe Phe Gly Cys Leu Arg Asn Ile His Val Asn
                325                 330                 335
His Ile Pro Val Pro Val Thr Glu Ala Leu Glu Val Gln Gly Pro Val
            340                 345                 350
Ser Leu Asn Gly Cys Pro Asp Gln
            355                 360

<210> SEQ ID NO 12
<211> LENGTH: 1371
<212> TYPE: DNA
<213> ORGANISM: Homo sapiens

<400> SEQUENCE: 12
tgctcaccac ttcccaagac ccaggccaat catggagccc tccagtttgg ggacattccc      60
accagccact tgctattcaa gcttcctcag gagctgctga aacccaggtc acagtttgct     120
gtggacatgc agacaacatc ctccagagga ctggtgtttc acacgggcac taagaactcc     180
tttatggctc tttatctttc aaaaggacgt ctggtctttg cactggggac agatgggaaa     240
aaattgagga tcaaaagcaa ggagaaatgc aatgatggga atggcacac ggtggtgttt     300
ggccatgatg gggaaaaggg gcgcttggtt gtggatggac tgagggcccg ggagggaagt     360
ttgcctggaa actccaccat cagcatcaga gcgccagttt acctgggatc acctccatca     420
gggaaaccaa agagcctccc cacaaacagc tttgtgggat gcctgaagaa ctttcagctg     480
gattcaaaac ccttgtatac ccttcttca agcttcgggg tgtcttcctg cttgggtggt     540
cctttggaga aaggcattta tttctctgaa gaaggaggtc atgtcgtctt ggctcactct     600
gtattgttgg ggccagaatt taagcttgtt ttcagcatcc gcccaagaag tctcactggg     660
atcctaatac acatcggaag tcagcccggg aagcacttat gtgtttacct ggaggcagga     720
aaggtcacgg cctctatgga cagtgggca ggtgggacct caacgtcggt cacaccaaag     780
cagtctctgt gtgatggaca gtggcactcg gtggcagtca ccataaaaca acacatcctg     840
cacctggaac tggacacaga cagtagctac acagctggac agatccccttcccacctgcc     900
agcactcaag agccactaca ccttggaggt gctccagcca atttgacgac actgaggatc     960
cctgtgtgga atcattctt tggctgtctg aggaatattc atgtcaatca catccctgtc    1020
cctgtcactg aagccttgga agtccagggg cctgtcagtc tgaatggttg tcctgaccag    1080
```

```
taacccaagc ctatttcaca gcaaggaaat tcaccttcaa aagcactgat tacccaatgc    1140
acctccctcc ccagctcgag atcattcttc aattaggaca caaaccagac aggtttaata    1200
gcgaatctaa ttttgaattc tgaccatgga tacccatcac tttggcattc agtgctacat    1260
gtgtatttta tataaaaatc ccatttcttg aagataaaaa aattgttatt caaattgtta    1320
tgcacagaat gttttggta atattaattt ccactaaaaa attaaatgtc t              1371
```

```
<210> SEQ ID NO 13
<211> LENGTH: 184
<212> TYPE: PRT
<213> ORGANISM: Homo sapiens

<400> SEQUENCE: 13
```

```
Cys Leu Gly Gly Pro Leu Glu Lys Gly Ile Tyr Phe Ser Glu Gly
 1               5                  10                  15

Gly His Val Val Leu Ala His Ser Val Leu Gly Pro Glu Phe Lys
                20                  25                  30

Leu Val Phe Ser Ile Arg Pro Arg Ser Leu Thr Gly Ile Leu Ile His
                35                  40                  45

Ile Gly Ser Gln Pro Gly Lys His Leu Cys Val Tyr Leu Glu Ala Gly
 50                  55                  60

Lys Val Thr Ala Ser Met Asp Ser Gly Ala Gly Thr Ser Thr Ser
 65                  70                  75                  80

Val Thr Pro Lys Gln Ser Leu Cys Asp Gly Gln Trp His Ser Val Ala
                85                  90                  95

Val Thr Ile Lys Gln His Ile Leu His Leu Glu Leu Asp Thr Asp Ser
                100                 105                 110

Ser Tyr Thr Ala Gly Gln Ile Pro Phe Pro Pro Ala Ser Thr Gln Glu
                115                 120                 125

Pro Leu His Leu Gly Gly Ala Pro Ala Asn Leu Thr Thr Leu Arg Ile
                130                 135                 140

Pro Val Trp Lys Ser Phe Phe Gly Cys Leu Arg Asn Ile His Val Asn
145                 150                 155                 160

His Ile Pro Val Pro Val Thr Glu Ala Leu Glu Val Gln Gly Pro Val
                165                 170                 175

Ser Leu Asn Gly Cys Pro Asp Gln
                180
```

```
<210> SEQ ID NO 14
<211> LENGTH: 843
<212> TYPE: DNA
<213> ORGANISM: Homo sapiens

<400> SEQUENCE: 14
tgcttgggtg gtcctttgga gaaaggcatt tatttctctg aagaaggagg tcatgtcgtc     60
ttggctcact ctgtattgtt ggggccagaa tttaagcttg ttttcagcat ccgcccaaga    120
agtctcactg ggatcctaat acacatcgga agtcagcccg ggaagcactt atgtgtttac    180
ctggaggcag gaaaggtcac ggcctctatg gacagtgggg caggtgggac ctcaacgtcg    240
gtcacaccaa agcagtctct gtgtgatgga cagtggcact cggtggcagt caccataaaa    300
caacacatcc tgcacctgga actggacaca gacagtagct acacagctgg acagatcccc    360
ttcccacctg ccagcactca agagccacta caccttggag gtgctccagc caatttgacg    420
acactgagga tccctgtgtg gaaatcattc tttggctgtc tgaggaatat tcatgtcaat    480
cacatccctg tccctgtcac tgaagccttg gaagtccagg ggcctgtcag tctgaatggt    540
```

```
tgtcctgacc agtaacccaa gcctatttca cagcaaggaa attcaccttc aaaagcactg      600
attacccaat gcacctccct ccccagctcg agatcattct tcaattagga cacaaaccag      660
acaggtttaa tagcgaatct aattttgaat tctgaccatg gatacccatc actttggcat      720
tcagtgctac atgtgtattt tatataaaaa tcccatttct tgaagataaa aaaattgtta      780
ttcaaattgt tatgcacaga atgtttttgg taatattaat ttccactaaa aaattaaatg      840
tct                                                                    843
```

```
<210> SEQ ID NO 15
<211> LENGTH: 11
<212> TYPE: PRT
<213> ORGANISM: Homo sapiens

<400> SEQUENCE: 15

Pro Leu Pro Lys Thr Gln Ala Asn His Gly Ala
1               5                   10
```

```
<210> SEQ ID NO 16
<211> LENGTH: 31
<212> TYPE: DNA
<213> ORGANISM: Homo sapiens

<400> SEQUENCE: 16
cacttcccaa gacccaggcc aatcatggag c                                      31
```

```
<210> SEQ ID NO 17
<211> LENGTH: 16
<212> TYPE: PRT
<213> ORGANISM: Homo sapiens

<400> SEQUENCE: 17

Ser His Leu Leu Phe Lys Leu Pro Gln Glu Leu Leu Lys Pro Arg Ser
1               5                   10                  15
```

```
<210> SEQ ID NO 18
<211> LENGTH: 47
<212> TYPE: DNA
<213> ORGANISM: Homo sapiens

<400> SEQUENCE: 18
gccacttgct attcaagctt cctcaggagc tgctgaaacc caggtca                     47
```

```
<210> SEQ ID NO 19
<211> LENGTH: 131
<212> TYPE: PRT
<213> ORGANISM: Homo sapiens

<400> SEQUENCE: 19

Thr Ser Ser Arg Gly Leu Val Phe His Thr Gly Thr Lys Asn Ser Phe
1               5                   10                  15

Met Ala Leu Tyr Leu Ser Lys Gly Arg Leu Val Phe Ala Leu Gly Thr
                20                  25                  30

Asp Gly Lys Lys Leu Arg Ile Lys Ser Lys Glu Lys Cys Asn Asp Gly
            35                  40                  45

Lys Trp His Thr Val Val Phe Gly His Asp Gly Glu Lys Gly Arg Leu
        50                  55                  60

Val Val Asp Gly Leu Arg Ala Arg Glu Gly Ser Leu Pro Gly Asn Ser
65                  70                  75                  80

Thr Ile Ser Ile Arg Ala Pro Val Tyr Leu Gly Ser Pro Pro Ser Gly
```

```
                85                  90                  95
Lys Pro Lys Ser Leu Pro Thr Asn Ser Phe Val Gly Cys Leu Lys Asn
            100                 105                 110

Phe Gln Leu Asp Ser Lys Pro Leu Tyr Thr Pro Ser Ser Phe Gly
        115                 120                 125

Val Ser Ser
    130

<210> SEQ ID NO 20
<211> LENGTH: 398
<212> TYPE: DNA
<213> ORGANISM: Homo sapiens

<400> SEQUENCE: 20
gacaacatcc tccagaggac tggtgtttca cacgggcact aagaactcct ttatggctct    60
ttatctttca aaggacgtc tggtctttgc actgggaca gatgggaaaa aattgaggat     120
caaaagcaag gagaaatgca atgatgggaa atggcacacg gtggtgtttg ccatgatgg    180 ggaaaagggg cgcttggttg tggatggact gagggcccgg gagggaagtt tgcctggaaa   240
ctccaccatc agcatcagag cgccagttta cctgggatca cctccatcag ggaaaccaaa   300
gagcctcccc acaaacagct ttgtgggatg cctgaagaac tttcagctgg attcaaaacc   360
cttgtatacc ccttcttcaa gcttcggggt gtcttcct                           398

<210> SEQ ID NO 21
<211> LENGTH: 315
<212> TYPE: PRT
<213> ORGANISM: Homo sapiens

<400> SEQUENCE: 21

Thr Ser Ser Arg Gly Leu Val Phe His Thr Gly Thr Lys Asn Ser Phe
1               5                   10                  15

Met Ala Leu Tyr Leu Ser Lys Gly Arg Leu Val Phe Ala Leu Gly Thr
            20                  25                  30

Asp Gly Lys Lys Leu Arg Ile Lys Ser Lys Glu Lys Cys Asn Asp Gly
        35                  40                  45

Lys Trp His Thr Val Val Phe Gly His Asp Gly Glu Lys Gly Arg Leu
    50                  55                  60

Val Val Asp Gly Leu Arg Ala Arg Glu Gly Ser Leu Pro Gly Asn Ser
65                  70                  75                  80

Thr Ile Ser Ile Arg Ala Pro Val Tyr Leu Gly Ser Pro Pro Ser Gly
                85                  90                  95

Lys Pro Lys Ser Leu Pro Thr Asn Ser Phe Val Gly Cys Leu Lys Asn
            100                 105                 110

Phe Gln Leu Asp Ser Lys Pro Leu Tyr Thr Pro Ser Ser Phe Gly
        115                 120                 125

Val Ser Ser Cys Leu Gly Gly Pro Leu Glu Lys Gly Ile Tyr Phe Ser
    130                 135                 140

Glu Glu Gly Gly His Val Val Leu Ala His Ser Val Leu Leu Gly Pro
145                 150                 155                 160

Glu Phe Lys Leu Val Phe Ser Ile Arg Pro Arg Ser Leu Thr Gly Ile
                165                 170                 175

Leu Ile His Ile Gly Ser Gln Pro Gly Lys His Leu Cys Val Tyr Leu
            180                 185                 190

Glu Ala Gly Lys Val Thr Ala Ser Met Asp Ser Gly Ala Gly Gly Thr
        195                 200                 205
```

Ser Thr Ser Val Thr Pro Lys Gln Ser Leu Cys Asp Gly Gln Trp His
    210                 215                 220

Ser Val Ala Val Thr Ile Lys Gln His Ile Leu His Leu Glu Leu Asp
225                 230                 235                 240

Thr Asp Ser Ser Tyr Thr Ala Gly Gln Ile Pro Phe Pro Pro Ala Ser
                245                 250                 255

Thr Gln Glu Pro Leu His Leu Gly Gly Ala Pro Ala Asn Leu Thr Thr
            260                 265                 270

Leu Arg Ile Pro Val Trp Lys Ser Phe Phe Gly Cys Leu Arg Asn Ile
        275                 280                 285

His Val Asn His Ile Pro Val Pro Val Thr Glu Ala Leu Glu Val Gln
    290                 295                 300

Gly Pro Val Ser Leu Asn Gly Cys Pro Asp Gln
305                 310                 315

<210> SEQ ID NO 22
<211> LENGTH: 935
<212> TYPE: DNA
<213> ORGANISM: Homo sapiens

<400> SEQUENCE: 22
catcctccag aggactggtg tttcacacgg gcactaagaa ctcctttatg gctctttatc      60
tttcaaaagg acgtctggtc tttgcactgg ggacagatgg gaaaaaattg aggatcaaaa    120
gcaaggagaa atgcaatgat gggaaatggc acacggtggt gtttggccat gatggggaaa    180
aggggcgctt ggttgtggat ggactgaggg cccgggaggg aagtttgcct ggaaaactcca   240
ccatcagcat cagagcgcca gtttacctgg gatcacctcc atcagggaaa ccaaagagcc    300
tccccacaaa cagctttgtg ggatgcctga agaactttca gctggattca aaacccttgt    360
atacccttc ttcaagcttc ggggtgtctt cctgcttggg tggtcctttg agaaaggca     420
tttatttctc tgaagaagga ggtcatgtcg tcttggctca ctctgtattg ttggggccag    480
aatttaagct tgttttcagc atccgcccaa gaagtctcac tgggatccta atacacatcg    540
gaagtcagcc cgggaagcac ttatgtgttt acctggaggc aggaaaggtc acggcctcta    600
tggacagtgg ggcaggtggg acctcaacgt cggtcacacc aaagcagtct ctgtgtgatg    660
gacagtggca ctcggtggca gtcaccataa acaacacat cctgcacctg aactggaca     720
cagacagtag ctacacagct ggacagatcc cttcccacc tgccagcact caagagccac    780
tacaccttgg aggtgctcca gccaatttga cgacactgag gatccctgtg tggaaatcat    840
tctttggctg tctgaggaat attcatgtca atcacatccc tgtccctgtc actgaagcct    900
tggaagtcca ggggcctgtc agtctgaatg gttgt                               935

<210> SEQ ID NO 23
<211> LENGTH: 154
<212> TYPE: PRT
<213> ORGANISM: Homo sapiens

<400> SEQUENCE: 23

Phe Lys Leu Val Phe Ser Ile Arg Pro Arg Ser Leu Thr Gly Ile Leu
1               5                   10                  15

Ile His Ile Gly Ser Gln Pro Gly Lys His Leu Cys Val Tyr Leu Glu
            20                  25                  30

Ala Gly Lys Val Thr Ala Ser Met Asp Ser Gly Ala Gly Gly Thr Ser
        35                  40                  45

```
Thr Ser Val Thr Pro Lys Gln Ser Leu Cys Asp Gly Gln Trp His Ser
    50                  55                  60

Val Ala Val Thr Ile Lys Gln His Ile Leu His Leu Glu Leu Asp Thr
65                  70                  75                  80

Asp Ser Ser Tyr Thr Ala Gly Gln Ile Pro Phe Pro Pro Ala Ser Thr
                85                  90                  95

Gln Glu Pro Leu His Leu Gly Gly Ala Pro Ala Asn Leu Thr Thr Leu
            100                 105                 110

Arg Ile Pro Val Trp Lys Ser Phe Phe Gly Cys Leu Arg Asn Ile His
            115                 120                 125

Val Asn His Ile Pro Val Pro Val Thr Glu Ala Leu Glu Val Gln Gly
    130                 135                 140

Pro Val Ser Leu Asn Gly Cys Pro Asp Gln
145                 150

<210> SEQ ID NO 24
<211> LENGTH: 462
<212> TYPE: DNA
<213> ORGANISM: Homo sapiens

<400> SEQUENCE: 24
ttaagcttgt tttcagcatc cgcccaagaa gtctcactgg gatcctaata cacatcggaa      60
gtcagcccgg gaagcactta tgtgtttacc tggaggcagg aaaggtcacg gcctctatgg     120
acagtggggc aggtgggacc tcaacgtcgg tcacaccaaa gcagtctctg tgtgatggac     180
agtggcactc ggtggcagtc accataaaac aacacatcct gcacctggaa ctggacacag     240
acagtagcta cacagctgga cagatcccct tcccacctgc cagcactcaa gagccactac     300
accttggagg tgctccagcc aatttgacga cactgaggat ccctgtgtgg aaatcattct     360
ttggctgtct gaggaatatt catgtcaatc acatccctgt ccctgtcact gaagccttgg     420
aagtccaggg gcctgtcagt ctgaatggtt gtcctgacca gt                       462
```